US008765661B2

(12) United States Patent
Bromley

(10) Patent No.: US 8,765,661 B2
(45) Date of Patent: Jul. 1, 2014

(54) COMPOSITIONS CONTAINING NON-POLAR COMPOUNDS

(75) Inventor: Philip J. Bromley, Fullerton, CA (US)

(73) Assignee: Virun, Inc., Walnut, CA (US)

(*) Notice: Subject to any disclaimer, the term of this patent is extended or adjusted under 35 U.S.C. 154(b) by 806 days.

(21) Appl. No.: 12/383,241

(22) Filed: Mar. 20, 2009

(65) Prior Publication Data
US 2009/0297491 A1 Dec. 3, 2009

Related U.S. Application Data

(60) Provisional application No. 61/070,392, filed on Mar. 20, 2008, provisional application No. 61/132,409, filed on Jun. 16, 2008.

(51) Int. Cl.
A01N 61/00 (2006.01)

(52) U.S. Cl.
USPC .......................................................... 514/1

(58) Field of Classification Search
None
See application file for complete search history.

(56) References Cited

U.S. PATENT DOCUMENTS

| | | | | |
|---|---|---|---|---|
| 2,680,749 A | 6/1954 | Cawley et al. | | 549/410 |
| 3,102,078 A * | 8/1963 | Robeson | | 514/458 |
| 3,538,119 A | 11/1970 | Grant | | 549/410 |
| 4,353,365 A | 10/1982 | Hallworth et al. | | 128/203.15 |
| 4,524,769 A | 6/1985 | Wetterlin | | 128/203.15 |
| 4,665,204 A | 5/1987 | Wirth | | 549/410 |
| 4,670,285 A | 6/1987 | Clandinin et al. | | 426/602 |
| 4,835,002 A | 5/1989 | Wolf et al. | | 426/590 |
| 4,867,986 A * | 9/1989 | Desai et al. | | 424/464 |
| 4,916,163 A | 4/1990 | Ni | | 514/458 |
| 5,035,237 A | 7/1991 | Newell et al. | | 128/203.15 |
| 5,167,950 A | 12/1992 | Lins | | 424/47 |
| 5,179,122 A | 1/1993 | Greene et al. | | 514/458 |
| 5,234,695 A | 8/1993 | Hobbs et al. | | 424/489 |
| 5,239,993 A | 8/1993 | Evans | | 128/203.15 |
| 5,340,589 A | 8/1994 | Stetsko et al. | | 424/462 |
| 5,397,591 A | 3/1995 | Kyle et al. | | 426/602 |
| 5,407,957 A | 4/1995 | Kyle et al. | | 514/547 |
| 5,415,162 A | 5/1995 | Casper et al. | | 128/203.12 |
| 5,430,021 A | 7/1995 | Rudnic et al. | | 514/14 |
| 5,492,938 A | 2/1996 | Kyle et al. | | 514/786 |
| 5,583,105 A * | 12/1996 | Kovacs et al. | | 514/20.5 |
| 5,591,772 A | 1/1997 | Lane et al. | | 514/458 |
| 5,593,682 A | 1/1997 | Papas et al. | | 424/401 |
| 5,711,983 A | 1/1998 | Kyle et al. | | 426/635 |
| 5,715,810 A | 2/1998 | Armstrong | | 128/203.15 |
| 5,798,333 A | 8/1998 | Sherman | | 514/11 |
| 5,821,264 A | 10/1998 | Lane et al. | | 514/458 |
| 5,891,469 A * | 4/1999 | Amselem | | 424/451 |
| 5,908,940 A | 6/1999 | Lane et al. | | 549/453 |
| 5,919,818 A | 7/1999 | Lane et al. | | 514/458 |
| 6,045,826 A | 4/2000 | Borowy-Borowski et al. | | 424/451 |
| 6,086,915 A | 7/2000 | Zeligs et al. | | 424/455 |
| 6,136,851 A | 10/2000 | Bonte et al. | | 514/458 |
| 6,143,770 A | 11/2000 | Lane et al. | | 514/332 |
| 6,162,474 A | 12/2000 | Chen et al. | | 426/72 |
| 6,180,130 B1 | 1/2001 | Chen et al. | | 424/439 |
| 6,193,793 B1 | 2/2001 | Long et al. | | 106/284.05 |
| 6,193,985 B1 * | 2/2001 | Sonne | | 424/400 |
| 6,204,290 B1 | 3/2001 | Lane et al. | | 514/456 |
| 6,239,171 B1 | 5/2001 | Lane et al. | | 514/458 |
| 6,267,985 B1 | 7/2001 | Chen et al. | | 424/451 |
| 6,284,268 B1 | 9/2001 | Mishra et al. | | 424/455 |
| 6,335,022 B1 | 1/2002 | Simonnet et al. | | 424/401 |
| 6,378,519 B1 | 4/2002 | Davies et al. | | 128/203.21 |
| 6,383,471 B1 | 5/2002 | Chen et al. | | 424/45 |
| 6,391,370 B1 | 5/2002 | Rogers et al. | | 426/611 |
| 6,416,786 B1 | 7/2002 | Mulye et al. | | 424/468 |
| 6,416,793 B1 | 7/2002 | Zeligs et al. | | 424/725 |
| 6,437,000 B1 | 8/2002 | Mulye | | 514/647 |
| 6,455,512 B1 | 9/2002 | Ward et al. | | 514/59 |
| 6,475,493 B1 | 11/2002 | Mulye | | 424/400 |
| 6,509,044 B2 | 1/2003 | Van Den Braak et al. | | 426/2 |
| 6,534,085 B1 | 3/2003 | Zeligs | | 424/451 |
| 6,632,443 B2 | 10/2003 | Borowy-Borowski et al. | | 424/400 |
| 6,635,680 B2 | 10/2003 | Mulye | | 424/471 |
| 6,761,903 B2 | 7/2004 | Chen et al. | | 424/451 |
| 6,870,077 B2 | 3/2005 | Kenaschuk | | 800/298 |
| 6,919,378 B2 | 7/2005 | Jacobs et al. | | 514/618 |
| 6,946,146 B2 | 9/2005 | Mulye | | 424/479 |
| 6,977,166 B1 | 12/2005 | Ratledge et al. | | 435/134 |
| 6,979,456 B1 | 12/2005 | Parikh et al. | | 424/422 |
| 6,982,281 B1 | 1/2006 | Chen et al. | | 514/458 |

(Continued)

FOREIGN PATENT DOCUMENTS

| | | |
|---|---|---|
| WO | WO 96/36316 | 11/1996 |
| WO | WO 98/08490 | 3/1998 |
| WO | WO 99/59421 | 11/1999 |
| WO | WO 00/23545 | 4/2000 |
| WO | WO 02/017879 | 3/2002 |
| WO | WO 2009/117151 | 8/2002 |
| WO | WO 02/076970 | 10/2002 |
| WO | WO 2004/098311 | 11/2004 |
| WO | WO 2005/105290 | 11/2005 |
| WO | WO 2006/009825 | 1/2006 |

(Continued)

OTHER PUBLICATIONS

Antares Health Products "Vitamen-E TPGS," product brochure distributed at SupplySide Trade Show Oct. 22, 2008. [2 pages].

(Continued)

Primary Examiner — Sean Aeder
(74) Attorney, Agent, or Firm — McKenna Long & Aldridge LLP; Stephanie Seidman

(57) ABSTRACT

Provided herein are compositions and methods for preparing foods and beverages that contain additives, such as nutraceuticals, pharmaceuticals, and supplements, such as essential fatty acids, including omega-3 fatty acids, omega-6 fatty acids, conjugated fatty acids, and other fatty acids; phytochemicals, including phytosterols; other oils; and coenzymes, including Coenzyme Q10, and other oil-based additives.

63 Claims, 1 Drawing Sheet

(56) References Cited

U.S. PATENT DOCUMENTS

| | | |
|---|---|---|
| 6,982,282 B2 | 1/2006 | Lambert et al. ............... 424/405 |
| 7,060,672 B2 | 6/2006 | Naicker et al. .................... 514/2 |
| 7,094,804 B2 | 8/2006 | Behnam ........................ 514/460 |
| 7,115,565 B2 | 10/2006 | Gao et al. ........................ 514/9 |
| 7,182,950 B2 | 2/2007 | Garti et al. ..................... 424/401 |
| 7,273,624 B2 | 9/2007 | Rosenberg et al. ........... 424/489 |
| 8,282,977 B2 | 10/2012 | Bromley ......................... 426/72 |
| 8,337,931 B2 | 12/2012 | Bromley ....................... 426/602 |
| 8,414,914 B2 | 4/2013 | Bromley et al. .............. 424/450 |
| 2001/0025058 A1 | 9/2001 | Borowy-Borowski et al. ........................... 514/772.4 |
| 2003/0072798 A1 | 4/2003 | Schwarz ....................... 424/456 |
| 2003/0180352 A1 | 9/2003 | Patel et al. .................... 424/465 |
| 2004/0043043 A1 | 3/2004 | Schlyter et al. .............. 424/400 |
| 2004/0072330 A1 | 4/2004 | Ratledge et al. ........... 435/258.1 |
| 2004/0115287 A1 | 6/2004 | Chen et al. .................... 424/731 |
| 2004/0121043 A1 | 6/2004 | Behnam ........................ 514/458 |
| 2004/0219274 A1 | 11/2004 | Cook ............................. 426/590 |
| 2005/0037073 A1 | 2/2005 | Schwarz .......................... 42/464 |
| 2005/0092969 A1 | 5/2005 | Ueda et al. .................... 252/399 |
| 2005/0208082 A1 | 9/2005 | Papas et al. ................... 424/400 |
| 2005/0281772 A1 | 12/2005 | Bromley et al. ........... 424/70.14 |
| 2006/0051462 A1 | 3/2006 | Wang .............................. 426/72 |
| 2006/0088558 A1 | 4/2006 | Jandzinski et al. ........... 424/400 |
| 2006/0165735 A1 | 7/2006 | Abril ............................. 426/601 |
| 2006/0165769 A1 | 7/2006 | Hyatt et al. ................... 424/450 |
| 2006/0222716 A1 | 10/2006 | Schwarz et al. .............. 424/490 |
| 2006/0251690 A1 | 11/2006 | Lipshutz et al. .............. 424/401 |
| 2007/0003614 A1 | 1/2007 | Chen et al. .................... 424/456 |
| 2007/0087104 A1 | 4/2007 | Chanamai ..................... 426/602 |
| 2007/0104741 A1 | 5/2007 | Murty et al. .................. 424/400 |
| 2007/0104778 A1 | 5/2007 | Zeng et al. .................... 424/451 |
| 2007/0104780 A1 | 5/2007 | Lipari et al. .................. 424/456 |
| 2007/0141203 A1 | 6/2007 | Cook .............................. 426/72 |
| 2007/0141224 A1 | 6/2007 | Zawistowski ................. 426/611 |
| 2007/0166411 A1 | 7/2007 | Anthony et al. .............. 424/750 |
| 2007/0184117 A1* | 8/2007 | Gregory et al. ............... 424/489 |
| 2007/0207196 A1 | 9/2007 | Zhang ........................... 424/450 |
| 2007/0218012 A1 | 9/2007 | Bittorf et al. ................... 424/45 |
| 2007/0218138 A1 | 9/2007 | Bittorf et al. ................. 424/488 |
| 2007/0248668 A1 | 10/2007 | Michaelis et al. ............ 424/464 |
| 2007/0298083 A1 | 12/2007 | Mehansho et al. ........... 426/590 |
| 2007/0298099 A1 | 12/2007 | Peresypkin et al. .......... 424/456 |
| 2008/0070981 A1 | 3/2008 | Borowy-Borowski et al. ............................. 514/458 |
| 2008/0233056 A1 | 9/2008 | Berl ................................ 424/49 |
| 2008/0254188 A1 | 10/2008 | Borowy-Borowski et al. ............................. 426/590 |
| 2009/0018186 A1 | 1/2009 | Chen et al. .................... 426/590 |
| 2009/0297665 A1 | 12/2009 | Bromley |
| 2009/0317532 A1 | 12/2009 | Bromley |
| 2010/0041622 A1 | 2/2010 | Bromley et al. |
| 2010/0080785 A1 | 4/2010 | Berl ............................. 424/94.1 |
| 2010/0136175 A1 | 6/2010 | Skiff et al. ..................... 426/72 |
| 2011/0008305 A1 | 1/2011 | Yu et al. ...................... 424/94.1 |
| 2011/0015266 A1 | 1/2011 | Hanefeld et al. ........... 252/363.5 |
| 2011/0117184 A1 | 5/2011 | Bromley et al. |
| 2011/0118351 A1 | 5/2011 | Berl ............................. 514/560 |
| 2011/0236364 A1 | 9/2011 | Bromley |
| 2012/0016026 A1 | 1/2012 | Bromley et al. |
| 2012/0308644 A1 | 12/2012 | Bromley et al. |
| 2013/0017183 A1 | 1/2013 | Bromley |
| 2013/0017295 A1 | 1/2013 | Bromley |
| 2013/0309362 A1 | 11/2013 | Bromley ......................... 424/72 |

FOREIGN PATENT DOCUMENTS

| | | |
|---|---|---|
| WO | WO 2007/080515 | 7/2007 |
| WO | WO 2008/039564 | 4/2008 |
| WO | WO 2008/134766 | 11/2008 |
| WO | WO 200/029046 | 3/2009 |
| WO | WO 2009/117152 | 9/2009 |
| WO | WO 2010/008475 | 1/2010 |
| WO | WO 2010/008762 | 1/2010 |
| WO | WO 2010/019255 | 2/2010 |

OTHER PUBLICATIONS

Byberg et al., "Plasminogen activator inhibitor-1 and relations to fatty acid composition in the diet and in serum cholesterol esters," Arteroscler. Thromb. Vasc. Biol. 21:2086-2092 (2001).

Colas et al., "Sensitization by dietary docosahexaenoic acid of rat mammary carcinoma to anthracycline: A Role for tumor vascularization," Clin. Cancer Res. 12(19):5879-5886 (2006).

Covington, M., "Omega-3 fatty acids," American Family Physician 70(1):133-140 (2004).

Ernst, E., "The risk-benefit profile of commonly used herbal therapies: Ginkgo, St. John's Wort, Ginseng, Echinacea, Saw Palmetto, and Kava," Ann Intern Med. 136:42-53 (2002).

Fan, Y. and R. Chapkin, "Importance of dietary γ-linolenic acid in human health and nutrition," Journal of Nutrition 1411-1414 (1998).

Gordon, A. and A. Shaughnessy, "Saw palmetto for prostate disorders," American Family Physician 67(6):1281-1283 (2003).

Green et al., "Dietary docosahexaenoic acid and docosapentaenoic acid ameliorate amyloid-beta tau pathology via a mechanism involving presenilin 1 levels," J. Neuroscience 27(16):4385-4395 (2007).

Griffin, W., "Classification of surface-reactive agents by HLB," J. Soc. Cos. Chem. 1:311-326 (1949).

Lands, W., "Biochemistry and physiology of n-3 fatty acids," The FASEB Journal, 6(8):2530-2536 (1992).

Miyashita, K., "Effects of chemical properties of oil in water emulsion on lipid peroxidation," Foods Food Ingredients J. Jpn. 209(11):1-2 (2004).

Osako et al., "Effect of starvation on lipid metabolism and stability of DHA content of lipids in Horse Mackerel (*Trachurus japonicus*) tissues," Lipids 38(12):1263-1267 (2003).

Perry, R. and D. Green, *Perry's Chemical Engineers' Handbook*, Sixth Edition, New York:McGraw-Hill, pp. 20-54 to 20-57 (1984).

Ross et al., "Omega-3 fatty acids as treatments for mental illness: which disorder and which fatty acid?," Lipids in Health and Disease 6:21 pp. 1-19 (2007).

Starling, S., "Virun debuts shelf-stable, H2O soluble, nanotech omega-3," found at: www.beveragedaily.com/Products/Virun-debuts-shelf-stable-H20-soluble-nanotech-omega-3 , Beveragedaily.com News Release Mar. 12, 2009. [2 pages].

Virun Product Sheet, "Clear oils for water based beverages," Jan. 16, 2009. [4 pages].

Virun home Webpage found at: www.virun.com [accessed on May 8, 2009] [34 pages].

Virun on slideshare.net, Philip Bromley's Presentations on SlideShare found at: www.slideshare.net/virun [accessed on May 8, 2009] [5 pages].

Virun Improving Life Through Safe & Effective Oral Delivery found at: www.slideshare.net/virun/virun-improving-life-through-safe-effective-oral-delivery [accessed on May 11, 2009] [15 pages].

Virun Clear Water Soluble Omega-3 DHA, EPA & ALA for Foods & Beverages found at: www.slideshare.net/virun/virun-food-beverage-division-v2 [accessed on May 11, 2009] [9 pages].

Virun Pharmaceutical & Food Beverage Divisions: www.slideshare.net/virun/virun-food-beverage-divisions [accessed on May 11, 2009] [9 pages].

Wright, R., "Companies to watch-Nutraceuticals World," located at: www.nutraceuticalsworld.com/articles/2009/06/companies-to-watch, (2009) [accessed on Jun. 4, 2009] [7 pages].

Letter/Written Disclosure of the Information Disclosure Statement for the above-referenced application, mailed Dec. 12, 2011, 2 pages.

Eastman PCI-102B Publication, "Vitamin E TPGS NF—applications and properties, " Eastman Chemical Company, Publication PCI-102B, Oct. 2005, 24 pages.

Virun home Webpage [online][retrieved on Mar. 24, 2011]Retrieved from:<URL:virun.com [59 pages].

Virun Intricate Science [online][retrieved on May 25, 2011]Retrieved from:<URL:slideshare.net/virun/virun-intricate-science [22 pages].

(56) References Cited

OTHER PUBLICATIONS

Response to Written Opinion, issued Jul. 3, 2009, in connection with related International Patent Application No. PCT/US2009/001775, 35 pages.
Response to Written Opinion, issue Feb. 4, 2010, in connection with corresponding International Application No. PCT/US2009/003761, 25 pages.
Response to Written Opinion, issued Apr. 1, 2010, in connection with related International Patent Application No. PCT/US2009/001774, 37 pages.
International Preliminary Report on Patentability, issued Jun. 11, 2010, in connection with related International Patent Application No. PCT/US2009/001775, 18 pages.
International Preliminary Report on Patentability, issued Jul. 27, 2010, in connection with related International Patent Application No. PCT/US2009/003761, 13 pages.
International Preliminary Report on Patentability, issued Sep. 3, 2010, in connection with related International Patent Application No. PCT/US2009/001774, 15 pages.
Examination Report, issued Mar. 7, 2011, in connection with related Eurpoean Patent Application No. 09722985.0, 6 pages.
Response to Examination Report, issued Mar. 7, 2011, in connection with related European Patent Application No. 097226985.0, 7 pages.
International Search Report and Written Opinion, issued Jul. 22, 2011, for related International Application No. PCT/US2011/000538, 11 pages.
International Search Report and Written Opinion, issued Sep. 26, 2011, in connection with International Application No. PCT/US2011/001099, 9 pages.
Letter/Written Disclosure of the Supplemental Information Disclosure Statement for the above-referenced application, mailed on Mar. 8, 2012, 2 pages.
Response to Written Opinion, issued Jul. 22, 2011, for corresponding International Application No. PCT/US2011/000538, 9 pages.
Office Action, received Feb. 8, 2012, in connection with Chinese patent Application No. 200980118257.4, 2 pages.
IPEC—Americas News, "IPEC—Americas Gains Four New Members in May," pp. 1-12, May 2008.
Letter/Written Disclosure of the Supplemental Information Disclosure Statement for the above-referenced application, mailed on Jul. 30, 2012, 2 pages.
Response to Written Opinion, issued Sep. 26, 2011, in connection with related International Application No. PCT/US2011/001099, 10 pages.
Instructions for Response to Office Action, received Feb. 8, 2010, in connection with corresponding Chinese patent Application No. 200980118257.4, 13 pages.
Office Action, issued Mar. 28, 2012, in connection with corresponding Canadian Patent Application No. 2,715,018, 2 pages.
Response to Office Action, issued Mar. 28, 2012, in connection with corresponding Canadian Patent Application No. 2,715,018, 7 pages.
Communication 71(3)—Itention to Grant corresponding European Patent Application No. 09723157.5, issued Nov. 8, 2011, 5 pages.
Notice of Allowance, issued May 17, 2012 in connection with corresponding Canadian Patent Application No. 2,715,018. 1 page.
Communication reporting grant of related European Patent Application No. 09723157.5, issued May 16. 2012, 2 pages.
Communication 71(3)—Intention to grant related European Patent Application No. 09722985.0, issued Jun. 15, 2012, 5 pages.
International Preliminary Report on Patentablity, mailed Jul. 17, 2012 in connection with related International Patent Application No. PCT/US2011/000538, 12 pages.
Letter/Written Disclosure of the Supplemental Information Disclosure Statement for the above-referenced application, mailed on Dec. 20, 2013, 2 pages.
Boukley, B. "'Next Generation' Omega-3 sports drink set to hydrate America" Beveragedaily.com Aug. 1, 2013 [online] [retrieved at http://www.beveragedaily.com/content/view/print/804977] [accessed on Aug. 16, 2013], 2 pages.

Boukley, B. "Runaway Omega-3 beverage demand 'can be scary'—Virun CEO" Beveragedaily.com Dec. 20, 2012 [online] [retrieved at http://www.beveragedaily.com/content/view/print/711158] [accessed on Aug. 16, 2013], 2 pages.
Boukley, B. "Searching for the Holy Grail: Science-backed functional beverages" Beveragedaily.com Mar. 3, 2013 [online] [retrieved at http://www.beveragedaily.com/content/view/print/749075] [accessed on Aug. 16, 2013], 2 pages.
Boukley, B. "Stepan Lipid Nutrition and Virun paint bold brushstrokes on clear beverage 'canvas'," Beveragedaily.com Apr. 11, 2013 [online] [retrieved at http://www.beveragedaily.com/content/view/print/761692] [accessed on Aug. 16, 2013], 2 pages.
Boukley, B. "Time for a Change . . . Cola? US firm heralds healthy cola revolution'," Beveragedaily.com Apr. 30, 2013 [online] [retrieved at http://www.beveragedaily.com/content/view/print/769020] [accessed on Aug. 16, 2013], 2 pages.
Engreadea News & Analysis, "VIRUN, Vital Pharmaceuticals expand operations", published Nov. 5, 2013, found at http://newhope360.coin/print/specialty/virun-vital-pharmaceuticals-expand-operations [accessed Dec. 17, 2013], 2 pages.
Gander, P. "Sea changes," published Nov. 5, 2013, found at http://www.foodmanufacture.co.uk/content/view/print/843822 [accessed Dec. 17, 2013], 2 pages.
Higgins, K., "Emerging Plant Technologies Help Processors Make Better Beverages," Food Processing, found at: http://www.foodprocessing.com/articles/2013/beverage-technology/?show=all [accessed Dec. 17, 2013], 3 pages.
Lipshutz et al., "Transition—metal—catalyzed cross-couplings going green: in water at room temperature." Aldrichimica Acta 41(3):59-72 (2008).
Press Release: "Virun and Vital Pharmaceuticals Expand Operations" found at: http://www.bevnet.com/news/supplier-news/2013/virun-and-vital-pharmaceuticals-expand-operations/ Oct. 31, 2013, 2 pages.
Schultz, H. "PQQ set to make splash in sports nutrition beverages," nutraingredients-usa.com Aug. 6, 2013 [online] [retrieved at http://www.nutraingredients-usa.com/content/view/print/807624] [accessed on Aug. 16, 2013], 2 pages.
Virun Facebook Page found at https://www.facebook.com/pages/Virun/168007462662 [accessed on Aug. 16, 2013], 8 pages.
Virun Facebook Page found at https://www.facebook.com/pages/Virun/168007462662 [accessed on Dec. 17, 2013], 6 pages.
Office Action and Search Report, issued May 15, 2013, and translation, in connection with Chinese Patent Application No. 200980132984.6, 15 pages.
Office Action, issued Jul. 4, 2013, in connection with Australian Patent Application No. 2009226019, 2 pages.
Response to Office Action, submitted Jul. 19, 2013, and instructions for response, in connection with Chinese patent Application No. 200980118258.9, 25 pages.
Response to Office Action, submitted Jul. 22, 2013, in connection with Australian Patent Application No. 2009226019, 18 pages.
Response to Rule 70(2) and 70a(2) communication, submitted Jul. 23, 2013, in conneciton with European Patent Application No. 12188577.6, 9 pages.
Supplemental Response to Office Action, submitted Jul. 26, 2013, in connection with Australian Patent Application No. 2009226019, 19 pages.
Office Action, issued Jul. 30, 2013, and translation, in connection with Chinese Patent Application No. 200980118257.4, 6 pages.
Notice of Acceptance, issued Aug. 15, 2013, in connection with Australian Patent Application No. 2009226019, 2 pages.
Office Action and Search Report, issued Aug. 21, 2013, and translation, in connection with Chinese Patent Application No. 201180025197.9, 12 pages.
Translation of Response to Office Action, submitted Sep. 10, 2013, in connection with Israeli Patent Application No. 208133, 16 pages.
Final Office Action, issued Sep. 23, 2013, in connection with U.S. Appl. No. 90/012,700, 46 pages.
Response to Office Action, submitted Sep. 26, 2013, in connection with with U.S. Appl. No. 13/134,927, 25 pages.

(56) References Cited

OTHER PUBLICATIONS

Response to Office Action, submitted Sep. 30, 2013, and instruction for response, in connection with Chinese Patent Application No. 200980132984.6, 24 pages.
Voluntary Amendment, submitted Oct. 30, 2013, and instruction for amendment, in connection with corresponding Chinese Patent Application No. 20130096300.X, 15 pages.
Response to Office Action, submitted Nov. 25, 2013, in connection with U.S. Appl. No. 90/012,700, 73 pages.
Advisory Action, issued Dec. 6, 2013, in connection with U.S. Appl. No. 90/012,700, 4 pages.
Summary of issues to discuss in interview, submitted Dec. 10, 2013, in connection with U.S. Appl. No. 90/012,700, 6 pages.
Response to Office Action, submitted Dec. 16, 2013, and instructions for response to Office Action, in connection with Chinese Patent Application No. 200980118257.4, 30 pages.
Letter/Written Disclosure of the Supplemental Information Disclosure Statement for the above-referenced application, mailed on Feb. 21, 2013, 3 pages.
Office Action, issued Jan. 5, 2013 and translation, in connection with Chinese Patent Application No. 200980118257.4, 8 pages.
U.S. Appl. No. 60/887,754, filed Feb. 1, 2007, Borowy-Borowski et al.
Letter/Written Disclosure of the Supplemental Information Disclosure Statement for the above-referenced application, mailed on Jun. 19, 2013, 2 pages.
"Alpha-Tocopherol Polyethylene glycol Succinate (TPGS)," Pure Matters website [online][retrieved on Feb. 26, 2013] Retrieved from:<URL: resources.purematters.com/herbs-supplements/a/alpha-tocopherol-polyethylene-glycol-succinate-tpgs [2 pages].
Bromley, P., "Nanotechnology and nonpolar active compounds in functional foods: An application note," *Bio-Nanotechnology: A Revolution in Food, Biomedical and Health Sciences* (eds. Bagchi et al.), Blackwell Publishing Ltd., Oxford, UK (2013).
Offer for Sale, "Kaneka Liquid CoQ10" formulation, to Kaneka Nutrients L.P., Pasadena, TX, on Jun. 22-27, 2007, 2 pages.
Press Release, "OmegaH2O® clear shelf stable Omega-3, CoQ10 and other non polar compounds U.S. Appl. No. 12/383,244 approved in europe and notice of allowance in U.S," Published on Jun. 4, 2012 [online] Retrieved from:<URL:pr.com/press-release/417599 Jun. 4, 2012 [4 pages].
Press Release: "VIRUN® closes $2.1 million series—A funding to bolster innovation and world-wide expansion," Published on Aug. 2, 2012 [online] Retrieved from:<URL:pr.com/press-release/431579 [4 pages].
Swern, D., *Bailey's Industrial Oil and Fat Products*, vol. 1, 4th edition. John Wiley & Sons, New York, pp. 387-391 and then 424-428 (1979).
Virun, "Virun Omega 3 Fortified Foods and Beverages," retrieved from the Internet:<URL: slideshare.net/virun/virun-omega-3-fortified-foods-and-beverages, [retrieved on May 7, 2010] [15 pages].
Office Action, issued Oct. 4, 2011, in connection with U.S. Appl. No. 12/383,244, 13 pages.
Examination Report, issued Dec. 19, 2011, in connection with European Patent Application No. 09722985.0, 4 pages.
Examiner's Report, issued Mar. 28, 2012, in connection with Canadian Patent Application No. 2,718,231, 3 pages.
Response to Office Action, submitted Apr. 4, 2012, in connection with U.S. Appl. No. 12/383,244, 16 pages.
Response to Examination Report, submitted Apr. 5, 2012, in connection with European Patent Application No. 09722985.0, 60 pages.
Decision to Grant, issued Apr. 19, 2012, in connection with corresponding European Patent Application No. 09723157.5, 1 page.
PCT Communication, issued Apr. 25, 2012, in connection with International Patent Application No. PCT/US2011/000538, 4 pages.
Notice of Allowance, issued May 30, 2012, in connection with U.S. Appl. No. 12/383,244, 5 pages.
Translation of Office Action, issued May 31, 2012, in connection with Chinese Patent Application No. 200980118258.9, 1 page.
Second Written Opinion, issued Jun. 1, 2012 in connection with International Patent Application No. PCT/US2011/001099, 5 pages.
Response to Examiner's Report, submitted Jun. 8, 2012, in connection with Canadian Patent Application No. 2,718,231, 18 pages.
Response to PCT Communication, submitted Jun. 25, 2012, in connection with International Patent Application No. PCT/US2011/000538, 5 pages.
Response to Written Opinion, submitted Aug. 1, 2012 in connection with International Patent Application No. PCT/US2011/001099, 5 pages.
Supplemental Notice of Allowance, issued Aug. 17, 2012, in connection with U.S. Appl. No. 12/383,244, 1 page.
Examination Report, issued Aug. 17, 2012, in connection with Canadian Patent Application No. 2,718,231, 2 pages.
International Preliminary Report on Patentability, issued Aug. 20, 2012, in connection with International Patent Application No. PCT/US2011/001099, 16 pages.
Response to Examination Report, submitted Aug. 29, 2012, in connection with Canadian Patent Application No. 2,718,231, 11 pages.
Office Action, issued Sep. 6, 2012, in connection with U.S. Appl. No. 13/065,510, 22 pages.
Third Party Reexamination Request, submitted Oct. 9, 2012, in connection with U.S. Appl. No. 8,282,977, 148 pages.
Response to Office Action, submitted Oct. 15, 2012, in connection with Chinese Patent Application No. 200980118258.9, 17 pages.
Notice of Allowance, issued Nov. 7, 2012, in connection with Canadian Patent Application No. 2,718,231, 3 pages.
Decision to Grant, issued Nov. 8, 2012, in connection with European Patent Application No. 09722985.0, 2 pages.
Office communication, issued Nov. 14, 2012, in connection with U.S. Appl. No. 90/012,700, 3 pages.
Translation of Office Action, issued Nov. 15, 2012, in connection with Israeli Patent Application No. 208133, 3 pages.
Extended European Search Report, issued Dec. 5, 2012, in connection with European Patent Application No. 12188577.6, 7 pages.
Order Granting Request for Ex Parte Reexamination, issued Dec. 10, 2012, in connection with U.S. Appl. No. 90/012,700, 27 pages.
Restriction Requirement, issued Jan. 3, 2013, in connection with U.S. Appl. No. 13/134,927, 7 pages.
Response to Restriction Requirement, submitted Jan. 16, 2013, in connection with U.S. Appl. No. 13/134,927, 9 pages.
Office Action, issued Mar. 4, 2013, in connection with U.S. Appl. No. 90/012,700, 40 pages.
Office Action, issued Mar. 4, 2013, and translation, in connection with Chinese Patent Application No. 200980118258.9, 11 pages.
Response to Office Action, submitted Mar. 6, 2013, in connection with U.S. Appl. No. 13/065,510, 25 pages.
Response to Office Action, submitted Mar. 20, 2013, and instructions for response, in connection with Chinese Patent Application No. 200980118257.4, 17 pages.
Office Action, issued Mar. 26, 2013, in connection with with U.S. Appl. No. 13/134,927, 24 pages.
Office Action, issued Mar. 27, 2013, in connection with Mexican Patent Application No. MX/a/2010/010050, 9 pages.
Response to Office Action, submitted May 6, 2013, in connection with U.S. Appl. No. 90/012,700, 89 pages.
Response to Office Action, submitted May 15, 2013, in connection with Mexican Patent Application No. MX/a/2010/010050, 16 pages.
International Search Report and Written Opinion, issued May 29, 2013, in connection with International Patent Application No. PCT/US2013/025445, 11 pages.
U.S. Appl. No. 13/815,193, filed Feb. 8, 2013.
U.S. Appl. No. 90/012,700, filed Oct. 9, 2012.
U.S. Appl. No. 13/134,927, filed Jun. 20, 2011.
International Search Report and Written Opinion, issued Jul. 3, 2009, in connection with International Patent Application No. PCT/US2009/001775.
International Search Report and Written Opinion, issued Apr. 7, 2010, in connection with International Patent Application No. PCT/US2009/001774.
International Search Report and Written Opinion, issued Mar. 2, 2010 in connection with International Patent Application No. PCT/US2009/003761.

* cited by examiner

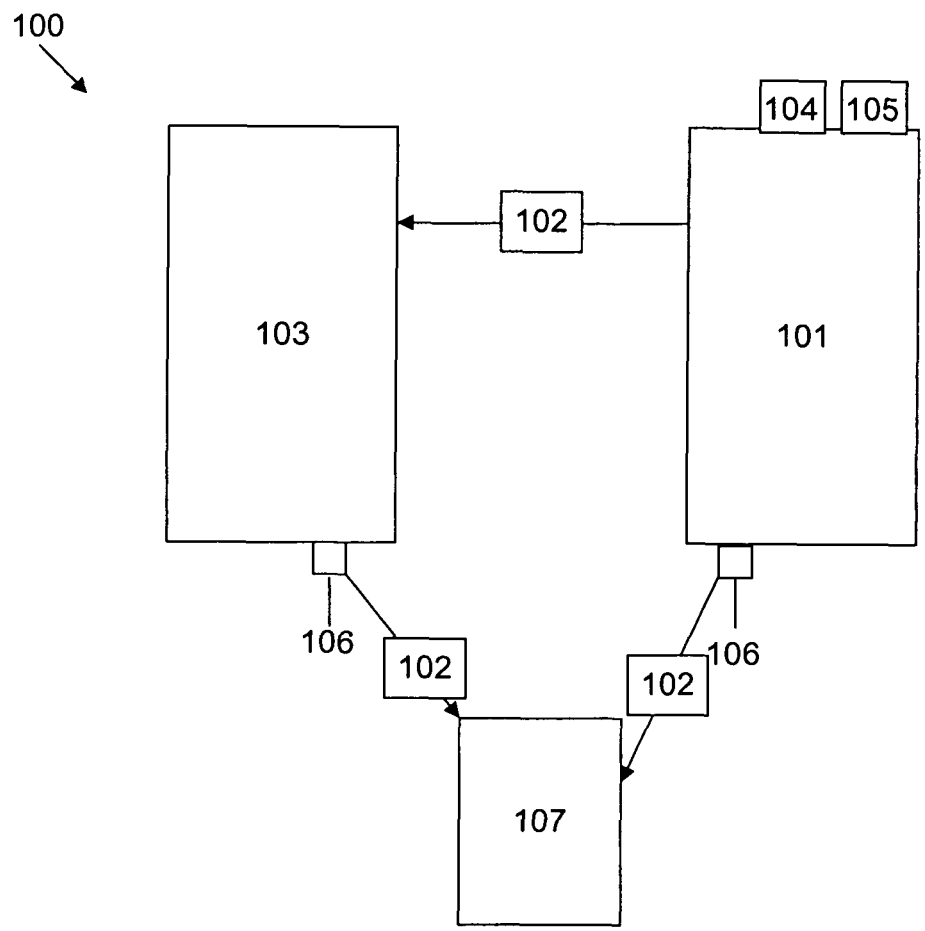

COMPOSITIONS CONTAINING NON-POLAR COMPOUNDS

RELATED APPLICATIONS

Benefit of priority is claimed under 35 U.S.C. §119(e) to U.S. Provisional Application Ser. No. 61/070,392, filed Mar. 20, 2008, entitled "COMPOSITIONS CONTAINING NON-POLAR COMPOUNDS," and U.S. Provisional Application Ser. No. 61/132,409, filed Jun. 16, 2008, entitled "COMPOSITIONS CONTAINING NON-POLAR COMPOUNDS," each to Philip Bromley.

This application is related to International Application No. PCT/US09/001,774, filed Mar. 20, 2009, entitled "COMPOSITIONS CONTAINING NON-POLAR COMPOUNDS," which also claims priority to U.S. Provisional Application Ser. Nos. 61/070,392 and 61/132,409. This application also is related to U.S. patent application Ser. No. 12/373,244, filed Mar. 20, 2009, entitled "COMPOSITIONS CONTAINING NON-POLAR COMPOUNDS" and International Application No. PCT/US09/001,775, filed Mar. 20, 2009, entitled "COMPOSITIONS CONTAINING NON-POLAR COMPOUNDS," which claim priority to U.S. Provisional Application Ser. No. 61/070,381, filed Mar. 20, 2008, entitled "COMPOSITIONS CONTAINING NON-POLAR COMPOUNDS," and U.S. Provisional Application Ser. No. 61/132,424, filed Jun. 16, 2008, entitled "COMPOSITIONS CONTAINING NON-POLAR COMPOUNDS," each to Philip Bromley.

The subject matter of each of the above-referenced applications is incorporated by reference in its entirety.

FIELD OF THE INVENTION

Provided are compositions and methods for preparing foods and beverages that contain additives, such as nutraceuticals, pharmaceuticals, and supplements, such as essential fatty acids, including omega-3 fatty acids, omega-6 fatty acids, conjugated fatty acids, and other fatty acids; phytochemicals, including phytosterols; other oils; and coenzymes, including Coenzyme Q10, and other oil-based additives.

BACKGROUND

Non-polar compounds are not easily dissolved in aqueous solutions, such as water. A number of non-polar compounds are used in compositions for human ingestion, for example, pharmaceuticals, nutraceuticals and/or dietary supplements. Exemplary of non-polar compounds used in such compositions are vitamins and minerals, fatty acids, and other non-polar compounds, non-polar active agents and non-polar active ingredients.

Because of poor water solubility, use of non-polar compounds in products for human consumption, for example, supplements, foods and beverages, often is challenging. Available compositions containing non-polar compounds, particularly aqueous compositions containing non-polar compounds, and methods for formulating such compositions, are limited. For example, methods and compositions for providing non-polar compounds in aqueous solutions, for example, in emulsions, are limited.

Thus, there remains a need to develop alternate compositions containing non-polar compounds and methods for making the compositions. Accordingly, it is among the objects herein to provide compositions, including solid and semi-solid compositions and aqueous compositions, containing non-polar compounds (e.g. non-polar active ingredients), and methods for making the compositions.

SUMMARY

Provided are first compositions (pre-emulsion compositions) that contain non-polar compounds. Typically, the first compositions are non-aqueous pre-emulsion compositions. Also provided are methods that use such first compositions to prepare other compositions, such as beverages and other aqueous liquids, into which the first compositions are diluted. Also provided are liquid dilution compositions containing the beverage or other aqueous liquid and the diluted pre-emulsion composition. The pre-emulsion compositions can be used to prepare dispersions, such as beverages, containing effective amounts of additives, such as non-polar compounds. The dispersions (e.g. liquid dilution compositions) can be used to provide an effective amount of the non-polar compounds, including non-polar active ingredients, such as nutraceuticals, pharmaceuticals, and supplements, such as essential fatty acids, including polyunsaturated fatty acids, such as omega-3 fatty acids, omega-6 fatty acids, conjugated fatty acids, and other fatty acids; phytochemicals, including phytosterols; other oils; and coenzymes, including Coenzyme Q10; and other oil-based additives. The amounts in the resulting diluted compositions are effective to supplement the diet. The compositions provided herein are and/or can be used to produce stable dispersions, without phase separation and other changes, such as particle formation, crystal formation and/or ringing.

The pre-emulsion compositions, for example, the non-aqueous pre-emulsion compositions, contain one or more surfactants (typically a surfactant that is a polyethylene glycol (PEG)-derivative of Vitamin E) and a non-polar compound (typically a non-polar active ingredient) other than the surfactant. In one example, where the pre-emulsion composition is a non-aqueous pre-emulsion composition, not more than 5% or about 5%, or not more than 1% or about 1%, by weight, of the composition, contains hydrophilic ingredient(s). Typically, the non-aqueous pre-emulsion composition has a waxy consistency.

In one embodiment, the amount of non-polar active ingredient is between 5% or about 5% and 35% or about 35%, for example, at or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35%, by weight, of the pre-emulsion composition and the amount of the surfactant is between 65% or about 65% and 95% or about 95%, for example, at or about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95%, by weight, of the pre-emulsion composition.

In one example, the amount of surfactant is between 69% or about 69% and 90% or about 90%, by weight, of the composition, for example, between 69% or about 69% and 80% or about 80%, by weight, or between 79% or about 79% and 90% or about 90%, by weight, of the composition, or 69.5% or about 69.5%, 79.5% or about 79.5%, or 89.5% or about 89.5%, by weight, of the composition.

In another example, the amount of the non-polar active ingredient is between 10% or about 10% and 30% or about 30%, between 20% or about 20% and 30% or about 30% or between 10% or about 10% and 20% or about 20%, by weight, of the composition, for example, at or about 10%, 20%, or 30%, by weight, of the composition.

In one example of this embodiment of the provided pre-emulsion compositions, where the amount of the surfactant is between 69% or about 69% and 80% or about 80%, by weight, of the composition, the non-polar active ingredient is between 20% or about 20% and 30% or about 30%, by weight, of the composition. In one embodiment, where the amount of the surfactant is between 79% or about 79% and 90% or about 90%, by weight, of the composition, the amount of the non-polar active ingredient is between 10% or about 10% and 20% or about 20%, by weight, of the composition.

In one example, the amount of surfactant is 69.5% or about 69.5%, by weight, of the composition and the amount of non-polar active ingredient is 30% or about 30%, by weight, of the composition; or the amount of surfactant is 79.5% or about 79.5%, by weight, of the composition and the amount of non-polar active ingredient is 20% or about 20%, by weight, of the composition; or the amount of surfactant is 89.5% or about 89.5%, by weight, of the composition and the amount of non-polar active ingredient is 10% or about 10%, by weight, of the composition.

In another embodiment of the provided pre-emulsion compositions, the further contains at least one additional non-polar active ingredient. In one example of this embodiment, the combined weight of the non-polar active ingredient and the at least one additional active ingredient is less than 30% or about 30%, or less than 50% or about 50%, of the weight of the non-aqueous pre-emulsion composition.

In another embodiment, the provided pre-emulsion composition contains a non-polar active ingredient at an amount between 5% or about 5% and 15% or about 15%, by weight, of the pre-emulsion composition, and a surfactant at an amount of between 40% or about 40% and 60% or about 60%, by weight, of the pre-emulsion composition. In one aspect of this embodiment, the non-polar active ingredient contains a phytosterol. In one example of this embodiment, the amount of the surfactant is between 49% or about 49% and 55% or about 55%, by weight, of the pre-emulsion composition. In one example of this embodiment, the pre-emulsion composition further contains one or more solvent one or more additional non-polar active ingredients, or a combination thereof. Exemplary of the one or more solvents, one or more additional non-polar active ingredients, and/or combinations thereof are compounds selected from among any one or more of Vitamin E oil, flaxseed oil, CLA and safflower oil.

In one embodiment, the provided pre-emulsion composition consists essentially of the non-polar active ingredient and the surfactant. In other embodiments, the pre-emulsion composition consists essentially of the non-polar active ingredient, the surfactant and a preservative. In another embodiment, the pre-emulsion composition consists essentially of the non-polar active ingredient, the surfactant, a preservative, and a solvent.

Typically, the surfactant(s) in the provided pre-emulsion compositions has an HLB value of between 14 or about 14 and 20 or about 20, for example, at or about 14, 15, 16, 17, 18, 19 or 20, typically between 16 or about 16 and 18 or about 18. Exemplary surfactants include, but are not limited to, Vitamin E-derived surfactants, such as tocopherol and/or tocotrienol-derived surfactants, in which the Vitamin E moiety represents the hydrophobic region of the surfactant, and is attached, via a linker, to another moiety, such as a polyethylene glycol (PEG) moiety. Exemplary of the Vitamin-E derived surfactants that can be used in the pre-emulsion compositions include, but are not limited to, tocopherol derived surfactants, including polyalkylene glycol derivatives of tocopherol, typically polyethylene glycol (PEG) derivatives of tocopherol, such as tocopherol polyethylene glycol succinate (TPGS), TPGS analogs, TPGS homologs and TPGS derivatives. Alternatively, the surfactants can be other PEG derivatives having similar properties, for example, PEG derivatives of sterols, e.g. a cholesterol or a sitosterol (including, for example, any of the PEG derivatives disclosed in U.S. Pat. No. 6,632,443) or PEG-derivatives of other fat-soluble vitamins, for example, some forms of Vitamin A (e.g. Retinol) or Vitamin D (e.g. Vitamin D1-D5).

An exemplary surfactant that can be used in any of the provided pre-emulsion compositions is a polyethylene glycol (PEG)-derivative of Vitamin E, for example, a tocopherol polyethylene glycol diester (TPGD). In one embodiment, the TPGD is selected from among tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol and tocopherol phthalate polyethylene glycol. In one embodiment, the surfactant is a tocopherol polyethylene glycol succinate (TPGS), such as a TPGS-1000 and/or a d-α TPGS. In another embodiment, the surfactant is a TPGS analog. In one aspect, the surfactant is a TPGS homolog, such as, for example, a TPGS homolog that differs from a TPGS parent compound by the addition or removal of one or more methylene unit(s), e.g., $-(CH_2)_n-$.

In some embodiments of the provided pre-emulsion compositions, the PEG moiety in the PEG-derivative of Vitamin E surfactant is selected from among any one or more of methylated PEG (m-PEG), PEG-OH, PEG-NHS, PEG-aldehyde, PEG-SH, PEG-NH$_2$, PEG-CO$_2$H, methylated PEGS and branched PEGs. In some embodiments, the PEG moiety in the surfactant has a molecular weight of between 200 or about 200 to 20,000 or about 20,000 Da, between 200 or about 200 and 6000 or about 6000 Da, between 600 or about 600 Da and 6000 or about 6000 Da, between 200 or about 200 Da and 2000 or about 2000 Da, between 600 or about 600 Da and 1500 or about 1500 Da, or between 600 or about 600 and 1000 or about 1000 Da.

Exemplary of non-polar compounds that can be included in any of the provided pre-emulsion compositions are non-polar active ingredients. Exemplary non-polar active ingredients include, but are not limited to omega-3 fatty acids, omega-6 fatty acids, conjugated fatty acids, Coenzyme Q10 (e.g. ubidecarenone), phytosterols and saw palmetto extracts, such as, for example, fish oil, algae oil, flaxseed oil, GLA (e.g. borage oil) and CLA.

Also exemplary of the non-polar active ingredients include, but are not limited to, compounds containing any fat-soluble nutraceutical or pharmaceutical and/or oil, such as, for example, drugs, hormones, vitamins, nutrients, including any and other lipophilic compounds containing essential fatty acids, for example, polyunsaturated fatty acids (PUFAs), including, for example, omega-3 fatty acids, for example, natural and synthetic omega-3 fatty acids, for example, compounds containing omega-3 polyunsaturated long-chain fatty acids, including Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3ω3; 24:5ω3 and/or nisinic acid (24:6ω3), for example, fish oil, algae oil, krill oil, canola oil, flaxseed oil, soybean oil and walnut oil; compounds containing short-chain omega-3 fatty acids, for example, Alpha-Linolenic acid (α-Linolenic acid; ALA) (18:3ω3) (e.g. flaxseed oil) and Stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), for example, highly purified fish oil concentrates, *perilla* oil, krill oil, and algae oil, for example, microalgae oil; compounds containing omega 6 fatty acids, for example, compounds containing Linoleic acid (18:2ω6) (a short-chain fatty acid); Gamma-linolenic acid (GLA) (18:3ω6); Dihomo gamma linolenic acid (DGLA) (20:3ω6); Eicosadienoic:acid (20:2ω6); Arachidonic acid (AA) (20:4ω6); Docosadienoic acid (22:2ω6); Adrenic acid (22:4ω6); and/or Docosapentaenoic acid (22:5ω6), for example, borage oil, corn oil, cottonseed oil, grapeseed oil, peanut oil, primrose oil, for example, evening primrose *Oenothera biennis*) oil, blackcurrant seed oil, hemp seed oil, spurulina extract, safflower oil, sesame oil and soybean oil;

compounds containing other fatty acids, for example, triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; and ethyl linoleate; and herb oils, for example, garlic oils and scordinin; short-chain saturated fatty acids (4:0-10:0), Lauric acid (12:0), Myristic:acid (14:0), Pentadecanoic acid (15:0), Palmitic acid (16:0), Palmitoleic acid (16:1 ω7), Heptadecanoic acid (17:0), Stearic acid (18:0), Oleic acid (18:1 ω9), Arachidic:acid (20:0);

compounds containing micronutrients, for example, vitamins, minerals, co-factors, for example, coenzymes, such as coenzyme Q, e.g. Coenzyme Q10 (CoQ10, also called ubiquinone, e.g. ubidecarenone or a reduced form of CoQ10, e.g. ubiquinol), tumeric extract (cucuminoids), saw palmetto lipid extract (saw palmetto oil), echinacea extract, hawthorne berry extract, ginseng extract, lipoic acid (thiotic acid), acsorbyl palmitate, kava extract, St. John's Wort (hypericum, Klamath weed, goat weed), extract of quercitin, dihydroepiandrosterone, indol-3-carbinol;

compounds containing carotenoids, including hydrocarbons and oxygenated, alcoholic derivatives of hydrocarbons, for example, beta carotene, mixed carotenoids complex, leutein, lycopene, Zeaxanthin, Cryptoxanthin, for example, beta-crytoxanthin, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, esters of hydroxyl- or carboxyl-containing members thereof;

compounds containing fat-soluble vitamins, for example, Vitamins A, D, E and K, and corresponding provitamins and vitamin derivatives such as esters with an action resembling that of vitamin A, D, E or K for example; retinol (vitamin A) and pharmaceutically acceptable derivatives thereof, for example, palmitate ester of retinol and other esters of retinol, and calciferol (vitamin D) and its pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

compounds containing phytochemicals, including phytoestrogens, for example, genistein and daidzein, for example, isoflavones, for example, soy isoflavones, flavonoids, phytoalexins, for example, Resveratrol (3,5,4'-trihydroxystilbene), red clover extract, and phytosterols;

compounds containing lipid-soluble drugs, including natural and synthetic forms of immunosuppressive drugs, such as Cyclosporin, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepinadrosterone (DHEA), growth hormones and other hormones;

compounds containing oil-soluble acids and alcohols, for example, tartaric acid, lactylic acid butylated hydroxyanisole, butylated hydroxytoluene, lignin, sterols, polyphenolic compounds, oryzanol, cholesterol, phytosterols, flavonoids, such as quercetin and reservatol, diallyl disulfides and the like.

In some embodiments, the non-polar active ingredient includes one or more of polyunsaturated fatty acids, such as compounds including any one or more of omega-3 fatty acids, including Docosahexaenoic acid (DHA), eicosapentaenoic acid (EPA) and alpha-linolenic acid (ALA) (for example, fish oils, krill oils, algae oils and/or flaxseed oils); omega-6 fatty acids, such as gamma-linolenic acid (GLA) (e.g. borage oils); conjugated fatty acids (e.g. conjugated linolenic acid (CLA)); and saw palmetto extracts. In other embodiments, the non-polar active ingredients include compounds containing coenzymes, typically coenzyme Q, for example, Coenzyme Q10, e.g. ubidecarenone, and/or compounds containing phytosterols.

In any of the provided pre-emulsion compositions, the non-polar active ingredient contains EPA, DHA or a combination thereof. In one aspect, the non-polar active ingredient contains DHA, at an amount between 20% or about 20% and 90% or about 90% or between 25% or about 25% and 85% or about 85%; or between 35% or about 35% and 70% or about 70%, or between 25% or about 25% and 40% or about 40%, by weight, of the non-polar active ingredient. In another aspect, the non-polar active ingredient contains EPA, at an amount between 5% or about 5% and 15% or about 15%, between 5% or about 5% and 13% or about 13%, or between 5% or about 5% and 10% or about 10% by weight, of the non-polar active ingredient. In one aspect, the amount of EPA is not more than 10% or about 10%, or not more than 13% or about 13%, by weight, of the non-polar active ingredient. In exemplary embodiments, the non-polar active ingredient is a fish oil or an algae oil.

In one embodiment, the non-polar active ingredient contains ALA, at an amount of at least 50% or about 50%, by weight, of the non-polar active ingredient, such as between 50% or about 50% and 80% or about 80%, or between 65% or about 65% and 75% or about 75%, by weight, of the non-polar active ingredient. Exemplary of such an embodiment is a pre-emulsion composition containing a flaxseed oil.

In another embodiment, the non-polar active ingredient contains GLA at an amount of at least 22% or about 22%, by weight, of the non-polar active ingredient, for example, in a borage oil.

In some embodiments, the pre-emulsion compositions contain more than one non-polar active ingredient, for example, two or more non-polar active ingredients where the total amount of non-polar active ingredient is between at or about 5% and 35% of the weight of the pre-emulsion composition, or between at or about 5% and 15% of the pre-emulsion composition, for example, where the combined weight of the non-polar active ingredient and additional non-polar active ingredient(s) is less than at or about 35%, 30%, or 15%, by weight, of the pre-emulsion composition.

The provided pre-emulsion compositions further can contain one or more additional ingredients. In one embodiment, the compositions further comprise one or more preservative, in an amount sufficient to preserve the composition. Exemplary of the preservatives are natural preservatives, such as benzyl alcohol and preservatives containing benzyl alcohol. In one embodiment, the amount of preservative is between 0.1% or about 0.1% and 1% or about 1%, by weight, of the pre-emulsion composition, for example, at or about 0.1, 0.2, 0.3, 0.4, 0.5, 0.6, 0.7, 0.8, 0.9 or 1%, by weight of the composition. In one example, the amount of benzyl alcohol is between 0.1% or about 0.1% and 1% or about 1%, by weight, of the pre-emulsion composition, for example, at or about 0.1, 0.2, 0.3, 0.4, 0.5, 0.6, 0.7, 0.8, 0.9 or 1%, by weight of the pre-emulsion composition.

In another embodiment, the one or more additional ingredients includes a solvent that dissolves the non-polar active ingredient and differs therefrom. In one example, the amount of solvent is sufficient to dissolve the non-polar active ingredient. Exemplary of the solvents are oils. The solvent(s) can include any oil suitable for dissolving the non-polar ingredient. Exemplary of the solvents are Vitamin E oil, flaxseed oil, sunflower oil, any vegetable oil or other oil. In one embodiment, the amount of solvent in the concentrate is between 1% or about 1% and 6% or about 6%, for example, at or about 1, 2, 3, 4, 5, or 6%, by weight, of the composition.

In another embodiment, the one or more additional ingredients includes one or more emulsion stabilizers. Typically, the emulsion stabilizer is included in the composition at an amount sufficient to stabilize the composition. Exemplary of an emulsion stabilizer is a composition containing a blend of gums, such as the Saladizer® brand emulsion stabilizer. In one embodiment, the emulsion stabilizer contains one or more of guar gum, xanthan gum and sodium alginate. In one example, the emulsion stabilizer contains guar gum, xanthan gum and sodium alginate.

In another embodiment, the one or more additional ingredients include one or more co-surfactants. In one example, the co-surfactant is included in the pre-emulsion composition in an amount sufficient to stabilize the composition. In one aspect, the co-surfactant is a phospholipid, such as, but not limited to, a phosphatidylcholine. In one example, the amount of the co-surfactant, e.g. the phospholipid, is between 0.1% or about 0.1% and 1% or about 1%, by weight, of the concentrate.

In another embodiment, the one or more additional ingredients includes one or more flavors. In one example, the flavor is included in the composition at an amount sufficient to enhance the taste of the composition, the smell of the composition, or a combination thereof. Exemplary flavors include, but are not limited to, lemon oil, D-limonene, or a combination thereof, or any other known flavors, such as flavors described herein.

Also exemplary of the additional ingredients that can be included in the provided compositions are one or more pH adjusters. Typically, the pH adjuster contains an acid or a base at an amount sufficient to affect the pH of the compositions. Exemplary of the pH adjusters are citric acid and phosphoric acid.

In some embodiments, the pre-emulsion composition is formulated based on the properties of dilution compositions that can be generated by diluting the pre-emulsion composition in an aqueous liquid. Typically, the pre-emulsion composition is formed so that it can be diluted in aqueous medium to produce a liquid dilution composition having one, more than one, all, or any combination of, of the following properties:

In one embodiment, the pre-emulsion composition is formulated such that: dilution of at least 0.5 g or about 0.5 g, at least 1 g or about 1 g, at least 2 g or about 2 g, at least 5 g or about 5 g, or at least 10 g or about 10 g of the pre-emulsion composition into at or about 8 fluid ounces (0.236588 liters) of an aqueous medium; or dilution of the pre-emulsion composition in an aqueous medium, at a dilution of not more than 1:10 or about 1:10, not more than 1:25 or about 1:25, not more than 1:50 or about 1:50, not more than 1:100 or about 1:100, not more than 1:250 or about 1:250 or not more than 1:500, yields a liquid dilution composition having a particle size of less than 500 or less than about 500, less than 300 or less than about 300 or less than 200 nm or less than about 200 nm, on the average or at the most.

In one embodiment, the liquid dilution composition that is formed by dilution of the pre-emulsion composition into aqueous medium has a particle size of less than 500 or less than about 500, less than 300 or less than about 300 or less than 200 nm or less than about 200 nm, on the average or at the most, and contains at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In some aspects of these embodiments, the resulting liquid dilution composition that is formed by diluting the pre-emulsion composition has a particle size of less than 100 nm or about 100 nm, less than 50 nm or about 50 nm, less than 25 nm or about 25 nm, less than 15 nm or about 15 nm or less than 10 nm or about 10 nm, on average or at the most.

In another embodiment, the pre-emulsion composition is formulated such that dilution of at least 0.5 g or about 0.5 g, at least 1 g or about 1 g, at least 2 g or about 2 g, at least 5 g or about 5 g, or at least 10 g or about 10 g of the pre-emulsion composition into 8 or about 8 fluid ounces of an aqueous medium; or dilution of the concentrate in an aqueous medium, at a dilution not more than 1:10 or about 1:10, not more than 1:25 or about 1:25, not more than 1:50 or about 1:50, not more than 1:100 or about 1:100, not more than 1:250 or about 1:250 or not more than 1:500, yields a liquid dilution composition having a Nephelometric Turbidity Units (NTU) value of less than 500 or about 500, less than 300 or about 300, or less than 200 or about 200. In one aspect, the NTU value of the resulting dilution composition is less than 100 or about 100, less than 50 or about 50, less than 30 or about 30, less than 25 or about 25, or less than 10 or about 10.

In another embodiment, the liquid dilution composition formed by dilution of the pre-emulsion composition into aqueous medium has an NTU value of less than 500 or about 500, less than 300 or about 300, or less than 200 or about 200 and contains at least 25 mg or about 25 mg, at least 35 mg or about 35 mg, at least 50 mg or about 50 mg, at least 100 mg or about 100 mg, at least 250 mg or about 250 mg, or at least 500 mg or about 500 mg of the non-polar active ingredient per 8 fluid ounces of the liquid dilution composition.

In some aspects of these embodiments, the NTU value is less than 100 or about 100, less than 50 or about 50, less than 30 or about 30, less than 25 or about 25, or less than 10 or about 10.

In another embodiment, the pre-emulsion composition is formulated such that dilution of at least 0.5 g or about 0.5 g, at least 1 g or about 1 g, at least 2 g or about 2 g, at least 5 g or about 5 g, or at least 10 g or about 10 g of the pre-emulsion composition into 8 or about 8 fluid ounces of an aqueous medium; or dilution of the pre-emulsion composition in an aqueous medium, at a dilution not more than 1:10 or about 1:10, not more than 1:25 or about 1:25, not more than 1:50 or about 1:50, not more than 1:100 or about 1:100, not more than 1:250 or about 1:250 or not more than 1:500, yields a liquid dilution composition that does not contain visible particles, does not contain visible crystals, does not exhibit ringing and/or does not exhibit phase separation; and/or remains free from (or does not exhibit) visible particles, visible crystals, ringing and/or phase separation when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one embodiment, the pre-emulsion composition is formulated such that dilution of at least 0.5 g or about 0.5 g, at least 1 g or about 1 g, at least 2 g or about 2 g, at least 5 g or about 5 g, or at least 10 g or about 10 g of the pre-emulsion composition into 8 or about 8 fluid ounces of a beverage; or dilution at not more than 1:10 or about 1:10, not more than 1:25 or about 1:25, not more than 1:50 or about 1:50, not more than 1:100 or about 1:100, not more than 1:250 or about 1:250 or not more than 1:500 into a beverage, yields a liquid dilution composition that is at least as clear as, or substantially as clear as, the beverage, and/or remains as clear as, or substantially as clear as, the beverage when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

Also provided are liquid dilution compositions, which contain the pre-emulsion compositions diluted in an aqueous medium. Exemplary of the aqueous medium are beverages, such as, for example, water, juice, soda, tea, coffee, sports drinks, nutritional beverages, energy drinks, milk, and other beverages. The provided liquid dilution compositions are liquid dilution compositions containing any one or more of the provided pre-emulsion compositions. Typically, the provided liquid dilution compositions are compositions containing the pre-emulsion composition(s) and having any one or more of the properties of the desired liquid dilution compositions described above.

For example, in one embodiment, the provided liquid dilution composition contains a particle size less than 500 or about 500, less than 300 or about 300, less than 200 or about 200 nm, less than 100 or about 100 nm, less than 50 or about 50 nm or less than 25 or about 25 nm, on the average or at the most. In another embodiment, the liquid dilution composition has an NTU value less than 200 or about 200, less than 100 or about 100, less than 50 or about 50, less than 25 or about 25, or less than 10 or about 10. In one example, the liquid dilution composition does not contain visible particles, does not contain visible crystals, does not exhibit ringing and/or does not exhibit phase separation; and/or remains free from (or does not exhibit) visible particles, visible crystals, ringing and/or phase separation when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one example, the aqueous medium contained in the liquid dilution composition is a beverage, such as, for example, water, soda, milk, tea, coffee, juice, energy drink or a sports or nutrition beverage. In one aspect, the liquid dilution composition is as clear or about as clear as the beverage prior to addition of the pre-emulsion composition, and/or remains as clear or about as clear as the beverage when stored at room temperature (e.g. 25° C. or about 25° C.), or at a refrigerated temperature (e.g. 0-10° C. or about 0-10° C., e.g. at or about 4° C.), or at a frozen temperature (e.g. −20° C. or about −20° C.), wherein the storage is for at least one day, at least one week, at least thirty days, or at least one year.

In one embodiment, the dilution factor at which the pre-emulsion composition is diluted in the aqueous medium is not more than 1:10 or about 1:10, not more than 1:25 or about 1:25, not more than 1:50 or about 1:50, not more than 1:100 or about 1:100, not more than 1:250 or about 1:250 or not more than 1:500. In another embodiment, the concentrate is diluted in the aqueous medium to form the liquid dilution composition at 0.5 g or about 0.5 g, at least 1 g or about 1 g, at least 2 g or about 2 g, at least 5 g or about 5 g, or at least 10 g or about 10 g of the concentrate into 8 or about 8 fluid ounces of the aqueous medium. In another embodiment, the liquid dilution composition contains at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In one embodiment, the liquid dilution composition does not contain visible particles; and/or remains free from visible particles when stored at room temperature, or at a refrigerated temperature, or at a frozen temperature, wherein the storage is for at least one day, at least one week, at least thirty days, or at least one year; and/or does not contain visible crystals, for example, remains free from visible crystals when stored at room temperature, or at refrigerated temperature, or at a frozen temperature, wherein the storage is for at least one day, at least one week, at least thirty days, or at least one year; and/or does not exhibit ringing, for example, remains free from ringing when stored at room temperature, at a refrigerated temperature, or at a frozen temperature, wherein the storage is for at least one day, at least one week, at least thirty days, or at least one year; or does not exhibit phase separation, for example, does not exhibit phase separation when stored at room temperature, refrigerated temperature or frozen temperature, wherein the storage is for at least one day, at least one week, at least thirty days, or at least one year.

Also provided are methods for making the pre-emulsion compositions. The methods can be used to produce any of the pre-emulsion compositions provided herein. In general, the methods for making the pre-emulsion compositions are carried out by heating ingredients and mixing (e.g. homogenizing) the ingredients, and then cooling the mixed ingredients, whereby the mixture becomes waxy in consistency. In one example, the mixture that is waxy in consistency is the pre-emulsion concentrate. In another example, additional steps can include adding one or more flavors or other ingredients, to form the final pre-emulsion composition.

In one example of the methods, initial ingredients are mixed and heated in a vessel; one or more additional ingredients are added to the vessel; the ingredients are homogenized, and the mixed ingredients are cooled, whereby the mixture becomes waxy in consistency, thereby generating the pre-emulsion composition.

In one embodiment, the initial ingredients include a surfactant, such as any of the surfactant of the provided pre-emulsion compositions as described above, for example, a PEG-derivative of Vitamin E, such as a TPGD, e.g. a TPGS or a TPGS analog (such as a TPGS homolog); and the one or more additional ingredients include a non-polar active ingredient, such as any of the non-polar active ingredient in any of the pre-emulsion concentrates provided herein.

In another embodiment, the initial ingredients include a non-polar active ingredient, such as any of the non-polar active ingredient in any of the pre-emulsion concentrates provided herein (e.g. a phytosterol-containing non-polar active ingredient); and the one or more additional ingredients include a surfactant, such as any of the surfactant of the provided pre-emulsion compositions as described above, e.g. a PEG-derivative of Vitamin E, such as a TPGD, e.g. a TPGS or a TPGS analog (such as a TPGS homolog).

The amounts of the surfactant(s) and non-polar active ingredient(s) that are added in the methods are selected based on the appropriate concentration ranges of these ingredients in the final resulting pre-emulsion composition. For example, in one embodiment, the non-polar active ingredient is added at an amount that is between 5% or about 5% and 15% or about 15%, by weight, of the pre-emulsion composition. In another embodiment, the non-polar active ingredient is added at an amount that is between 5% or about 5% and 35% or about 35%, by weight, of the pre-emulsion composition, or at any of the concentrations of these ingredients provided herein.

In one embodiment, the surfactant(s) is added at an amount that is between 40% or about 40% and 60% or about 60%, by weight, of the pre-emulsion composition. In another embodiment, the surfactant is added at an amount that is between 65% or about 65% and 95% or about 95%, by weight, of the pre-emulsion composition, or any of the concentrations of the surfactant provided herein.

In one embodiment, the ingredients (e.g. the first ingredients, the one or more additional ingredients or a combination thereof) further include a solvent that dissolves the non-polar active ingredient and differs therefrom. In one example, the amount of solvent is sufficient to dissolve the non-polar active ingredient, for example, while heating the ingredients. Exemplary solvents include solvents containing any one or more of a Vitamin E oil, a flaxseed oil, a CLA and a safflower oil, or a combination thereof. In another embodiment, the ingredients further include one or more additional ingredients selected from among solvents, additional non-polar active ingredients, or combinations thereof, such as, for example, Vitamin E oil, flaxseed oil, CLA and safflower oil.

In one example, the solvent, additional non-polar active ingredient(s) and/or combination thereof, is added at an amount that is between 1% or about 1% and 6% or about 6% of the pre-emulsion composition. In another example, the solvent is included at an amount that is between 1% or about 1% and 15% or about 15%, for example, at or about 1, 2, 3, 4, 5, 6, 7, 8, 9, 10, 11, 12, 13, 14 or 15%, by weight, of the pr-emulsion composition.

In another embodiment, the ingredients further comprise a co-surfactant, at an amount sufficient to stabilize the composition. In one example, the co-surfactant contains a phospholipid, such as a co-surfactant containing a phosphatidylcholine. In one aspect, the phospholipid is added at an amount that is between 0.1% or about 0.1% and 1% or about 1%, by weight, of the pre-emulsion composition.

In another embodiment, the ingredients further comprise at least one preservative, such as benzyl alcohol or a preservative containing benzyl alcohol. In one example, the preservative is added at an amount sufficient to preserve the composition, for example at an amount that is between 0.1% or about 0.1% and 1% or about 1%, by weight, of the composition.

In another embodiment, the ingredients further comprise an emulsion stabilizer. In one example, the emulsion stabilizer is added at an amount sufficient to stabilize the composition. In one example, the emulsion stabilizer comprises a blend of gums, such as a blend selected from among any one or more of guar gum, xanthan gum and sodium alginate.

In another embodiment, one or more additional ingredients are added after mixing and heating the ingredients and/or after cooling or partially cooling the ingredients. Exemplary of such additional ingredients are one or more flavors, for example, flavors added at an amount sufficient to enhance the taste of the composition, the smell of the composition, or a combination thereof. Exemplary flavors are lemon oil and/or D-limonene, or any of the flavors described herein. Other additional ingredients include, but are not limited to, pH adjusters, which typically are added at an amount sufficient to affect the pH of the composition, for example, a pH adjuster containing an acid or base at an amount to affect the pH of the composition. Exemplary pH adjusters are compounds containing citric acid or phosphoric acid or a combination thereof.

The mixing and heating steps can be carried out using any mixing and heating methods. In one example, the mixing is carried out with a standard mixer. In another example, the heating is carried out with a heating apparatus, such as, for example, a water-jacket, for example on a water-jacketed tank. In one embodiment, heating the ingredients comprises heating the ingredients to 60° C. or about 60° C. In one example, the homogenizing is carried out with a reversible homogenizer. In one example, the homogenizing is carried out at between 850 or about 850 rpm and 1200 or about 1200 rpm.

In one example, the methods for producing the pre-emulsion compositions are carried out using a bench-top process, as described herein below. In another example, the methods are performed using a scaled-up process, as described herein below. For example, the methods can be performed using a scaled-up process such as the one illustrated in FIG. 1.

In this example, the initial ingredients are added and mixed in a mixing tank and mixed using a standard mixer, attached to the tank, for example, mounted on the top of the tank. The ingredients are mixed and heated, typically to low heat (e.g. 60° C.), until dissolved, according to the provided methods. Once the initial ingredients are dissolved (by heating and mixing with the standard mixer) additional ingredient(s) are added, and the mixture is homogenized. To begin the homogenization step, a homogenizer mounted on the mixing tank is turned on, for example, at 850-1200 rpm. The additional ingredient(s) is added and the mixture homogenized, typically while continuing to heat the mixture, e.g. while maintaining low heat. The homogenization is continued, with heating, until the ingredients dissolve. After the homogenization step, one or more additional steps can be carried out. In one example (shown on the left hand side), the ingredients are transferred, via transfer means to a packaging or holding tank. Typically, the pre-emulsion composition is filtered using an end-product filter such as a 100 micron end-product filter. The composition finally is transferred, for example, using transfer means, to a storage container. Typically, the composition is transferred into the storage container while it is still at a heated temperature, for example, between 48° C. or about 48° C. and 60° C. or about 60° C. In this example, the composition then solidifies (developing a waxy consistency) while in the storage container. In other examples, the methods include variations of this exemplary scaled-up process using the provided methods, to make the pre-emulsion compositions.

Also provided are methods of diluting the pre-emulsion compositions, e.g. in aqueous media such as beverages, to form the provided liquid dilution compositions. Exemplary of such methods are methods for providing an oil-based additive, such as any one or more of the non-polar active ingredients described herein. In one embodiment of the methods, one or more of the pre-emulsion compositions provided herein is added to aqueous medium, for example, a beverage. In one example, the pre-emulsion composition is added to the aqueous medium (e.g. beverage) at an amount effective to deliver an effective amount of the additive (e.g. non-polar active ingredient).

In one embodiment of the methods the aqueous medium is heated, for example, to at least 40° C. or at least about 40° C., for example, 41, 42, 43, 44, 45, 46, 47, 48, 49, 50 or more ° C., for example, 48.9° C. (120° F. or about 120° F.), prior to, subsequent to, or simultaneous with the addition of the pre-emulsion composition. In one such example, the pre-emulsion composition is added, at an appropriate dilution, as described herein, to the heated aqueous medium, and mixed (e.g. stirred) until dispersed or dissolved in the solution. In one example, the pre-emulsion composition is heated before addition to the aqueous medium, for example, to at least 40° C. or at least about 40° C., for example, 41, 42, 43, 44, 45, 46, 47, 48, 49, 50 or more ° C., for example, 48.9° C. (120° F. or about 120° F.). In another example, the pre-emulsion composition is added to the medium without heating.

In one embodiment, the methods further include cooling the resulting liquid dilution composition, for example, to room temperature, for example, 25° C. or about 25° C.

In one embodiment, the methods further include packaging the aqueous liquid dilution composition, for example, by transferring to containers, such as vials or beverage containers. In one example, a portion of the liquid dilution composition is transferred to vials for analysis, for example, evaluation of properties, such as clarity, turbidity, taste, smell, ringing, crystal formation and/or other properties.

Typically, the pre-emulsion composition is added to the medium, e.g. beverage, such that the medium contains an effective amount of the additive (e.g. the non-polar active ingredient).

The effective amount of the additive, such as the non-polar active ingredient is the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, the pre-emulsion composition is added to the aqueous medium such that the resulting liquid dilution composition contains an effective amount of a particular non-polar compound, for example, a particular amount per volume or weight of the composition, such as, for example, at least 25 mg or about 25 mg, at least 35 mg or about 35 mg, at least 50 mg or about 50 mg or at least 100 mg or about 100 mg, at least 250 mg or about 250 mg, or at least 500 mg or about 500 mg of the non-polar active ingredient per 8 fluid ounces of the liquid dilution composition.

In one example, an effective amount is a concentration or amount of the pre-emulsion composition where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces of the aqueous medium.

BRIEF DESCRIPTION OF THE DRAWINGS

FIG. 1

FIG. 1 sets forth a an exemplary scaled-up process 100 for carrying out the provided methods for making the pre-emulsion compositions. In this example of the scaled-up process, the initial ingredients are added and mixed in a mixing tank 101 and mixed using a standard mixer 104, for example, a LIGHTNIN® mixer (for example, model no. XJC117, a fixed-mount gear drive high-flow mixer), attached to the tank, for example, mounted on the top of the tank. The ingredients are mixed and heated, typically to low heat (e.g. 60° C.), until dissolved, according to the provided methods. Once the initial ingredients are dissolved (by heating and mixing with the standard mixer) additional ingredient(s) are added, and the mixture is homogenized. To begin the homogenization step, a homogenizer 105 (e.g. an Arde Barinco, Inc. reversible homogenizer), mounted on the mixing tank, is turned on, for example, at 850-1200 rpm. The additional ingredient(s) is added and the mixture homogenized, typically while continuing to heat the mixture, e.g. while maintaining low heat. The homogenization is continued, with heating, until the ingredients dissolve. After the homogenization step, one or more additional steps can be carried out. In one example (shown on the left hand side), the ingredients are transferred, via transfer means 102 to a packaging or holding tank 103. Typically, the pre-emulsion composition is filtered using an end-product filter 106, such as a 100 micron end-product filter. As shown, the composition can be filtered directly from the mixing tank 101 (as shown on the right), or it can be filtered after transfer to the packaging/holding tank 103 (as shown on the left). The composition finally is transferred, for example, using transfer means 102, to a storage container 107. Typically, the composition is transferred into the storage container while it is still at a heated temperature, for example, between 48° C. or about 48° C. and 60° C. or about 60° C. In this example, the composition then solidifies (developing a waxy consistency) while in the storage container. Variations of this exemplary scaled-up process (FIG. 1) also can be carried out using the provided methods, to make the pre-emulsion compositions.

DETAILED DESCRIPTION

| | | | |
|---|---|---|---|
| A. | DEFINITIONS | | 23 |
| B. | COMPOSITIONS CONTAINING NON-POLAR COMPOUNDS | | 55 |
| | 1. Pre-emulsion compositions containing the non-polar compounds | | 58 |
| | a. Formulating the pre-emulsion compositions | | 60 |
| | i. Common ingredients and typical concentration ranges | | 63 |
| | ii. Evaluation of the initial pre-emulsion composition | | 65 |
| | (1) Clarity | | 66 |
| | (2) Empirical evaluation | | 68 |
| | (3) Particle size | | 69 |
| | (4) Turbidity measurement | | 70 |
| | iii. Selecting a formulation and modifying formulations | | 71 |
| | b. Non-Polar Compounds | | 73 |
| | i. Polyunsaturated Fatty Acid (PUFA)-containing active ingredients | | 75 |
| | (1) Omega-3 fatty acid compounds | | 78 |
| | (a) DHA/EPA | | 78 |
| | (i) Fish Oils | | 79 |
| | (ii) Algae oil | | 81 |
| | (b) Flax Seed Oil - omega 3 (ALA) | | 82 |
| | (2) Omega-6 compounds | | 82 |
| | (a) Borage oil (Gamma-Linolenic Acid (GLA)) | | 83 |

-continued

| DETAILED DESCRIPTION | |
|---|---|
| (3) Saw Palmetto extract | 83 |
| (4) Conjugated Linoleic Acid (CLA) | 84 |
| ii. Coenzyme Q Active Ingredients | 85 |
| (1) Coenzyme Q10 | 85 |
| iii. Phytosterol-Containing Active Ingredients | 86 |
| c. Other components of the pre-emulsion compositions | 87 |
| i. Surfactants | 87 |
| ii. PEG-Derivatives of Vitamin E | 88 |
| (1) Tocopherols and Tocotrienols | 89 |
| (2) PEG moieties | 90 |
| (3) Linkers | 90 |
| (4) Tocopherol polyethylene glycol and Tocotrienol polyethylene glycol diesters (dicarboxylic acid esters of Vitamin E linked to PEG) | 91 |
| (5) Other Vitamin E PEG Esters | 92 |
| (a) TPGS Surfactants | 93 |
| iii. Concentration of the surfactant | 94 |
| iv. HLB | 95 |
| (1) TPGS | 96 |
| (2) Co-surfactants (emulsifiers) | 97 |
| (a) Phospholipids | 97 |
| v. Preservatives and Sterilizers | 98 |
| vi. Emulsion stabilizers (co-emulsifier) | 98 |
| vii. Solvents | 99 |
| viii. Flavors | 100 |
| ix. pH adjusters | 101 |
| 2. Powder | 101 |
| 3. Liquid dilution compositions containing the diluted pre-emulsion compositions | 105 |
| a. Clarity | 107 |
| i. Clarity determined by empirical evaluation | 108 |
| ii. Clarity determined by particle size or number of particles | 108 |
| iii. Turbidity | 109 |
| b. Stability | 110 |
| c. Desirable characteristics for human consumption | 111 |
| d. Safety | 112 |
| e. Oral bioavailability | 112 |
| C. METHODS FOR MAKING PRE-EMULSION COMPOSITIONS CONTAINING NON-POLAR COMPOUNDS | 112 |
| 1. Equipment for making the pre-emulsion compositions | 113 |
| a. Scales | 113 |
| b. Purifiers, including filters | 113 |
| c. Vessels for mixing the ingredients | 114 |
| d. Mixers | 115 |
| e. Heating apparatuses | 117 |
| f. Cooling apparatuses | 118 |
| g. Transfer means | 119 |
| h. Evaluation equipment | 119 |
| 2. General methods for making the pre-emulsion compositions | 120 |
| a. Combining the ingredients | 121 |
| i. Weighing the ingredients | 121 |
| ii. Dissolving first ingredient(s) - standard mixer | 121 |
| iii. Homogenizing the mixture | 122 |
| iv. Ingredients and order of addition | 123 |
| b. Additional steps | 124 |
| i. Additional ingredients | 124 |
| ii. Evaluation of the pre-emulsion composition | 125 |
| iii. Filtering | 125 |
| iv. Transfer and/or packaging | 125 |
| 3. Bench-top process | 126 |
| 4. Scaled-up manufacturing process | 127 |
| a. Combining the ingredients | 128 |
| i. Dissolving the initial ingredients - standard mixing | 128 |
| ii. Addition of the non-polar compound and homogenizing | 128 |
| b. Additional steps | 129 |
| D. METHODS FOR MAKING THE LIQUID DILUTION COMPOSITIONS CONTAINING THE DILUTED PRE-EMULSION COMPOSITIONS | 129 |
| 1. Dilutions | 131 |
| 2. Analyzing the aqueous liquid dilution compositions containing the liquid pre-emulsion compositions | 132 |
| a. Clarity/turbidity | 132 |
| i. Empirical evaluation | 133 |
| ii. Particle size | 133 |
| iii. Turbidity measurement | 134 |
| E. EXAMPLES | 134 |

A. Definitions

Unless defined otherwise, all technical and scientific terms used herein have the same meaning as is commonly understood by one of skill in the art to which the invention(s) belong. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, colloid refers to a mixture containing two phases, a dispersed phase and a continuous phase, the dispersed phase containing particles (droplets) distributed throughout the continuous phase. Colloidal mixtures include aerosols, foams and dispersions, for example, emulsions, for example, nanoemulsions. A liquid colloid, for example, a nanoemulsion, can have a similar appearance, for example, clarity, to a solution, in which there is no dispersed phase.

As used herein, emulsion refers to a colloidal dispersion of two immiscible liquids, for example, an oil and water (or other aqueous liquid), one of which is part of a continuous phase and the other of which is part of a dispersed phase. The provided compositions include emulsions, typically oil-in-water nanoemulsions, in which the oil phase is the dispersed phase and the water phase is the continuous phase. Emulsions typically are stabilized by one or more surfactants and/or co-surfactants and/or emulsion stabilizers. Surfactants form an interfacial film between the oil and water phase of the emulsion, providing stability. Typically, the nanoemulsions of the provided compositions contain micelles, containing one or more surfactant surrounding a non-polar active ingredient, which are dispersed in the water phase. Exemplary of the provided emulsions are liquid dispersion compositions, which are made by diluting the provided pre-emulsion compositions.

As used herein, a nanoemulsion is an emulsion in which the dispersed droplets, for example, the micelles, have a diameter (particle size) less than 1000 nm or less than about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Exemplary of nanoemulsions are the provided liquid dilution compositions, for example, the aqueous liquid dilution compositions, containing the diluted pre-emulsion compositions.

As used herein, "surfactant" and "surface active agent" are used synonymously to refer to synthetic and naturally occurring amphiphilic molecules, for example, molecules having both hydrophobic portion(s) and hydrophilic portion(s). In one example, the hydrophobic portion of the surfactant molecule is a hydrophobic tail and the hydrophilic portion of the surfactant is a hydrophilic head. Due to their amphiphilic (amphipathic) nature, surfactants and co-surfactants typically can reduce the surface tension between two immiscible liquids, for example, the oil and water phases in an emulsion, for example, a nanoemulsion, thus stabilizing the emulsion. Different surfactants can characterized based on their relative hydrophobicity and/or hydrophilicity. For example, relatively lipophilic surfactants are more soluble in fats, oils and waxes, typically having HLB values less than 10 or about 10, while relatively hydrophilic surfactants are more soluble in aqueous compositions, for example, water, and typically have HLB values greater than 10 or about 10. Relatively amphiphilic surfactants are soluble in both oil and water based liquids and typically have HLB values close to 10 or about 10.

Typically, the surfactants used in the provided compositions have an HLB value between 14 or about 14 and 20 or about 20, for example, 14, 15, 16, 17, 18, 19, 20, about 14, about 15, about 16, about 17, about 18, about 19 or about 20. Exemplary of a surfactant that can be used in the provided compositions is a PEG-derivative of Vitamin E, such as tocotrienol or tocopherol PEG diesters, such as TPGS (e.g. TPGS 1000) and TPGS analogs. Other known surfactants having HLB values between 14 or about 14 and 20 or about 20, typically between about 16 and 18, also can be suitable. For example, surfactants having similar properties to TPGS also can be used. Typically, the surfactant is a natural surfactant, for example, a surfactant that is G.R.A.S. (generally recognized as safe) by the FDA and/or Kosher certified.

Surfactants include, but are not limited to, soaps, detergents, lipids, emulsifiers, dispersing agents and wetting agents. Surfactants include molecules that emulsify liquids, for example, by forming an emulsion in an aqueous medium or aqueous liquid dilution composition, for example, forming a colloidal dispersion of two immiscible liquids in the form of droplets, for example, an emulsion such as a microemulsion. Surfactants include compounds that form various macromolecular structures, for example, aggregates, in liquids, for example, micelles, lipid bilayer structures, including liposomes, and inverse micelles. The compositions (e.g. nanoemulsions) provided herein typically contain micelles, for example, micelles encapsulating the non-polar active ingredient(s).

As used herein, "pre-emulsion composition" refers to the provided compositions containing the non-polar compounds that can be diluted in aqueous medium to form the liquid dilution compositions, typically aqueous liquid dilution compositions. In one example, the aqueous liquid dilution composition are clear aqueous liquid dilution compositions. Typically, the pre-emulsion compositions are solid compositions. Typically, the pre-emulsion compositions are non-aqueous pre-emulsion compositions. Typically, the pre-emulsion composition is formulated, (e.g. using the provided methods for formulating the pre-emulsion compositions) such that dilution of the composition in an aqueous medium yields an aqueous liquid dilution composition having one or more desirable properties, for example, being free from visible particles and/or visible crystals, exhibiting no ringing or phase separation, and/or having a desirable clarity, for example, a desired turbidity (NTU) value (e.g. an NTU of less than 1000 or about 1000, typically less than 500 or about 500, typically less than 300 or about 300 nm, typically less than 250 or about 250 typically less than 200 or about 200, e.g. less than 150 or about 150) or a desired average particle size (e.g. less than 1000 or about 1000, typically less than 500 or about 500, typically less than 300 or about 300 nm, typically less than 200 or about 200, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm). In another example, the pre-emulsion composition is formulated such that dilution of the composition in an aqueous medium, for example, a beverage, yields a liquid dilution composition that is as clear as or substantially as clear as the aqueous medium itself. The provided pre-emulsion compositions contain one or more non-polar active ingredients and at least one surfactant. Typically, the pre-emulsion compositions further contain a preservative, for example, a natural preservative such as benzyl alcohol. In some examples, the pre-emulsion compositions further contain one or more solvents, such as oils, for example, Vitamin E oil and/or flaxseed oil.

As used herein, a solid pre-emulsion composition is a pre-emulsion composition that is not a liquid (or gas) at room temperature (e.g. ambient temperature, for example, 25° C. or about 25° C.), for example, having a waxy consistency at room temperature (ambient temperature), for example at 25° C. or about 25° C. Typically, the solid pre-emulsion compositions become liquid when heated, for example, when heated to 120° F., or about 120° F., to 125° F., or about 125° F., to 140° F., or about 140° F., 50° C. or about 50° C., 60° C. or about 60° C. Typically, the solid pre-emulsion compositions are non-aqueous compositions.

As used herein, a PEG derivative of Vitamin E is a compound containing one or more Vitamin E moiety (e.g. a tocopherol or tocotrienol) joined, for example by an ester, ether, amide or thioester bond, with one or more polyethylene glycol (PEG) moieties, via a linker, for example a dicarboxylic or tricarboxylic acid. Exemplary of PEG derivatives of Vitamin E are tocopherol polyethylene glycol succinate (TPGS), TPGS analogs, TPGS homologs and TPGS derivatives.

As used herein, a tocopherol polyethylene glycol diester (TPGD) is a PEG-derivative of tocopherol where the linker is a dicarboxylic acid (a carboxylic acid having two carboxy groups, e.g. succinic acid), such as succinic acid. Exemplary of dicarboxylic acids that can be used as linkers in these tocopherol and tocotrienol PEG diester surfactants are succinic acid, sebacic acid, dodecanodioic acid, suberic acid, or azelaic acid, citraconic acid, methylcitraconic acid, itaconic acid, maleic acid, glutaric acid, glutaconic acid, fumaric acids and phthalic acids. Exemplary of TPGDs are tocopherol succinate polyethylene glycol (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, among others.

As used herein, "tocopherol polyethylene glycol succinate," "TPGS," "tocopheryl polyethylene glycol succinate surfactant" and "TPGS surfactant" refer to tocopherol polyethylene glycol (PEG) diesters that are formed by joining, via esterification, tocopherol succinate, which itself is an ester made by esterification of tocopherol and succinic acid. The PEG moiety of the TPGS surfactant can be any PEG moiety, for example, PEG moieties between 200 or about 200 and 20,000 or about 20,000 Da, typically between 200 or about 200 and 6000 or about 6000 Da, for example, between 600 or about 600 Da and 6000 or about 6000 Da, typically between 200 or about 200 Da and 2000 or about 2000 Da, between 600 or about 600 Da and 1500 or about 1500 Da, 200 or about 200 Da, 300 or about 300 Da, 400 or about 400 Da, 500 or about 500 Da, 600 or about 600 Da, 800 or about 800 Da, and 1000 or about 1000 Da, and PEG moieties that are modified, for example, methylated PEG (m-PEG) and/or PEG moieties including other PEG analogs, e.g. PEG-NHS, PEG-aldehyde, PEG-SH, PEG-NH$_2$, PEG-CO$_2$H, and branched PEGs.

Exemplary of the TPGS surfactants is TPGS-1000, which has a PEG moiety of 1000 Da. The TPGS can be any natural, water-soluble, tocopherol polyethylene glycol succinate, for example, the food grade TPGS sold under the name Eastman Vitamin E TPGS®, food grade, by Eastman Chemical Company, Kingsport, TN. This TPGS is a water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. A similar compound can be made by esterifying the carboxyl group of the d,1 form of synthetic Vitamin E with PEG 1000. It forms a clear liquid when dissolved 20% in water. This tocopheryl polyethylene glycol is a water-soluble preparation of a fat-soluble vitamin (vitamin E), for example, as disclosed in U.S. Pat. Nos. 3,102,078 and 2,680,749 and U.S. Published Application Nos. 2007/0184117 and 2007/0141203. Also exemplary of the TPGS surfactant that can be used in the provided compositions is the Water Soluble Natural Vitamin E (TPGS), sold by ZMC-USA, The Woodlands, Texas. Any known source of TPGS can be used. Typically, the TPGS surfactant is GRAS and Kosher certified. TPGS typically has an HLB value of between 16 or about 16 and 18 or about 18.

As used herein, analog refers to a chemical compound that is structurally similar to another compound (referred to as a parent compound), but differs slightly in composition, for example, by the variation, addition or removal of an atom, one or more units (e.g. methylene unit(s)- $(CH_2)_n$) or one or more functional groups. The analog can have different chemical or physical properties compared with the original compound and/or can have improved biological and/or chemical activity. Alternatively, the analog can have similar or identical chemical or physical properties compared with the original compound and/or can have similar or identical biological and/or chemical activity For example, the analog can be more hydrophilic or it can have altered reactivity as compared to the parent compound. The analog can mimic the chemical and/or biologically activity of the parent compound (i.e., it can have similar or identical activity), or, in some cases, can have increased or decreased activity. The analog can be a naturally or non-naturally occurring (e.g. synthetic) variant of the original compound. Other types of analogs include isomers (enantiomers, diasteromers, and the like) and other types of chiral variants of a compound, as well as structural isomers. The analog can be a branched or cyclic variant of a linear compound. For example, a linear compound can have an analog that is branched or otherwise substituted to impart certain desirable properties (e.g., improve hydrophilicity or bioavailability). Exemplary of the analogs used in the provided compositions and methods are TPGS analogs, which typically are used as surfactants, for example, in place of the TPGS parent compound in any of the provided compositions.

As used herein, homolog refers to an analog that differs from the parent compound only by the presence or absence of a simple unit, such as a methylene unit, or some multiple of such units, e.g., —$(CH_2)_n$—. Typically, a homolog has similar chemical and physical properties as the parent compound. Exemplary of the homologs used in the provided compositions and methods are TPGS homologs.

As used herein, "tocopherol polyethylene glycol succinate analog" "TPGS analog" and "TPGS analog surfactant" refer to compounds, other than TPGS, that are similar to a parent TPGS compound, but differ slightly in composition, for example, by the variation, addition or removal of an atom, one or more units (e.g. methylene unit(s)- $(CH_2)_n$) or one or more functional groups. TPGS analogs include Vitamin E derived surfactants, including PEG derivatives of Vitamin E, including vitamin E PEG diesters, such as, but not limited to, tocophyrol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E. In one example, the surfactant in the provided compositions is a TPGS analog.

Exemplary of TPGS analogs are compounds, other than TPGS compounds, having the formula shown in Scheme I.

As used herein, TPGS-1000 analogs are compounds other than TPGS-1000 that are similar to a parent TPGS-1000 compound, but differ slightly in composition, for example, by the variation, addition or removal of an atom, one or more units (e.g. methylene unit(s)-$(CH_2)_n$) or one or more functional groups. In one example, the surfactant in the compositions provided herein is a TPGS-1000 analog. Suitable TPGS-1000 analogs include, but are not limited to, other TPGS compounds, having PEG moietie(s) that vary in chain length and molecular weight compared to TPGS-1000, including, for example, TPGS compounds having PEG moieties between 200 or about 200 to 20,000 or about 20,000 Da, typically between 200 and 6000 Da, for example, between 600 or about 600 Da and 6000 or about 6000 Da, typically

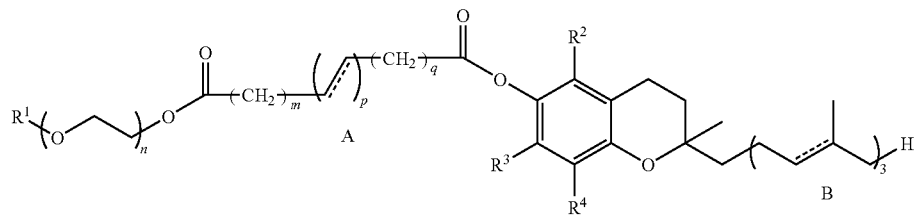

Scheme I where $R^1$, $R^2$, $R^3$ and $R^4$ each independently is H or Me; each dashed line is, independently, a single or double bond; n is an integer from 1-5000; m and q each independently are 0 or 1; and p is an integer from 1-20.

For example, TPGS analogs include compounds having the formula in Scheme I, where, when the bonds represented by the dashed lines marked by "A" and "B" are single bonds, m and q both equal 0, and p is any integer from 2-20. TPGS analogs also include compounds where the dashed line at B or the dashed line at A, or both the dashed lines, represents at least one double bond. For example, TPGS analogs include a compound as in Scheme I, where when the dashed line in A represents only single bonds, the dashed line in "B" represents one or more double bond, e.g. tocotrienol PEG diesters. TPGS also include compounds as in Scheme I, where when the dashed line marked "B" represents only single bonds, the dashed line marked "A" represents one or more double bonds; or when the dashed line labeled "A" does not represent double bonds, and m and q are both zero, p is greater than 1. For example, TPGS analogs include compounds where one or more of the dashed lines represents a double bond, for example, PEG derivatives of tocotrienol esters (e.g. PTrienS).

Also exemplary of TPGS analogs include compounds other than TPGS having the formula shown in SCHEME III:

between 200 or about 200 Da and 2000 or about 2000 Da, between 600 or about 600 Da and 1500 or about 1500 Da 200, 300, 400, 500, 600, 800, and 1000 Da. Also exemplary of TPGS-1000 analogs are TPGS compounds having PEG moieties that are modified, for example, methylated PEG (m-PEG) and/or PEG moieties including other PEG analogs, e.g. PEG-NHS, PEG-aldehyde, PEG-SH, PEG-$NH_2$, PEG-$CO_2H$, and branched PEGs. Also exemplary of TPGS-1000 analogs are any TPGS analogs, e.g. Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E.

As used herein, TPGS homologs are analogs of TPGS that differ from a TPGS parent compound only by the presence or absence of a simple unit, such as a methylene unit, or some multiple of such units, e.g., $-(CH_2)_n-$. In one aspect, TPGS homologs are used as surfactants in the provided compositions. Typically, suitable TPGS homologs have similar surfactant properties compared to the parent compound (TPGS), for example, similar HLB values, for example, HLB values

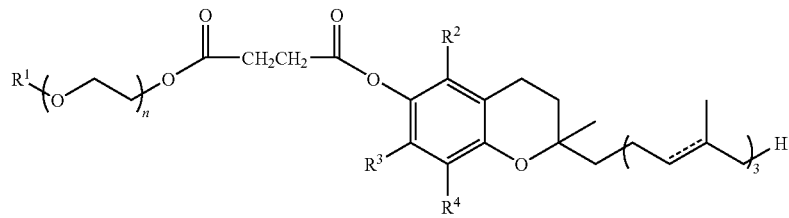

Scheme III where $R^1$, $R^2$, $R^3$ and $R^4$ are hydrogen or methyl ($CH_2$), and n is an integer selected from among 1-5000.

between 14 or about 14 and 20 or about 20. Exemplary of TPGS homologs are tocophyrol polyethylene glycol sebacate (PTS), tocopherol polyethylene glycol dodecanodioate (PTD), tocopherol polyethylene glycol suberate (PTSr), tocopherol polyethylene glycol azelaate (PTAz). Exemplary of TPGS homologs are compounds having the formula in Scheme I (above), where neither the A or B dashed line represents a double bond and where, when m and q both are 0, p is greater than 1.

As used herein, TPGS-1000 homologs are analogs of TPGS-1000 that differ from a TPGS-1000 parent compound only by the presence or absence of a simple unit, such as a methylene unit, or some multiple of such units, e.g., —$(CH_2)_n$—. Suitable TPGS-1000 homologs have similar surfactant properties compared to the parent compound (TPGS-1000), for example, similar HLB values, for example, HLB values between 14 or about 14 and 20 or about 20. Suitable TPGS-1000 homologs include TPGS-1000 homologs with slight variations in the length of the PEG chain moiety, and me-TPGS-1000, which is a TPGS-1000 having a methyl cap on the PEG moiety.

As used herein, HLB refers to a value that is used to index and describe a surfactant according to its relative hydrophobicity/hydrophilicity, relative to other surfactants. A surfactant's HLB value is an indication of the molecular balance of the hydrophilic and lipophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactant will form and the solubility of the surfactant. See, for example, Griffin, W.C. *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophillic surfactants have greater solubility in oil and lipophilic substances, while hydrophilic surfactants dissolve more easily in aqueous media. In general, surfactants with HLB values greater than 10 or greater than about 10 are called "hydrophilic surfactants," while surfactants having HLB values less than 10 or less than about 10 are referred to as "hydrophobic surfactants." HLB values have been determined and are available for a plurality of surfactants (e.g. see U.S. Pat. No. 6,267,985). It should be appreciated that HLB values for a given surfactant or co-surfactant can vary, depending upon the empirical method used to determine the value. Thus, HLB values of surfactants and co-surfactants provide a rough guide for formulating compositions based on relative hydrophobicity/hydrophilicity. For example, a surfactant typically is selected from among surfactants having HLB values within a particular range of the surfactant or co-surfactant, that can be used to guide formulations. Table 1 lists HLB values of exemplary surfactants and co-surfactants.

TABLE 1

HLB Values of Exemplary Surfactants and Co-Surfactants

| Surfactant/co-surfactant | HLB |
|---|---|
| PEG-2 Hydrogenated Castor Oil | 1.7 |
| Sorbitan Trioleate | 1.8 |
| Sorbitan Tristearate | 2.1 |
| Glyceryl Stearate | 3.5 |
| Sorbitan Sesquioleate | 3.7 |
| Labrafil | 4 |
| Sorbitan Oleate | 4.3 |
| Sorbitan monostearate | 4.7 |
| PEG-2 oleyl ether | 4.9 |
| PEG-2 stearyl ether | 4.9 |
| PEG-7 Hydrogenated Castor Oil | 5 |
| PEG-2 cetyl ether | 5.3 |
| PEG-4 Sorbitan Stearate | 5.5 |
| PEG-2 Sorbitan Isostearate | 6 |
| Sorbitan Palmitate | 6.7 |
| Triton SP-135 | 8 |
| Sorbitan monolaurate | 8.6 |
| PEG-40 Sorbitan Peroleate | 9.5 |
| PEG-4 lauryl ether | 9.7 |
| Polysorbate 81 | 10 |
| PEG-40 Sorbitan Hexaoleate | 10 |
| PEG-40 Sorbitan Perisostearate | 10 |
| PEG-10 Olive Glycerides | 10 |
| PEG sorbitol hexaoleate | 10.2 |
| Polysorbate 65 | 10.5 |
| PEG-25 Hydrogenated Castor Oil | 10.8 |
| Polysorbate 85 | 11 |
| PEG-7 Glyceryl Cocoate | 11 |
| PEG-8 Stearate | 11.1 |
| PEG sorbitan tetraoleate | 11.4 |
| PEG-15 Glyceryl Isostearate | 12 |
| PEG-35 Almond Glycerides | 12 |
| Tocopherol polyethylene glycol succinate (TPGS) | 16-18 |
| PEG-10 oleyl ether | 12.4 |
| PEG-8 isooctylphenyl ether | 12.4 |
| PEG-10 stearyl ether | 12.4 |
| PEG-35 Castor Oil | 12.5 |
| PEG-10 cetyl ether | 12.9 |
| Nonoxynol-9 | 12.9 |
| PEG-40 Castor Oil | 13 |
| PEG-10 isooctylphenyl ether | 13.5 |
| PEG-40 Hydrogenated Castor Oil | 14 |
| Labrasol | 14 |
| Nonoxynol-15 | 14.2 |
| PEG-12 tridecyl ether | 14.5 |
| PEG-18 tridecyl ether | 14.5 |
| Polysorbate 60 | 14.9 |
| Polysorbate 80 | 15 |
| PEG-20 Glyceryl Stearate | 15 |
| PEG-20 Stearate | 15 |
| PEG-20 stearyl ether | 15.3 |
| PEG-20 oleyl ether | 15.3 |
| Polysorbate 40 | 15.6 |
| PEG20 cetyl ether | 15.7 |
| PEG(20) hexadecyl ether | 15.7 |
| PEG-60 Hydrogenated Castor Oil | 16 |
| PEG-30 Stearate | 16.5 |
| Polysorbate 20 | 16.7 |
| PEG-75 Lanolin | 16.7 |
| PEG23 lauryl ether | 16.9 |
| PEG-40 Stearate | 17.3 |
| PEG-50 Stearate | 17.7 |
| PEG40 isooctylphenyl ether | 17.9 |
| PEG-100 Stearate | 18.8 |
| Pluronic F68 | 29 |
| Phosphatidylcholine | 7.6 |

The surfactants and HLB values set forth in Table 1 are exemplary. Any known surfactant or co-surfactant can be used with the provided compositions (e.g. see U.S. Pat. No. 6,267,985). The surfactant(s) contained in the provided compositions typically have an HLB value between 14 or about 14 and 20 or about 20, for example, 14, 15, 16, 17, 18, 19, 20, about 14, about 15, about 16, about 17, about 18, about 19 or about 20. Exemplary of a surfactant that can be used in the provided compositions is a PEG-derivative of Vitamin E, such as tocotrienol or tocopherol PEG diesters, such as TPGS (e.g. TPGS 1000) and TPGS analogs. Other known surfactants having HLB values between 14 or about 14 and 20 or about 20, typically between about 16 and 18, also can be suitable. For example, surfactants having similar properties to TPGS also can be used. Typically, the surfactant is a natural surfactant, for example, a surfactant that is G.R.A.S. (generally recognized as safe) by the FDA and/or Kosher certified.

As used herein, micelle refers to aggregates formed by surfactants that typically form when the surfactant is present in an aqueous composition, typically when the surfactant is used at a concentration above the critical micelle concentration (CMC). In micelles, the hydrophilic portions of the surfactant molecules contact the aqueous or the water phase, while the hydrophobic portions form the core of the micelle, which can encapsulate non-polar ingredient(s), for example, the non-polar compounds in the provided compositions. Typically, the surfactants in the provided aqueous dilution compositions form micelles containing the non-polar ingredient at their center in aqueous liquid dilution compositions. Typically, the micelles in the provided aqueous dilution compositions have a particle size of less than about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, inverse micelles are surfactant aggregates that typically form in lipophilic solution, with the hydrophilic portions forming the core. When the cross sectional area of the hydrophobic region of the surfactant molecule is greater than that of the hydrophilic part of the molecule, the formation of micelles, which can be hexagonal phase structures, is favored.

As used herein, liposomes are surfactant aggregates composed of lipid bilayers, typically having an aqueous core. Liposomes typically are formed by lipid surfactants, typically, phospholipids, which are amphipathic, phosphate-containing lipids, for example, molecules containing one phosphate, a glycerol and one or more fatty acids, and similar surfactants. Alternatively, phospholipid surfactants can be used as co-surfactants, which can be incorporated into aggregates of other surfactant(s), for example, micelles. Lipid bilayers are two dimensional sheets in which all of the hydrophobic portions, e.g., acyl side chains, are shielded from interaction with aqueous liquid, except those at the ends of the sheet. An energetically unfavorable interaction of the acyl chains with water results in the folding of the bilayers to form liposomes, three-dimensional lipid bilayer vesicles. In one example, the liposome is formed as a single bilayer enclosing a single aqueous space (small unilamellar vesicles; SUVS). In another example, the liposome is composed of concentric bilayers with many aqueous spaces alternating with the bilayers (multilamellar vesicles; MLVS). Liposomes can be used to encapsulate both hydrophobic and hydrophilic active ingredients. In liposomes, non-polar active ingredients typically are partitioned within the bilayers whereas hydrophilic active ingredients typically are trapped within the aqueous compartments. In one example, liposomes can be advantages as a carrier/encapsulation system because they are stable and can protect the active ingredients from degradation, e.g., by oxygen, digestive enzymes, etc.

As used herein, "co-surfactant" is used to refer to a surfactant, typically a phospholipid, that is used, in the provided compositions, in combination with a surfactant, for example, a primary surfactant, for example, to improve the emulsification of the provided compositions and/or compounds, for example, to emulsify the ingredients. In one example, the provided compositions contain at least one surfactant and at least one co-surfactant. Typically, the co-surfactant is a lipid, for example, a phospholipid, for example, phosphatidylcholine. In one example, the co-surfactant has an HLB value of between 7 or about 7 and 8 or about 8. Typically, the co-surfactant represents a lower percent, by weight, of the provided compositions, compared to the surfactant. Thus, the provided compositions typically have a lower concentration of the co-surfactant(s) than of the surfactant.

As used herein, a phospholipid is an amphipathic, phosphate-containing lipid, for example, a molecule containing one phosphate, a glycerol and one or more fatty acids. In one example, one or more phospholipids is used as a co-surfactant in the provided compositions. Exemplary of the phospholipids used in the provided compositions are lecithin, including phosphatidylcholine (PC), phosphatidylethanolamine (PE), distearoylphosphatidylcholine (DSPC), phosphatidylserine (PS), phosphatidtylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids. Synthetic Phospholipids, PEG-ylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

Typically, for micelle formation, surfactant(s) are used in which the cross sectional area of the hydrophilic portion of the surfactant molecule is greater than that of the hydrophobic portion of the molecule. For example, TPGS is a surfactant used to stabilize oil-in-water emulsions containing the non-polar active ingredients, for example, in nanometer-sized droplets suspended or dispersed in an aqueous phase or aqueous liquid, for example, aqueous medium, as spherical micelles, containing the hydrophilic portions of the molecule(s) facing the aqueous phase and the hydrophobic portions at the center of the spherical micelles, for example, surrounding the non-polar active ingredient.

When the cross sectional area of the hydrophobic region of the surfactant molecule is greater than that of the hydrophilic part of the molecule, the formation of hexagonal phase structures, sometimes referred to as an inverse micelle is favored.

Typically, in the provided emulsion compositions, the surfactants and/or co-surfactants, aggregate in the nanoemulsions and the aqueous liquids to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant.

As used herein, "tocopherol polyethylene glycol succinate surfactant" and "TPGS surfactant" are used synonymously to refer to any natural, water-soluble, tocopherol polyethylene glycol succinate surfactant or tocopheryl polyethylene glycol surfactant, for example, the food grade TPGS surfactant sold under the name Eastman Vitamin E TPGS®, food grade, by Eastman Chemical Company, Kingsport, TN. This surfactant is a water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. A similar compound can be made by esterifying the carboxyl group of the d,l form of synthetic Vitamin E with PEG 1000. It forms a clear liquid when dissolved 20% in water. This tocopheryl polyethylene glycol is a water-soluble preparation of a fat-soluble vitamin (vitamin E), for example, as disclosed in U.S. Pat. Nos. 3,102,078 and 2,680,749 and U.S. Published Application Nos. 2007/0184117 and 2007/0141203. The PEG moiety of alternative TPGS surfactants can have a molecular weight range of about 200 or 200 to 20,000 or about 20,000 Da. Also exemplary of the TPGS surfactant that can be used in the provided compositions is the Water Soluble Natural Vitamin E (TPGS), sold by ZMC-USA, The Woodlands, Texas. Any known source of TPGS can be used. Typically, the TPGS surfactant is GRAS and Kosher certified. TPGS typically has an HLB value of between 16 or about 16 and 18 or about 18.

As used herein, "particle size" and "average particle size" refer synonymously to the diameter of particles in the provided liquids, for example, the droplet diameter or micelle diameter in an emulsion. Typically, the dilution compositions, made by diluting the provided pre-emulsion compositions, have a particle size of less than about 1000 nm, typically, less than 500 nm or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In one example, the dilution compositions yielded by diluting the pre-emulsion compositions have a particle size between 10 nm or about 10 nm and 1000 nm or about 1000 nm, for example, between 15 nm or about 15 nm and 500 nm or about 500 nm, for example, between 15 nm or about 15 nm and 300 nm or about 300 nm, for example, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200 nm or more. Typically, the provided pre-emulsion compositions are formulated such that, dilution of the pre-emulsion composition in an aqueous medium yields a liquid dilution composition having an appropriate particle size, for example, between 15 nm or about 15 nm and 500 nm or about 500 nm. Information about particles in the liquids alternatively be expressed in terms of particle number, for example, ppm (parts per million) or percent solids, in the liquids.

As used herein, visible particles are particles, for example, in a liquid, for example, an emulsion, that are visible when viewing the liquid with the naked eye (e.g. without magnification). In one example, the visible particles are particles that are observed by the artisan formulating the compositions, for example, the pre-emulsion compositions or the aqueous liquid dilution compositions containing the diluted pre-emulsion compositions. In one example, the provided compositions contain no visible particles. In another example, the compositions contain few visible particles, for example, no more visible particles than another liquid, for example, a beverage. The presence of visible particles and the number of visible particles is determined by empirical observation.

As used herein, visible crystals are crystals, for example, in a liquid, for example, an emulsion, that are visible when viewing the liquid with the naked eye (e.g. without magnification). In one example, the visible crystals are crystals that are observed by the artisan formulating the compositions, for example, the pre-emulsion compositions or the aqueous liquid dilution compositions containing the diluted pre-emulsion compositions. In one example, the provided compositions contain no visible crystals. In another example, the compositions contain few visible crystals, for example, no more visible crystals than are contained in another liquid, for example, a beverage. The presence of visible crystals is determined by empirical observation.

As used herein, "turbidity" is a measure of the cloudiness or haziness of a liquid, caused by particles in suspension in the liquid. Turbidity can measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance.

Turbidity can measured optically, for example, by using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions. The units of a turbidity value measured with a nephelometer are Nephelomtetric Turbidity Units (NTU). In one example, the provided compositions, for example, the aqueous liquid dilution compositions containing the diluted pre-emulsion compositions have low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 1000 or less than about 1000, less than 500 or less than about 500, less than 300 or less than about 300, less than 250 or less than about 250, 200 or less than about 200, for example, 200, 175, 150, 100, 50, 25 or less.

As used herein, a turbid liquid is one that is thick or opaque with visible particles in suspension, for example, a liquid that is cloudy or muddy in appearance.

As used herein, "clear" can be used to describe a composition as provided herein, for example, the aqueous liquid dilution compositions containing the diluted pre-emulsion compositions. In one example, a clear liquid is one that does not appear cloudy by empirical observation (e.g. to the naked eye) and/or does not contain particles or crystals that are visible to the naked eye, or that does not exhibit "ringing." In another example, a clear liquid is one that has a low or relatively low turbidity value, for example an NTU value, that is less than or equal to a desired NTU value. In one example, a clear liquid has an NTU value of less than 300 or less than about 300, typically less than 250 or less than about 250, typically less than 200 or less than about 200, for example, 200, 175, 150, 100, 50, 25 or less. In another example, a liquid is clear if it has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, a clear liquid is one that has a small or relatively small average particle size (e.g. less than 1000 nm or about 1000 nm, typically less than 500 nm or less than about 500 nm, typically less than 300 nm or about 300 nm, typically less than 250 nm or about 250 nm, typically less than 200 nm or about 200 nm, for example, less than 150 or about 150 nm, less than 100 nm or about 100 nm, less than 75 nm or about 75 nm, less than 50 nm or about 50 nm, less than 25 nm or about 25 nm or less than 10 nm or about 10 nm), for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

In another example, clarity is expressed relatively. For example, it can be desired that a particular composition is equally as clear, about as clear, or more clear than another liquid (as measured empirically, or by measuring turbidity value or particle size). For example, clarity can be assessed relative to another aqueous liquid dilution composition, for example, a beverage For example, In one example, a liquid is clear if it is similar in appearance to another clear liquid, for example, a beverage, for example, water. For example, it can be desired that a composition has a particle size that is less than or equal to another liquid, for example, a beverage. In another example, it can be desired that a composition has a turbidity value that is less than or equal to another liquid, for example, a beverage. In another example, it can be desired that a composition appears more clear or as clear as another liquid, for example, a beverage, for example, by having no more visible particles, no more crystal formation and/or no more cloudiness than the other liquid. In one example, the provided compositions are clear. In another example, they are relatively clear or as clear as or about as clear as another liquid, for example, a beverage that does not contain the non-polar compound or pre-emulsion composition.

As used herein, "hydrophilic" refers to ingredients and/or compounds having greater solubility in aqueous liquids, for example, water, than in fats, oils and/or organic solvents (e.g. methanol, ethanol, ethyl ether, acetone and benzene).

As used herein, "non-polar" "lipophilic" and "lipid-soluble" synonymously refer to compounds (e.g. non-polar compounds) and/or ingredients, for example, non-polar active ingredients, which have greater solubility in organic solvents (e.g. ethanol, methanol, ethyl ether, acetone, and benzene) and in fats and oils, than in aqueous liquids, for example, water. Non-polar compounds include drugs, hormones, vitamins, nutrients and other lipophilic compounds. Typically, the non-polar compounds used in the provided compositions are poorly water soluble, for example, water insoluble or compounds having low water solubility. Exemplary non-polar compounds include non-polar active ingredients, for example, lipid-soluble drugs, hormones, essential fatty acids, for example, polyunsaturated fatty acids (PUFA), for example, omega-3 and omega-6 fatty acids, vitamins, nutrients, neutraceuticals, minerals and other compounds. Additional exemplary non-polar compounds are described herein. The provided compositions can be formulated with any non-polar compound, for example, non-polar active ingredient.

As used herein, non-polar active ingredient refers to a non-polar compound that, when administered to a subject, for example, a human, induces or is proposed to induce a desired biological response, such as altering body function at the cellular, tissue, organ or other level, and/or altering cosmetic appearance or other property, or a non-polar compound that is ingested in order to achieve a desired effect. Non-polar active ingredients can be any synthetic or natural non-polar ingredient or compound, including a pharmaceutical, drug, therapeutic, nutritional supplement, herb, hormone or other ingredient. Non-polar active ingredients can include the non-polar active ingredients listed herein, as well as other pharmaceutically acceptable or food-grade active derivatives of the active ingredients, for example, salts, esters, amides, prodrugs, active metabolites, isomers, fragments, analogs, and the like. Active ingredients can include compounds proven to have a desired effect and also compounds thought to produce such effects, for example, compounds typically ingested for nutritional supplementation purposes.

As used herein, a subject includes an animal, typically a mammal, typically a human.

As used herein, additives include anything that one can add to a food, beverage, or other human consumable, to enhance one or more of its nutritional, pharmaceutical, dietary, health, nutraceutical, health benefit, energy-providing, treating, holistic, or other properties. For example, provided herein are compositions and methods for preparing foods, beverages and other aqueous human consumables, that include one or more additives, typically oil based additives (e.g. non-polar compounds), such as nutraceuticals, pharmaceuticals, vitamins, typically oil soluble vitamins, for example, Vitamin D, E and A, minerals, fatty acids, such as essential fatty acids, e.g. polyunsaturated fatty acids, for example, omega-3 fatty acids and omega-6 fatty acids, for example, ALA, DHA, EPA, GLA, CLA, saw palmetto extract, flaxseed oil, fish oil, algae oil, phytosterols, and Coenzymes, for example, Coenzyme Q10 and other additives.

As used herein, an effective amount of an additive, such as a non-polar compound (e.g. non-polar active ingredient) refers to the quantity and/or concentration of the additive necessary for preventing, curing, ameliorating, arresting or partially arresting a symptom of a disease or disorder, or the quantity and/or concentration desired by an individual for intake, such as daily intake, and/or nutritional supplementation, for example, an amount sufficient to enhance the nutritional, pharmaceutical, nutraceutical, health or energy property of a food, beverage, or other consumable. In some examples, it is desired that the provided compositions, for example, and/or the liquid dilution compositions, contain an effective amount of a particular non-polar compound, for example, a particular amount per volume or weight of the composition.

In one example, an effective amount is a concentration or amount of a pre-emulsion composition where at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces of an aqueous medium, e.g. a beverage.

As used herein, unit dose form refers to physically discrete units suitable for human and animal subjects and packaged individually as is known in the art.

As used herein, "water insoluble" refers to a property of a compound, none of which dissolves when the compound is mixed with water, for example, when mixed with water at room temperature, for example, between 25 and 50° C. or between about 25 and 50° C. In one example, the non-polar compounds are water insoluble. In another example, the non-polar compounds in the provided compositions are slightly soluble in water, for example, having low water solubility.

As used herein, low water solubility refers water solubility of less than 30 or about 30 mg/mL, typically less than 20 mg/mL or about 20 mg/mL, typically, less than 10 mg/mL or about 10 mg/mL, typically less than 1 mg/mL or about 1 mg/mL, for example, solubility in water of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 mg/mL or less, for example, when mixed with water at room temperature, for example, between 25 and 50° C. or between about 25 and 50° C. As used herein, poorly water soluble can be used to refer to compounds, for example, non-polar compounds that are water insoluble or have low water solubility.

As used herein, a non-aqueous composition is a composition containing contain none or very little hydrophilic ingredient, for example, containing less than 5% or about 5%, by weight, hydrophilic ingredients, for example, less than 4% or about 4%, less than 3% or about 3%, less than 2% or about 2%, less than 1% or about 1%, or 0% or about 0%, by weight, hydrophilic ingredient(s).

As used herein, "waxy" is used to describe compositions and materials, typically oil-soluble compositions or materials, that are similar in consistency to one or more waxes. Typically, the solid pre-emulsion compositions provided herein have a waxy consistency at room temperature. Compositions and compounds having "waxy" consistencies typically have melting points or melting ranges above ambient temperature (e.g. above room temperature, for example, above 25° C. or about 25° C.), meaning they are either solid or semi-solid (e.g. creamy) at room temperature. Typically, waxy compositions are of relatively low viscosity a little above their liquefying point. Exemplary of waxes, which have waxy consistencies, are natural waxes, including waxes of vegetal origin, such as purcelline, shea butter, cocoa butter, Japan wax, esparto gras wax, cork wax, Guaruma wax, rice shoot wax, Ouricury wax, montan wax, sunflower wax, ceresine wax, sugar cane wax, carnauba wax, candelilla wax, lanolin, fruit-derived waxes, such as orange wax, lemon wax, grapefruit wax and bayberry wax, and the like; waxes of animal origin, such as beeswax, woolwax, spermateci and bear fat, shellac wax, and the like; mineral waxes such as ceresine and ozokerite waxes; and synthetic waxes, including petroleum-based waxes such as paraffin, petrolatum, micro wax, polyalkylene and polyethyleneglycol waxes, e.g. polyethylene wax; waxes based on chlorinated naphthalenes such as 'Halowax', synthetic hydrocarbon waxes, and the like.

As used herein, a non-aqueous composition (e.g. a non-aqueous pre-emulsion composition) is a composition that contains none, or very little of, any hydrophilic ingredient, for example, containing less than 10% or about 10%, typically less than 5% or about 5%, by weight, hydrophilic ingredients, for example, less than 4% or about 4%, less than 3% or about 3%, less than 2% or about 2%, less than 1% or about 1%, or 0% or about 0%, by weight, hydrophilic ingredient(s).

As used herein, liquid composition is used to refer to any liquid, for example, a composition that is a liquid at room temperature, for example, at 25° C. or about 25° C., or at a temperature of between 25° C. or about 25° C. and 50° C. or about 50° C. Exemplary of the provided liquid compositions are aqueous liquid dilution compositions into which one or more pre-emulsion composition has been diluted, for example, aqueous liquid dilution compositions containing the diluted pre-emulsion compositions. In this example, the non-polar compound and other lipophilic compounds form a dispersion phase within the aqueous liquid in an emulsion (e.g. nanoemulsion).

As used herein, "liquid dilution composition" "dilution composition" and "liquid dilution" are used synonymously to refer to a composition that contains one or more of the provided pre-emulsion compositions (e.g. the pre-emulsion compositions containing the non-polar compound(s)), diluted in a liquid, for example, an aqueous medium. Exemplary of the provided liquid dilution compositions are aqueous liquid dilution compositions, for example, beverages or other liquids containing the pre-emulsion compositions, for example, water, sauces, soups, syrups, soda, juice, for example, fruit juice, milk, coffee, tea, nutritional beverages, sports drinks, energy drinks, vitamin-fortified beverages, flavored water, and other beverages containing the diluted pre-emulsion compositions.

As used herein, aqueous liquid dilution compositions are liquid dilution compositions that are primarily aqueous, for example, a composition comprising a pre-emulsion composition diluted in an aqueous medium, for example, water or other beverage. It is not necessary that the aqueous liquid dilution composition is completely aqueous. For example, the aqueous liquid dilution compositions can contain an aqueous portion, for example, an aqueous continuous phase, as well as an additional portion, for example, a dispersion phase, for example, a lipophilic dispersion phase. Typically, the lipophilic dispersion phase contains one or more lipophilic substances, for example, one or more non-polar compounds, for example, non-polar active ingredients.

In one example, the dispersion phase of the aqueous liquid dilution composition has a small droplet (particle) size, for example, a particle size of less than 1000 or about 1000, typically less than 500 or about 500, typically less than 300 or about 300 nm, typically less than 250 or about 250 nm, typically less than 200 or about 200 nm, for example, a particle size equal to, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Exemplary of the provided aqueous liquid dilution compositions are beverages, for example, water, soda, juice, for example, fruit juice, milk, coffee, tea, nutritional beverages, sports drinks, energy drinks, vitamin-fortified beverages, flavored water, and other beverages. Typically, the aqueous liquid dilution compositions are beverages including the non-polar compound, for example, beverages containing the diluted pre-emulsion compositions.

As used herein, "oil phase" can be used to refer to the portion of the liquid dilution composition containing one or more lipophilic ingredients and/or amphiphilic ingredients, and is, in general, the lipid-soluble phase. Typically, the oil phase is the dispersion phase in the provided emulsion compositions.

As used herein, "water phase" is used to refer to the portion of the liquid dilution composition that contains one or more hydrophilic ingredients and/or amphiphilic ingredient. Typically, the water phase is the continuous phase.

As used herein, an initial pre-emulsion composition is a pre-emulsion composition that is made in the provided methods for formulating the pre-emulsion compositions. Typically, the initial pre-emulsion composition is made by selecting ingredients, for example, surfactant(s), non-polar compound(s), and, optionally, other ingredients (e.g. preservative(s) and/or solvent(s)), and selecting starting concentrations of the ingredients from an appropriate concentration range, as described herein. The initial pre-emulsion composition can be formulated based on parameters of an existing pre-emulsion composition, and/or according to the ingredients and concentration ranges provided herein. Using the provided formulation methods, the initial pre-emulsion composition is evaluated, for example, to determine whether the pre-emulsion composition has one or more desirable properties, for example, clarity. In one example, changes are made to the formulation of the initial pre-emulsion composition, as described herein. In another example, no changes are made and the formula of the initial pre-emulsion composition is used to make the pre-emulsion composition.

As used herein, stability refers to a desirable property of the provided compositions, for example, the ability of the provided compositions to remain free from one or more changes over a period of time, for example, at least or over 1, 2, 3, 4, 5, 6 or more days, at least or over 1, 2, 3, 4, or more weeks, at least or over 1, 2, 3, 4, 5, 6, 7, 8, 9, 10, 11, 12 or more months, or at least or over 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

As used herein, stabilize means to increase or improve the stability of a composition.

As used herein, room temperature and ambient temperature are used to describe a temperature that is common in one or more enclosed spaces in which human beings typically are or reside. Room temperature can vary, but generally refers to temperatures between 19° C. or about 19° C. and 25° C. or about 25° C. When a composition is stored at room temperature, it should be understood it is generally kept at a temperature within this range or about within this range.

As used herein, refrigerated temperature refers to a temperature that is common in a refrigerator, for example, a household or restaurant refrigerator, for example, a temperature that is cooler than room temperature, but typically a few degrees above the freezing point of water (0° F. or about 0° F., or −19° C. or −20° C.). Typically, refrigerated temperatures are between about 10° C. or about 10° C. and 0° C. or about 0° C., for example, 4° C. or about 4° C. When a composition is stored at a refrigerated temperature, it should be understood that it is kept at a temperature common to household or industrial refrigerators.

As used herein, frozen temperature refers to a temperature around or below the freezing point of water, e.g. a temperature commonly used in a household freezer, for example, 0° F. or about 0° F., for example, −19° C. or about −19° C. or −20° C. or about −20° C., or colder.

As used herein, the singular forms "a," "an" and "the" include plural referents unless the context clearly dictates otherwise. Thus, for example, reference to compound, comprising "an extracellular domain"" includes compounds with one or a plurality of extracellular domains.

As used herein, ranges and amounts can be expressed as "about" a particular value or range. About also includes the exact amount. Hence "about 5 grams" means "about 5 grams" and also "5 grams.' It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range, for example, 5.25, 6.72, 8.5, 11.95, etc grams.

As used herein, "optional" or "optionally" means that the subsequently described event or circumstance does or does not occur and that the description includes instances where said event or circumstance occurs and instances where it does not. For example, an optionally variant portion means that the portion is variant or non-variant. In another example, an optional ligation step means that the process includes a ligation step or it does not include a ligation step.

As used herein, "ringing" refers to the formation of a whitish or opaque ring around a container containing a liquid, for example, an aqueous liquid, for example a beverage, for example, a liquid dilution composition containing an emulsion or nanoemulsion. Typically, the ring forms around the perimeter of the container, typically at the surface level of the liquid in the container, for example, at the neck of the container. Ringing can occur over time and, if it occurs over a short period of time, can be a sign of instability. Ringing typically is undesirable, particularly in the case of a liquid for human consumption, for example, a beverage. Typically, the provided stable compositions do not exhibit "ringing" or are stable, without ringing, for a long period of time, for example, days, weeks, months or years. In one example, the compositions are free from ringing over time, when kept, for example, at room temperature, refrigerated and/or frozen. These desired properties of the provided compositions related to ringing can be affected by the particle size of the compositions, which can be influenced by selection of particular ingredients and concentrations of ingredients, for example, by properties of the surfactant(s), for example, the HLB of the surfactant(s).

As used herein, fatty acid refers to straight-chain hydrocarbon molecules with a carboxyl (COOH) group at one end of the chain.

As used herein, polyunsaturated fatty acid and PUFA are used synonymously to refer to fatty acids that contain more than one carbon-carbon double bond in the carbon chain of the fatty acid. PUFAs, particularly essential fatty acids, are useful as dietary supplements.

As used herein, essential fatty acids are PUFAs that mammals, including humans, cannot synthesize using any known chemical pathway. Thus, essential fatty acids must be obtained from diet or by supplementation. Exemplary of essential PUFA fatty acids are omega-3 (ω3; n-3) fatty acids and the omega-6 (ω-6; n-6) fatty acids.

As used herein, omega-3 (ω3; n-3) fatty acids are methylene interrupted polyenes, which have two or more cis double bonds, separated by a single methylene group and in which the first double bond appears at the third carbon from the last (ω) carbon. Omega-3 fatty acids are used as dietary supplements, for example, for disease treatment and prevention. In one example, the provided compositions contain non-polar active ingredients that contain at least one omega-3 fatty acids. Exemplary of Omega-3 fatty acids are Alpha-Linolenic acid (a-Linolenic acid; ALA) (18:3ω3) (a short-chain fatty acid); Stearidonic acid (18:4ω3) (a short-chain fatty acid); Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3ω3; 24:5ω3 and nisinic acid (24:6ω3). Longer chain Omega-3 fatty acids can be synthesized from ALA (the short-chain omega-3 fatty acid). Exemplary of non-polar active ingredients containing omega-3 fatty acids are non-polar active ingredients containing DHA and/or EPA, for example, containing fish oil, krill oil and/or algae oil, for example, microalgae oil, non-polar active ingredients containing ALA, for example, containing flaxseed oil.

As used herein, omega-6 (ω-6; n-6) fatty acids are methylene interrupted polyenes, which have two or more cis double bonds, separated by a single methylene group and in which the first double bond appears at the sixth carbon from the last (ω) carbon. In one example, the provided compositions contain non-polar active ingredients that contain at least one omega-3 fatty acids. Exemplary of Omega-6 fatty acids are Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and Docosapentaenoic acid (22:5ω6). Exemplary of non-polar active ingredients containing omega-6 fatty acids are ingredients containing GLA, for example, borage oil. Also exemplary of PUFA-containing non-polar active ingredients are compounds containing conjugated fatty acids, for example, Conjugated linoleic acid (CLA) and compounds containing saw palmetto extract.

As used herein, algae oil refers to any oil derived from marine dinoflagellates in, for example, microalgae, for example, *Crypthecodinium* sp, particularly, *Crypthecodinium cohnii*. In one example, algae oil is used as a non-polar compound, for example, as an active ingredient, in the provided compositions. The algae oil typically contains DHA. In one example, the algae oil is also a source of EPA.

As used herein, fish oil refers to any oil derived from any fish, typically a cold water fish, for example, from fish tissue, for example, from frozen fish tissue, for example, from cod liver. In one example, fish oil is used as a non-polar compound, for example, an active ingredient, in the provided compositions. The fish oil typically contains DHA. In one example, the fish oil also contains EPA.

As used herein, preservative and preservativer are used synonymously to refer to ingredients that can improve stability of the provided compositions. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

As used herein, solvent refers to an ingredient, for example, an oil, that is used to dissolve a compound, typically, the non-polar compound, for example, the non-polar active ingredient. For example, the solvent can be used to dissolve the non-polar active ingredient prior to or simultaneous with its incorporation into the composition. Typically, the solvent is an oil that is included in the composition in addition to the non-polar compound. For example, the solvent typically is not the non-polar compound. Certain compounds, for example, flaxseed oil and safflower oil, can be both solvents and non-polar active ingredients. Typically, the solvent contains one or more oils, typically oils other than the non-polar active ingredient or oil(s) not contained in the active ingredient. When a solvent is included in the pre-emulsion composition, it typically is used to dissolve the non-polar compound before mixing with the other ingredients, for example, before mixing with the other ingredients. In one example, use of a solvent reduces the crystal size and/or increase the clarity of the aqueous liquid dilution composition containing the diluted pre-emulsion composition. Exemplary of solvents that can be used in the provided pre-emulsion compositions are oils (in addition to the non-polar active ingredient), for example, Vitamin E oil, flaxseed oil, CLA, Borage Oil, D-limonene, Canola oil, corn oil, MCT oil and oat oil. Other oils also can be used. Exemplary of the Vitamin E oil, used as a solvent in the provided compositions, is the oil sold by ADM Natural Health and Nutrition, Decatur, Ill., under the name Novatol™ 5-67 Vitamin E (D-alpha-Tocopherol; ADM product code 410217). This Vitamin E oil contains at least 67.2% Tocopherol and approximately 32.8% soybean oil. In one example, the solvent is referred to, synonymously as "solubilizer."

As used herein, "w/w," "weight per weight," "by weight" "% by weight" and "weight percent" are used synonymously used to express the ratio of the mass of one component of a composition compared to the mass of the entire composition. For example, when a particular ingredient represents 1%, by weight (w/w) of a pre-emulsion composition, the mass of that ingredient is 1% of the mass of the entire pre-emulsion composition. Similarly, when the concentration of an ingredient is 50% (w/w) of the pre-emulsion composition, the mass of that ingredient is 50% of the entire mass of the pre-emulsion composition. Similarly, when a composition and/or a compound contains 10%, by weight of an ingredient, the mass of the ingredient is 10% of the total mass of the composition or compound. When only a concentration, or percentage (without units) is listed, it is to be understood that the concentration or percentage is a concentration or percentage, by weight.

Similarly, as used herein "v/v," "volume per volume," "percent by volume" and "volume percent" are used synonymously to express the ratio of the volume of one component of a composition and the volume of the entire composition.

As used herein, emulsion stabilizer refers to compounds that can be used to stabilize and/or emulsify and/or change the viscosity of the provided compositions, for example, the pre-emulsion composition and/or the aqueous compositions containing the diluted pre-emulsion compositions. In one example, the emulsion stabilizer increases the viscosity of the liquid pre-emulsion composition. In one example, one or more emulsion stabilizers is added, during formulation, after evaluation of an initial pre-emulsion composition, particularly if the oil and water phases of the aqueous liquid dilution composition resulting from dilution of the initial pre-emulsion composition appear to be separating. Addition of the emulsion stabilizer can prevent separation of the oil and water phases.

Exemplary of an emulsion stabilizer that can be used in the provided compositions is a composition containing a blend of gums, for example, gums used as emulsifying agents, for example, a blend containing one or more of xanthan gum, guar gum and sodium alginate, for example, the emulsion stabilizer sold under the brand name SALADIZER®, available from TIC Gums, Inc. (Belcamp, Md.). Other gums can be included in the emulsion stabilizer, for example, gum acacia and sugar beet pectin. Other blends of similar gums can also be used as emulsion stabilizers.

As used herein, a pH adjuster is any compound, typically an acid or a base, that is capable of changing the pH of the provided compositions, for example, to reduce the pH of the composition or to increase the pH of the composition, typically without altering other properties of the composition, or without substantially altering other properties. pH adjusters are well known. Exemplary of the pH adjusters are acids, for example, citric acid and phosphoric acid, and bases.

As used herein, flavor is any ingredient that changes, typically improves, the taste and/or smell of the provided composition, for example, the aqueous liquid dilution compositions, for example, the beverages.

As used herein, "not more than" and "NMT" refer to a quantity that is less than or equal to the listed quantity. Similarly, "not less than" and "NLT" refer to a quantity that is greater than or equal to the listed quantity.

As used herein, natural is used to refer to a composition, and/or ingredients in the composition, that can be found in nature and is not solely man-made. For example, benzyl alcohol is a natural preservative. Similarly, tocopheryl polyethylene glycol is a natural surfactant. In one example, the natural composition/ingredient is GRAS and/or Kosher—certified. Typically, the provided compositions are natural, semi-natural and/or contain one or more natural ingredients.

As used herein, "G.R.A.S." and "GRAS" are used synonymously to refer to compounds, compositions and ingredients that are "Generally Regarded as Safe" by the USDA, FDA for use as additives, for example, in foods, beverages and/or other substance for human consumption, for example, any substance that meets the criteria of sections 201 (s) and 409 of the U.S. Federal Food, Drug and Cosmetic Act. Typically, the compositions provided herein are GRAS certified.

As used herein, kosher is used to refer to substances that conform to Jewish Kosher dietary laws, for example, substances that do not contain ingredients derived from non-kosher animals or ingredients that were not made following kosher procedures. Typically, the compositions provided herein are Kosher certified.

As used herein, vessel refers to any container, for example, tanks, pots, vials, flasks, cylinders, and beakers, that can be used to contain the ingredients and/or phases of the provided compositions, during the methods for making the compositions. In one example (e.g. for the provided scaled-up methods), the vessel is a tank, which is used to mix and/or heat one or more ingredients and/or phases of the compositions, for example, the pre-emulsion compositions. In one example, the tank is a mixing tank, which is used to mix (and optionally heat) one or more ingredients of the compositions. In one example, the tank is a packaging or holding tank, which holds the provided compositions after forming the compositions, for example, the pre-emulsion compositions. A number of tanks are available for mixing ingredients. Typically, the tanks are cleaned, for example, rinsed, soaped and/or sanitized according to know procedures, prior to use and between uses. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water-jacketed tank. The temperature of the water-jacketed tank is controlled through the water-jacket, for example, to heat the contents, for example, while mixing.

As used herein, transfer means refers to any equipment, combination of equipment and/or system that can be used to transfer liquid, for example, from one tank to another tank (e.g. from the mixing tank to the packaging/holding tank), in the provided methods for making the compositions. Exemplary of the transfer means are a transfer pump and appropriate fittings, for example, sanitary fittings, ball valves and transfer hoses, for example, food grade hoses.

As used herein a mixer is any piece of equipment or combination of equipment that can be used to mix ingredients in the provided methods for making the compositions, for example, standard mixers and homoginizers (shears). For example, mixers can be used to mix the ingredients of the compositions.

As used herein, standard mixers are mixers that are used to combine a group of ingredients, or to mix one or more ingredients with a liquid, for example, with an emulsion, for example, to mix additional ingredients with the emulsion. Standard mixers can be any mixers that move the material, for example, the ingredients, during heating, for example, to promote dissolving of the ingredients.

As used herein, "homogenizer" and "shear" are used to refer to mixers with high shear, that typically are used after mixing the ingredients, for example, the ingredients of the pre-emulsion compositions. The homogenizers typically are capable of high-shear mixing, which can emulsify imiscible phases, e.g. phases of an emulsion, e.g. water/oil phases.

As used herein, a cooling apparatus is any piece of equipment or combination of equipment that can be used with the provided methods to cool the compositions and phases and ingredients thereof, for example, during mixing and/or homogenizing.

Exemplary of the cooling apparatuses are coolers (chillers), for example, recirculating coolers which can be attached, for example, to a tank, for example, remotely or by a tank mounted in the cooler, to recirculate fluid from the tank, through the chiller and back to the tank, in order to rapidly cool and maintain the temperature of a mixture during mixing. Typically, the cooling apparatus can be used to cool a liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., typically between 35° C. and 43° C., for example, 26.5° C.

As used herein, rapid cooling refers to a process by which a composition, for example, a liquid composition, for example, a forming emulsion, is cooled to a desired temperature, for example, between 25° C. or about 25° C. and 45° C. or about 45° C., typically between 35° C. and 43° C., for example, 26.5° C., in less than 2 hours or about 2 hours, typically less than 1 hour or about 1 hour, for example, in at least between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

As used herein, low heat refers to a temperature between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., for example, not more than 85° C. or about 85° C., typically not more than 60° C. or about 60° C., typically, 60° C. or about 60° C. In the provided methods for making the pre-emulsion compositions, the ingredients typically are heated, using low heat, in order to preserve the ingredients, for example, in order to prevent oxidation of the ingredients, for example, the non-polar active ingredients, for example, the omega-3 containing compounds, for example, the DHA.

As used herein, "consisting essentially of," means containing the following list of ingredient(s), and not including any additional active ingredient, for example, not including any additional active drug or pharmaceutical. For example, a composition, for example, a pre-emulsion composition, consisting essentially of a listed plurality of ingredients contains those particular ingredients and does not contain any additional active drug or pharmaceutical.

B. Compositions Containing Non-Polar Compounds

Provided herein are compositions containing non-polar compounds and methods for making the compositions. Non-polar compounds are poorly water soluble (e.g. having low water solubility or being water-insoluble). Generally, because of this poor water solubility, it can be difficult to formulate non-polar compounds into compositions for human consumption, particularly aqueous compositions, for example, foods and beverages. Poor water solubility also can contribute to poor bioavailability of non-polar compounds. Improved methods and compositions for formulating non-polar compounds are needed.

Emulsions (e.g. oil-in-water emulsions) have been used to disperse non-polar compounds in aqueous liquids. In general, emulsions are colloidal dispersions of two immiscible liquids (e.g. oil and water or other aqueous liquid), containing a continuous and a dispersed phase. In an oil-in-water emulsion, the dispersed phase is an oil phase and the continuous phase is an aqueous (water) phase. There remains a need, however, for improved emulsions (e.g. oil-in-water emulsions) containing non-polar compounds in aqueous liquids, and methods and compositions for generating the improved emulsions. In particular, emulsions are needed that are more suitable and desirable for human consumption of the non-polar compounds, for example, in foods and beverages. For example, emulsions having improved clarity (e.g. small particle size, low turbidity), stability (e.g. lack of separation), taste and smell, are needed.

Among the provided compositions are improved emulsions (e.g. liquid dilution compositions). Emulsions are provided that contain the non-polar compounds dispersed in aqueous liquid and have desirable properties, including improved clarity, stability, smell and taste. Also provided are compositions that can be diluted to generate the emulsions (e.g. pre-emulsion compositions). The provided compositions and methods for making the compositions can be used to formulate any non-polar compound in aqueous compositions.

Typically, the provided emulsions containing the non-polar compounds (e.g. the liquid dilution compositions) are nanoemulsions, which are emulsions having dispersed droplets (particles) with diameters less than 1000 nm or less than about 1000 nm, typically, less than 500 nm or less than about 500 nm, typically less than 300 or about 300 nm, typically less than 250 or less than about 250 nm, typically less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the provided nanoemulsion compositions are oil-in-water nanoemulsions, containing the non-polar compounds dispersed in aqueous liquid. The provided emulsion compositions are stabilized by one or more surfactants and/or co-surfactants and/or emulsion stabilizers. Surfactants form an interfacial film in the emulsion, between the oil and water phase, providing stability. Typically, the nanoemulsions of the provided compositions contain micelles, in which one or more surfactant surrounds the non-polar active compound. The micelles are dispersed in the water phase. Exemplary of the nanoemulsions are liquid dilution compositions, including aqueous dilution compositions, for example, clear aqueous compositions containing the non-polar compounds. Typically, the liquid dilution compositions are made by diluting one or more of the provided pre-emulsion composition compositions.

Also among the provided compositions are pre-emulsion compositions containing the non-polar compounds, which can be diluted to make the nanoemulsions, e.g. the liquid dilution compositions. The pre-emulsion compositions can be diluted, according to the provided methods, to form dilution compositions, for example, aqueous liquid dilution compositions. Typically, the pre-emulsion compositions are solid pre-emulsion compositions, which are not liquid (or gas) at room temperature (e.g. 25° C. or about 25° C.). Typically the solid pre-emulsion compositions have a waxy consistency at room temperature, and become liquid when heated, for example, when heated to 120° F., or about 120° F. 125° F., or about 125° F., or 145° F., or about 145° F., 50° C. or about 50° C., 60° C. or about 60° C. Typically, the solid pre-emulsion compositions are non-aqueous, containing none or very little hydrophilic ingredient, for example, containing less than 5% or about 5%, by weight, hydrophilic ingredients, for example, less than 4% or about 4%, less than 3% or about 3%, less than 2% or about 2%, less than 1% or about 1%, or 0% or about 0%, by weight, hydrophilic ingredient(s).

The pre-emulsion compositions can be diluted, according to the provided methods, into a medium, for example, an aqueous medium for example, a beverage, to form a liquid dilution composition (e.g. aqueous liquid dilution composition) containing the non-polar compound.

The compositions can be made using any non-polar compound. Exemplary of non-polar compounds that can be used in the provided compositions are non-polar active ingredients, for example, pharmaceuticals, nutraceuticals, vitamins and minerals. Exemplary of non-polar active ingredients are Polyunsaturated Fatty Acids (PUFA)-containing compounds, for example, omega-3-containing active ingredients, for example, compounds containing ALA, DHA and/or EPA, for example, oils derived from fish and microalgae, krill and/or flaxseed extract, and omega-6-containing non-polar active ingredients, for example, gamma-linolenic acid (GLA)-containing compounds, for example, borage oil; saw palmetto oil-containing compounds; conjugated fatty acid containing-ingredients, for example, Conjugated Linoleic acid (CLA)-containing compounds; coenzyme Q-containing active ingredients, for example, Coenzyme Q10 (CoQ10), typically oxidized CoQ10 (ubidicarenone)-containing compounds; and compounds containing phytosterols (plant sterols). Additional exemplary non-polar active ingredients are described herein. Any non-polar compound can be used in the provided compositions.

1. Pre-emulsion Compositions Containing the Non-polar Compounds

Exemplary of the provided compositions are pre-emulsion compositions containing one or more non-polar compounds. Typically, the pre-emulsion compositions are solid compositions, which typically have a waxy consistency, for example, the consistency of a substance such as wax, for example, a lip balm, at room temperature, for example, at 25° C. or about 25° C., and become liquid at higher temperatures, for example when heated to higher temperatures, for example, to 125° F. or about 125° F., or to 50° C. or about 50° C. or to 60° C. or about 60° C.

The pre-emulsion compositions can be diluted into aqueous media, using the provided methods, to form the provided liquid dilution compositions containing the non-polar compounds. The pre-emulsion compositions are formulated such that dilution of the compositions, for example, in aqueous media, yields a composition having one or more desirable properties, for example, clarity; safety; taste; smell; stability, for example, lack of phase separation, "ringing" and/or precipitation over time; and/or bioavailability. In one example, the desirable property is the ability of the provided pre-emulsion composition to yield a clear or partially clear aqueous liquid dilution composition when it is diluted into aqueous medium, for example, a beverage such as water. In another example, the desirable property relates to the safety of the pre-emulsion compositions and/or the desirability of the pre-emulsion compositions for human consumption, for example, in foods and beverages. In another example, it can be desirable that the pre-emulsion composition contains less than or equal to a particular concentration of one or more ingredients. In another example, it can be desirable that the pre-emulsion composition contains greater than or equal to a particular concentration of one or more ingredients.

In addition to the non-polar compounds, the pre-emulsion compositions contain at least one surfactant. Typically, the surfactant has an HLB value between 14 or about 14 and 20 or about 20, for example, 14, 15, 16, 17, 18, 19, 20, about 14, about 15, about 16, about 17, about 18, about 19 or about 20. Exemplary of suitable surfactants are tocopherol polyethylene glycol succinate (TPGS) and other surfactants having similar properties to TPGS, for example, other surfactants having HLB values between 14 or about 14 and 20 or about 20. Typically, the surfactant is a natural surfactant, for example, a surfactant that is GRAS (generally recognized as safe) by the FDA and/or Kosher certified, for example, TPGS.

Typically, the pre-emulsion compositions further contain one or more additional ingredients. Exemplary of additional ingredients that can be included in the pre-emulsion compositions are preservatives, solvents, co-surfactants, emulsion-stabilizers and flavoring agents, as described herein.

Typically, the pre-emulsion compositions are formulated such that, when diluted into an aqueous medium (e.g. water), they yield a dilution composition that is a nanoemulsion, in which the non-polar compound(s) are present in micelles. These micelles, containing the non-polar compound surrounded by the one or more surfactants, facilitate the dispersion of the non-polar compound among the polar solvent(s) of the aqueous medium in the dilution compositions. Typically, the pre-emulsion compositions are formulated such that the micelles in the dilution composition have a small or relatively small particle size, for example, less than 1000 or about 1000 nm, less than 500 or about 500 nm, typically less than 300 or about 300 nm, typically less than 250 or about 250 nm, typically less than 200 or about 200 nm, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with increased clarity of the dilution compositions that result from diluting the pre-emulsion compositions. For example, a liquid with a smaller particle size is more clear than a liquid with a larger particle size. Small particle size also can contribute to other desirable properties, for example, stability.

A number of parameters of the pre-emulsion compositions, including ingredients, their relative concentrations, and methods for making the pre-emulsion compositions, affect the particle size of the dilution compositions made by diluting the pre-emulsion compositions. By extension, these parameters of the pre-emulsion compositions also affect the desirable properties of the dilution compositions, for example, the clarity of the dilution compositions. In particular, the nature of the surfactant, particularly the HLB of the surfactant, and the relative concentrations of the surfactant and the non-polar compound in the pre-emulsion composition, contribute to small particle size and clarity of the dilution compositions. Typically, several of these parameters and properties relate to one another. For example, several of the parameters contribute to the particle size, typically small particle size. Particle size contributes directly to clarity of the aqueous liquid dilution compositions containing the pre-emulsion compositions. Particle size also can relate to other properties, for example, stability, lack of "ringing" and/or precipitate formation of the aqueous liquid dilution compositions containing the pre-emulsion compositions.

Accordingly, properties of the ingredients and their relative concentrations in the pre-emulsion compositions are important for the ability of the pre-emulsion composition to yield desirable dilution compositions. Determining the appropriate ingredients, and relative concentrations thereof, that will yield dilution compositions having desirable properties, is carried out using provided methods for formulating the pre-emulsion compositions.

a. Formulating the Pre-emulsion Compositions

Using the provided formulation methods, the pre-emulsion compositions are formulated by selecting ingredients and concentration ratios of the ingredients that yield compositions having one or more desired properties. When formulating the pre-emulsion compositions, selected ingredients and starting concentrations are used to make initial pre-emulsion compositions, which typically are diluted, evaluated and modified, if necessary.

As a first step in formulating the provided pre-emulsion compositions, one or more initial pre-emulsion compositions are made and evaluated for desired properties. For this step, ingredients are selected, for example, from one or more of the lists of ingredients provided below. A starting concentration (weight percentage) of each selected ingredient is selected from within an appropriate concentration range for that ingredient or category of ingredient. For example, a starting surfactant concentration is selected from within an appropriate surfactant concentration range. In some cases, the initial pre-emulsion composition is formulated based on the ingredients, and concentrations thereof, of an existing pre-emulsion composition, having one or more desired properties.

The initial pre-emulsion composition(s) then is made, using the methods for making the pre-emulsion compositions, provided below, adding each ingredient at its starting concentration at the appropriate step. In one example, more than one initial pre-emulsion composition is made. For example, multiple initial pre-emulsion compositions, each having a different concentration of one or more ingredients, can be made and compared. For example, multiple initial pre-emulsion compositions can be made in order to test various representative concentrations within an appropriate concentration range for one or more particular ingredient.

In a typical example, the initial pre-emulsion composition is made by including at least one surfactant, having an HLB value between 14 or about 14 and 20 or about 20, typically a tocopherol polyethylene glycol succinate (TPGS) surfactant.

In one example, the starting concentration of the surfactant is greater than 50% or about 50%, typically greater than 60% or about 60%, typically greater than 65% or about 65%, for example, greater than 70% or about 70%, for example, a starting concentration within the concentration range of between 50% or about 50% and 95% or about 95%, between 60% or about 60% and 95% or about 95%, typically between 65% or about 65% and 90% or about 90%, for example, between 69% or about 69% and 90% or about 90%, for example, between 69% or about 69% and 89% or about 89%, for example, 65, 66, 67, 68, 69, 69.5, 69.9, 70, 71, 72, 73, 74, 75, 76, 77, 78, 79, 79.5, 79.9, 80, 81, 82, 83, 84, 85, 86, 87, 88, 89, 89.5, 89.9, or 90%, by weight, of the composition.

In another example, the starting concentration of the surfactant is greater than 20% or about 20%, typically greater than 30% or about 30%, for example, between 30% or about 30% and 55% or about 55%, for example, between 30% or about 30% and 50% or about 50%, for example, between 30% or about 30% and 45% or about 45%, for example, 30, 31, 32, 33, 34, 35, 36, 37, 38, 39, 40, 41, 42, 43, 44, 45, 46, 47, 48, 49, 50, 51, 52, 53, 54, 55%, by weight, of the composition. This example is typically used for pre-emulsion compositions where the non-polar active ingredient includes a phytosterol.

Also in this typical example, the initial pre-emulsion composition further includes at least one non-polar compound (e.g. non-polar active ingredient). In one example, the starting concentration of the non-polar compound (e.g. active ingredient), or the total of all the one or more non-polar compounds, is chosen from within a concentration range of between 5% or about 5% and 35% or about 35%, typically between 10% or about 10% and 30% or about 30%, for example, between 10% or about 10% and 20% or about 20%, or between 20% or about 20% and 30% or about 30%, for example, 5, 6, 7, 8, 9, 10, 11, 12, 13, 14, 15, 16, 17, 18, 19, 20, 21, 22, 23, 24, 25, 26, 27, 28, 29, or 30%, by weight, of the composition.

In another example, the starting concentration of the non-polar compound (e.g. active ingredient), or the total of all the one or more non-polar compounds, is chosen from within a concentration range of between 1% or about 1% and 50% or about 50%. In this example, which typically is used when using more than one non-polar active ingredient, the total concentration of the non-polar compounds is chosen from within a concentration range of between 30% or about 30% and 55% or about 55%, for example between 40% or about 40% and 50% or about 50%, by weight, of the composition. Exemplary of starting concentrations for individual non-polar active ingredients used in this example are between 1% and 50%, for example, 1%, 10.5%, 34%, 45%, by weight of the composition, and other concentrations within the range.

In one example, the initial pre-emulsion composition further includes other ingredients, for example, preservative(s), for example, benzyl alcohol; co-surfactant(s), for example, a phospholipid, for example, phosphatidylcholine; a solvent, for example, an oil, and/or an emulsion stabilizer. Typically, water is not added as an ingredient to the pre-emulsion composition.

After making the initial pre-emulsion composition(s), the pre-emulsion composition(s) is evaluated for one or more desired properties, for example, the ability to form dilution compositions (e.g. clear dilution compositions or dilution compositions having a particular turbidity value, particle size or other property). The ability to form dilution compositions having one or more properties is assessed by diluting the pre-emulsion composition in aqueous medium, for example, diluting the pre-emulsion composition in the aqueous medium at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In one example, the dilution is carried out by including one or more drops of the heated pre-emulsion composition in the aqueous medium, for example, in 25 mL or more of the aqueous medium.

After evaluation, the ingredients, and/or concentrations thereof, can be adjusted in order to generate the desired properties in the final pre-emulsion composition. Typically, the concentration of the non-polar compound and/or the surfactant is the concentration that is adjusted after evaluating the initial pre-emulsion composition. Similarly, when formulating multiple initial pre-emulsion compositions, one or more of the non-polar compound and the surfactant is/are varied among the multiple initial pre-emulsion compositions. In some cases, following evaluation, it can be determined that additional ingredients (not included in the initial formulation) are needed or desirable for achieving the desired properties of a particular pre-emulsion composition. This process can be repeated until a pre-emulsion composition having the desired property or properties is generated.

i. Common Ingredients and Typical Concentration Ranges

Each of the provided pre-emulsion compositions contains at least one compound, typically a non-polar compound (e.g. a non-polar active ingredient). Any non-polar compound can be formulated with the provided methods and pre-emulsion compositions. Several exemplary non-polar compounds that can be incorporated into the provided compositions are described herein below. Typically, the non-polar compound is a non-polar active ingredient, for example, an oil-based active ingredient, for example, a polyunsaturated fatty acid (PUFA), a coenzyme Q or a phytochemical.

In one example, for formulating the initial pre-emulsion composition, the starting concentration of the non-polar compound, or the total of all the one or more non-polar compounds, typically is chosen from within a concentration range of between 5% or about 5% and 35% or about 35%, typically between 10% or about 10% and 30% or about 30%, for example, between 10% or about 10% and 20% or about 20%, or between 20% or about 20% and 30% or about 30%, for example, 5, 6, 7, 8, 9, 10, 11, 12, 13, 14, 15, 16, 17, 18, 19, 20, 21, 22, 23, 24, 25, 26, 27, 28, 29, or 30%, by weight, of the composition. In another example, the starting concentration of the non-polar compound (e.g. active ingredient), or the total of all the one or more non-polar compounds, is chosen from within a concentration range of between 1% or about 1% and 50% or about 50%. In this example, which typically is used when using more than one non-polar active ingredient, the total concentration of the non-polar compounds is chosen from within a concentration range of between 30% or about 30% and 55% or about 55%, for example between 40% or about 40% and 50% or about 50%, by weight, of the composition. Exemplary of starting concentrations for individual non-polar active ingredients used in this example are between 1% and 50%, for example, 1%, 10.5%, 34%, 45%, by weight of the composition, and other concentrations within the range.

In addition to the non-polar compound, the pre-emulsion compositions contain at least one surfactant. The surfactant has an HLB value of between 14 or about 14 and 20 or about 20, for example, 14, 15, 16, 17, 18, 19 or 20, or about 14, about 15, about 16, about 17, about 18, about 19, about 20, typically between 16 or about 16 and 18 or about 18. Exemplary of suitable surfactants are tocopherol polyethylene glycol succinate (TPGS) and other surfactants having similar properties, for example, any surfactant having an HLB value between 14 or about 14 and 20 or about 20. Surfactants, HLB values, and methods for determining HLB values are well known. Typically, the surfactant is a natural surfactant, which is safe and/or approved for human consumption. Exemplary of such a natural surfactant is TPGS.

In one example, the starting concentration of the surfactant is greater than 50% or about 50%, typically greater than 60% or about 60%, typically greater than 65% or about 65%, for example, greater than 70% or about 70%, for example, a starting concentration within the concentration range of between 50% or about 50% and 95% or about 95%, between 60% or about 60% and 95% or about 95%, typically between 65% or about 65% and 90% or about 90%, for example, between 69% or about 69% and 90% or about 90%, for example, between 69% or about 69% and 89% or about 89%, for example, 65, 66, 67, 68, 69, 69.5, 69.9, 70, 71, 72, 73, 74, 75, 76, 77, 78, 79, 79.5, 79.9, 80, 81, 82, 83, 84, 85, 86, 87, 88, 89, 89.5, 89.9, or 90%, by weight, of the composition.

In another example, the starting concentration of the surfactant is greater than 20% or about 20%, typically greater than 30% or about 30%, for example, between 30% or about 30% and 55% or about 55%, for example, between 30% or about 30% and 50% or about 50%, for example, between 30% or about 30% and 45% or about 45%, for example, 30, 31, 32, 33, 34, 35, 36, 37, 38, 39, 40, 41, 42, 43, 44, 45, 46, 47, 48, 49, 50, 51, 52, 53, 54, 55%, by weight, of the composition. This example is typically used for pre-emulsion compositions where the non-polar active ingredient includes a phytosterol.

One or more, typically more than one, additional ingredients can be added to the initial pre-emulsion composition. For example, the pre-emulsion compositions typically contain at least one preservative, typically a natural preservative, for example, benzyl alcohol. Exemplary of other additional ingredients that can be added to the pre-emulsion compositions, including the initial pre-emulsion compositions, are emulsion stabilizers, for example, a blend of gums; a solvent for the non-polar compound, for example, an oil other than the non-polar compound, for example, vitamin E oil or flax seed oil; a pH adjuster, for example, citric acid, or phosphoric acid; one or more flavoring agents, for example, D-limonene or lemon oil; a co-surfactant, for example, a phospholipid, for example, phosphatidylcholine.

The appropriate concentration ranges for the additional ingredients are described in individual sections below. Typically, the concentration of the additional ingredients depends, in part, on the concentrations of the non-polar active ingredient and/or of the surfactant. Typically, the concentrations of these three ingredients are the focus of the formulating methods. For example, when it is determined that modifications to ingredient concentrations in the initial pre-emulsion composition should be made, it typically is the concentrations of one or more of these two ingredients that is/are adjusted.

In one example, it can be desirable to add one or more of the additional ingredients after evaluation of the initial pre-emulsion composition, for example, in order to improve the pre-emulsion composition with respect to one or more desired properties.

ii. Evaluation of the Initial Pre-emulsion Composition

After an initial pre-emulsion composition is made according to the methods provided herein, it is evaluated based on one or more desired properties, for example, properties of an aqueous liquid dilution composition containing the diluted pre-emulsion composition, for example, clarity, color, smell, taste, safety, stability, "ringing" or forming of precipitates and/or the presence of crystals. Typically, the ability of the initial pre-emulsion composition to yield a clear (or relatively clear) liquid dilution composition upon dilution in an aqueous medium is the desired property that is evaluated. In this example, the clarity/turbidity of the diluted aqueous liquid dilution composition containing the initial pre-emulsion composition is analyzed.

For evaluation of properties of the aqueous liquid dilution composition, the initial pre-emulsion composition is diluted into an aqueous medium, typically water, for example, at a dilution factor of between 1:10 or about 1:10 and 1:1000 or about 1:1000, typically between 1:10 or about 1:10 and 1:500 or about 1:500, for example, diluted not more than 1:10 or about 1:10, at least 1:20 or about 1:20, at least 1:25 or about 1:25, at least 1:50 or about 1:50, at least 1:100 or about 1:100, at least 1:200 or about 1:200, at least 1:250 or about 1:250, at least 1:300, at least 1:400 or at least 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500. Typically, clarity of the aqueous liquid dilution composition containing the diluted initial pre-emulsion composition is evaluated using one or more approaches. Additionally, other properties can be evaluated, for example, smell and/or taste properties of the liquid, for example, when the non-polar compound is a polyunsaturated fatty acid (PUFA), particularly fish oil or algae oil, whether the aqueous liquid dilution composition smells "fishy" can be evaluated empirically.

(1) Clarity

In one example, the provided pre-emulsion compositions are formulated such that dilution of the pre-emulsion compositions in aqueous medium yields clear liquids upon dilution in aqueous medium. To evaluate the clarity of an aqueous liquid dilution composition containing the initial pre-emulsion composition, one of several approaches can be used. The clarity can be assessed by empirical observation, by measuring particle size and/or by measuring the turbidity value of the liquid.

In one example, the pre-emulsion compositions formulated such that dilution of the pre-emulsion compositions in aqueous medium yields clear liquids (or liquids that are equal in clarity to known liquids), by adding between 0.05 grams (g) or about 0.05 g and 10 g or about 10 g of the pre-emulsion composition, typically between 0.05 g and 5 g, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the pre-emulsion composition, to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound. In another example, the pre-emulsion composition can be diluted to form a clear aqueous liquid dilution composition by adding between 1 mL or about 1 mL and 10 mL or about 10 mL of the pre-emulsion composition, for example, 1 mL, 2 mL, 3 mL, 4 mL, 5 mL, 6 mL, 7 mL, 8 mL, 9 mL or 10 mL of the pre-emulsion composition to 8 fluid ounces, about 8 fluid ounces, or at least 8 fluid ounces or at least about 8 fluid ounces, for example 8, 9, 10, 11, 12, 13, 14, 15, 16, 17, 18, 19, 20, 25, 30, 35, 40, 45, 50, 100, 200 or more fluid ounces, of aqueous medium, for example, water, forming a clear aqueous liquid dilution composition that contains the non-polar compound.

In another example, the pre-emulsion composition are formulated such that dilution of the pre-emulsion compositions in aqueous medium yields a clear aqueous liquid dilution composition when at least 25 mg or about 25 mg, typically at least 35 mg, for example, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar active ingredient, is contained in at least 8 fluid ounces or at least about 8 fluid ounces of aqueous liquid dilution composition, for example, a beverage, for example, water.

In another example, the pre-emulsion compositions are formulated such that dilution of the pre-emulsion compositions in aqueous medium yields a clear aqueous liquid dilution composition at a dilution factor of between 1:10 or about 1:10 and 1:1000 or about 1:1000, typically between 1:10 or about 1:10 and 1:500 or about 1:500, for example, when diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In another example, the clear liquid is formed at dilutions less dilute than 1:10 of the pre-emulsion composition.

The provided pre-emulsion compositions can be formulated using any non-polar compound. In one example, the pre-emulsion compositions can be diluted in aqueous medium, for example, over a wide dilution range to form clear liquids, for example, at a dilution factor of between 1:10 or about 1:10 and 1:1000 or about 1:1000, typically between 1:10 or about 1:10 and 1:500 or about 1:500, for example, when diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. Typically, the clarity of the liquid is maintained with increasing dilutions, for example, to infinity.

Clarity of the aqueous liquid dilution composition can be evaluated using one of several different approaches, for example, qualitatively, by empirical evaluation, or quantitatively, by measuring particle size and/or by measuring the turbidity value of the liquid. In some examples, a particular quantitative or qualitative clarity value is desired. In another example, it can be desired that the aqueous liquid dilution composition is as clear as, less clear or more clear than another liquid, for example, an aqueous liquid dilution composition made according to the provided methods or a beverage, for example, a beverage that does not contain the pre-emulsion composition. For example, an aqueous liquid dilution composition, containing the liquid pre-emulsion composition diluted in a beverage, can be as clear or about as clear as the same beverage, containing no pre-emulsion composition. Either type of evaluation can be done qualitatively, for example by empirical observation, or quantitatively, for example, by calculating particle size and/or turbidity value (NTU) for the liquid(s).

(2) Empirical Evaluation

The relative clarity/turbidity of the aqueous liquid dilution composition containing the diluted initial pre-emulsion composition can be assessed qualitatively by observation. In one example, a clear liquid is considered clear if it does not have a cloudy appearance and/or if no particles are visible when looking at the liquid with the naked eye. Clarity can be assessed empirically by comparison to other liquids, for example, water, fruit juice, soda and/or milk.

In some cases, it is desirable that the liquid be as clear or about as clear as water or another liquid, for example a beverage. For example, it can be desired that the liquid (containing the liquid pre-emulsion composition diluted in an aqueous medium, for example, a beverage) is as clear or about as clear as the aqueous medium not containing the liquid pre-emulsion composition. In a related example, it can be desired that there is no substantial difference, for example, no observable difference, between the aqueous liquid dilution composition containing the pre-emulsion composition and the aqueous medium without the pre-emulsion composition. A clear liquid is not necessarily colorless, for example, a yellow liquid that contains no visible particles or cloudiness can be considered clear.

(3) Particle Size

Alternatively, the clarity of the aqueous liquid dilution composition containing the diluted initial pre-emulsion composition can be assessed by measuring the particle size of the liquid. Methods for measuring particle size are known. Any method for measuring particle size can be used if it is able to measure particle sizes in the appropriate ranges as described below.

For example, particle size analysis is available commercially, for example, from Delta Analytical Instruments, Inc. In one example, the particle size is measured, for example, by Delta Analytical Instruments, Inc., using a light-scattering analyzer, for example, a dynamic light scattering analyzer, for example, the Horiba® LB-550, which can measure particle sizes within a range of 0.001 micron to 6 micron and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp and can determine particle sizes from 0.02 micron to 2000 micron using Mie Theory; or other analyzers available from Delta Analytical Instruments, Inc.

Alternatively, the particle size can be measured microscopically, for example, by viewing the liquid under a microscope, for example, at 640× magnification. Using this method, particle size can be quantified by comparing to a measuring device, for example, a ruler, which is visible when viewing the liquid under the microscope. If any particles are observable at this magnification, they are measured by comparison to the measuring device. At a magnification of 640×, for example, any particle that is about 25 nm, 25 nm, or greater than 25 nm are visible. Particle sizes smaller than 25 nm are not visible at this magnification.

Typically, it is desired that the aqueous liquid dilution compositions have a particle size less than 200 nm or less than about 200 nm, for example, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, it is desired that the aqueous liquid dilution compositions have a particle size less than 100 nm or about 100 nm, less than 50 nm or about 50 nm, or less than 25 nm or about 25 nm. Typically, the particle size of the aqueous liquid dilution composition containing the pre-emulsion composition is between 5 nm or about 5 nm and 200 nm or about 200 nm, typically between 5 nm or about 5 nm and 50 nm or about 50 nm.

(4) Turbidity Measurement

Alternatively, clarity of the liquid can be analyzed by taking an optical turbidity measurement, which indicates the level of cloudiness or haziness of a liquid, which correlates to size/number of particles in suspension in the liquid. The more clear a particular liquid, the lower its turbidity value.

Turbidity can measured optically, for example, by using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light will pass through a sample with low turbidity with little disturbance. Other methods for measuring turbidity are well known and can be used with the provided methods and compositions.

The units of a turbidity value measured with a nephelometer are Nephelomtetric Turbidity Units (NTU). In one example, it is desired that the aqueous liquid dilution composition containing the diluted pre-emulsion composition has low turbidity, for example, a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0. In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid pre-emulsion composition or an aqueous liquid dilution composition made by the provided methods.

iii. Selecting a Formulation and Modifying Formulations

After evaluation of the initial pre-emulsion composition(s), either a particular formula is chosen or one or more modifications is made to the initial pre-emulsion composition formula based on the results of the evaluation. When an initial pre-emulsion composition does not display one or more desired properties, based on the evaluation, the concentration of one or more ingredients can be adjusted and another initial pre-emulsion composition made, in order to repeat the process until a pre-emulsion composition with the desired properties is made. Alternatively, alternative ingredients can be chosen. In one example, modification of the initial pre-emulsion composition involves the addition of one or more additional ingredients. For example, if evaluation reveals that the oil and water phases of the aqueous liquid dilution composition containing the diluted pre-emulsion composition are separating, an emulsion stabilizer can be added to the formulation. In another example, a co-surfactant can be added to help emulsify the components of the pre-emulsion composition.

In one example, when evaluation of the initial pre-emulsion composition reveals that it has desired properties, no modifications are made. In this example, the formula of the initial pre-emulsion composition is used for making the pre-emulsion composition. When two or more initial pre-emulsion compositions are made, for example, with increasing concentrations of an ingredient, the formula of one of the initial pre-emulsion compositions can be chosen. Which formula is chosen can be based on which formula has the most desirable property. Alternatively, desirable properties can be balanced with relative amounts of ingredients. In one example, it is desirable to choose the formulation that uses the lowest or the highest concentration of a particular ingredient but still provides a pre-emulsion composition that yields a clear liquid upon dilution in an aqueous medium. In one example, the desired formulation is the formulation that has the lowest concentration of the surfactant, while still providing a pre-emulsion composition that yields a clear liquid upon dilution in an aqueous medium. In another example, the desired formulation is the formulation that has the highest concentration of the non-polar active ingredient, while still providing a pre-emulsion composition that yields a clear liquid upon dilution into an aqueous medium. In another example, the formulation that yields the clearest liquid is desired.

In another example, however, modifications are made to the formula even if the initial pre-emulsion composition bears desired properties. For example, upon determining that a particular pre-emulsion composition formulation results in desired properties, it can be desirable to modify the concentration of one or more ingredients to determine whether the same desired properties can be achieved if a higher or lower concentration of the ingredient(s) is used. For example, it can be desirable to determine the lowest concentration of surfactant that can be used, while still generating a pre-emulsion composition with a desired property, for example, the ability to form a clear liquid upon dilution in an aqueous medium. In another example, it can be desirable to determine the highest concentration of the non-polar ingredient that can be incorporated into a pre-emulsion composition, while still maintaining the desired property, for example, the ability of the pre-emulsion composition to form a clear liquid upon dilution in an aqueous medium. In another example, one or more additional ingredients can be added after making an initial pre-emulsion composition with desirable properties, for example, flavoring agents and/or pH adjusting agents.

b. Non-Polar Compounds

The pre-emulsion compositions contain one or more non-polar compounds. Non-polar compounds include any lipophilic or lipid soluble compounds, for example, active ingredients, that have greater solubility in organic solvents (e.g. ethanol, methanol, ethyl ether, acetone, and benzene) and in fats and oils, than in aqueous liquid dilution compositions, for example, water. Typically, the non-polar compounds used in the provided compositions are poorly water soluble, for example, water insoluble or compounds having low water solubility.

Non-polar compounds include drugs, hormones, vitamins, nutrients and other lipophilic compounds. Exemplary non-polar compounds are listed hereinbelow. The provided methods can be used to make pre-emulsion compositions that can be diluted (e.g. dissolved/dispersed) in aqueous medium, using any non-polar compound. In one example, the non-polar compound is not tocopheryl polyethylene glycol succinate (TPGS). In another example, the non-polar compound is not Vitamin E. Exemplary of non-polar compounds that can be used in the provided pre-emulsion compositions are:

Non-polar ingredients containing essential fatty acids, for example, polyunsaturated fatty acids (PUFAs), for example, gamma-linolenic acid (GLA), for example, borage oil and evening primrose (*Oenothera biennis*) oil, blackcurrant seed oil, hemp seed oil, and spirulina extract; compounds containing omega-3 fatty acids, for example, natural and synthetic omega-3 fatty acids, for example, compounds containing omega-3 polyunsaturated long-chain fatty acids, including Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and/or nisinic acid (24:6ω3), for example, fish oil, algae oil, krill oil, canola oil, flaxseed oil, soybean oil and walnut oil; compounds containing short-chain omega-3 fatty acids, for example, Alpha-Linolenic acid (α-Linolenic acid; ALA) (18:3ω3) and Stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), for example, highly pourified fish oil pre-emulsion compositions, perilla oil, krill oil, and algae oil, for example, microalgae oil; compounds containing omega 6 fatty acids, for example, compounds containing Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and/or Docosapentaenoic acid (22:5ω6), for example, borage oil, corn oil, cottonseed oil, grapeseed oil, peanut oil, primrose oil, for example, evening primrose Oenothera biennis) oil, blackcurrant seed oil, hemp seed oil, spurulina extract, safflower oil, sesame oil and soybean oil. Exemplary of a safflower oil that can be used with the provided compositions is the high linoleic safflower oil, distributed by Jedwards, International, Inc., Quincy, MA, which contained between 5% and 10% (e.g. 6.65%) C:16 Palmitic acid, between 1% and 3% (e.g. 2.81%) C:18 Stearic acid, between 12% and 18% (e.g. 14.65%) 18:1 Oleic acid, between 70% and 80% (e.g. 74.08%) C18:2 Linoleic acid and less than 1% (e.g. 0.10%) C18:3 Linolenic acid;

Other fatty acids, for example, triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; and ethyl linoleate; and herb oils, for example, garlic oils and scordinin; short-chain saturated fatty acids (4:0-10:0), Lauric acid (12:0), Myristic acid (14:0), Pentadecanoic acid (15:0), Palmitic acid (16:0), Palmitoleic acid (16:1 ω7), Heptadecanoic acid (17:0), Stearic acid (18:0), Oleic acid (18:1 ω9), Arachidic acid (20:0);

Micronutrients, for example, vitamins, minerals, co-factors, for example, Coenzyme Q10 (CoQ10, also called ubiquinone), ubiquinol, tumeric extract (cucuminoids), saw palmetto lipid extract (saw palmetto oil), exhinacea extract, hawthorne berry extract, ginseng extract, lipoic acid (thiotic acid), acsorbyl palmitate, kava extract, St. John's Wort (hypericum, Klamath weed, goat weed), extract of quercitin, dihydroepiandrosterone, indol-3-carbinol;

Carotenoids, including hydrocarbons and oxygenated, alcoholic derivatives of hydrocarbons, for example, beta carotene, mixed carotenoids complex, leutein, lycopene, Zeaxanthin, Cryptoxanthin, for example, beta-crytoxanthin, astaxanthin, bixin, canthaxanthin, capsanthin, capsorubin, apo-carotenal, beta-12'-apo-carotenal, "Carotene" (mixture of alpha and beta-carotene), gamma carotene, ciolerythrin, esters of hydroxyl- or carboxyl-containing members thereof;

Fat-soluble vitamins, for example, Vitamins A, D, E and K, and corresponding provitamins and vitamin derivatives such as esters with an action resembling that of vitamin A, D, E or K for example; retinol (vitamin A) and pharmaceutically acceptable derivatives thereof, for example, palmitate ester of retinol and other esters of retinol, and calciferol (vitamin D) and its pharmaceutically acceptable derivatives thereof and precursors of vitamin D, d-alpha tocopherol (vitamin E) and derivatives thereof, including pharmaceutical derivatives thereof, for example, Tocotrienols, d-alpha tocopherol acetate and other esters of d-alpha tocopherol, and ascorbyl palmitate, a fat-soluble version of vitamin C;

Phytochemicals, including phytoestrogens, for example, genistein and daidzein, for example, isoflavones, for example, soy isoflavones, flavonoids, phytoalexins, for example, Resveratrol (3,5,4'-trihydroxystilbene), red clover extract, and phytosterols;

Lipid-soluble drugs, including natural and synthetic forms of immunosuppressive drugs, such as Cyclosporin, protease inhibitors such as Ritonavir, macrolide antibiotics and oil soluble anesthetics such as Propofol, natural and synthetic forms of steroidal hormones, for example, estrogens, estradiols, progesterone, testosterone, cortisone, phytoestrogens, dehydroepinadrosterone (DHEA), growth hormones and other hormones;

Oil-soluble acids and alcohols, for example, tartaric acid, lactylic acid butylated hydroxyanisole, butylated hydroxytoluene, lignin, sterols, polyphenolic compounds, oryzanol, cholesterol, phytosterols, flavonoids, such as quercetin and reservatol, diallyl disulfides and the like.

i. Polyunsaturated Fatty Acid (PUFA)-containing Active Ingredients

Exemplary of the non-polar compounds contained in the pre-emulsion compositions are compounds containing fatty acids, for example, active ingredients containing polyunsaturated fatty acids (PUFAs). Fatty acids are straight-chain hydrocarbon molecules with a carboxyl (COOH) group at one end of the chain. PUFAs are fatty acids that contain more than one carbon-carbon double bond in the carbon chain of the fatty acid. PUFAs, particularly essential fatty acids, are useful as dietary supplements.

Different nomenclatures can be used to describe fatty acid molecules. Lipid nomenclature, for example, 18:3 ω-3, indicates the carbon chain length, number of double bonds and the position along the carbon chain of the first carbon-carbon double bond in a fatty acid. Using this nomenclature, each carbon along the chain is labeled according to its position relative to one end of the chain. For example, the first carbon away from the carboxylate end is named α, the second is named β, and so forth. The last carbon in the molecule (furthest from the carboxy group) always is labeled ω (or omega, or n). The number of carbons and the number of double bonds are listed first in the lipid name of a fatty acid, separated by a colon. For example, the name "18:3" indicates that the molecule has eighteen (18) carbons and three (3) double bonds. Following these numbers, the position at which the first double bond appears, relative to the last (ω) carbon, is listed. For example, the nomenclature, 18:3 ω-3 (or 18:3 omega-3; or 18:3 n-3), describes a fatty acid with eighteen (18) carbons and three (3) double bonds, the first of which occurs at the third carbon away from the omega carbon.

Alternatively, chemical nomenclature can be used. The chemical name of a fatty acid describes the position of each double bond. In the chemical naming, the carbons are numbered, beginning with 1, starting with the carbon that is part of the carboxy (COOH) group. Thus, with this numbering system, the α carbon is labeled "2." The chemical name of the fatty acid lists the first carbon (from the COOH end) to participate in each double bond.

Certain PUFAs are called essential fatty acids because mammals, including humans, cannot synthesize them using any known chemical pathway, and must obtain them from diet or by supplementation. (U.S. Pat. No. 6,870,077; Covington, *American Family Physician* (2004), 70(1): 133-140). The essential PUFAs are the omega-3 (6)$_3$; n-3) fatty acids and the omega-6 (ω-6; n-6) fatty acids. Both omega-3 and omega-6 fatty acids are methylene interrupted polyenes, which have two or more cis double bonds, separated by a single methylene group. Exemplary of Omega-3 fatty acids are Alpha-Linolenic acid (α-Linolenic acid; ALA) (18:3ω3) (a short-chain fatty acid); Stearidonic acid (18:4ω3) (a short-chain fatty acid); Eicosapentaenoic acid (EPA) (20:5ω3); Docosahexaenoic acid (DHA) (22:6ω3); Eicosatetraenoic acid (24:4ω3); Docosapentaenoic acid (DPA, Clupanodonic acid) (22:5ω3); 16:3 ω3; 24:5 ω3 and nisinic acid (24:6ω3). Longer chain Omega-3 fatty acids can be synthesized from ALA (the short-chain omega-3 fatty acid). Exemplary of Omega-6 fatty acids are Linoleic acid (18:2ω6) (a short-chain fatty acid); Gamma-linolenic acid (GLA) (18:3ω6); Dihomo gamma linolenic acid (DGLA) (20:3ω6); Eicosadienoic acid (20:2ω6); Arachidonic acid (AA) (20:4ω6); Docosadienoic acid (22:2ω6); Adrenic acid (22:4ω6); and Docosapentaenoic acid (22:5ω6).

While the longer chain Omega-3 and Omega-6 essential fatty acids can be synthesized from ALA (the short-chain omega-3 fatty acid) and Linolenic acid (LA), respectively, evidence suggests that conversion of these short chain fatty acids in humans is slow. Thus, a major source of long chain essential PUFAs is dietary, (see, e.g., Ross et al.,*Lipids in Health and Disease* (2007), 6:21; Lands, *The FASEB Journal* (1992), 6(8): 2530). Dietary supplements containing PUFAs, particularly essential PUFAs, are desirable for protection against cardiovascular disease, inflammation and mental illnesses, (see, e.g., Ross et al., *Lipids in Health and Disease* (2007), 6:21; Lands, *The FASEB Journal* (1992), 6(8): 2530; U.S. Pat. No. 6,870,077). Evidence suggests that essential fatty acids, particularly EPA and DHA, in the form of food and nutritional supplements, play a role in preventing a number of disease states, including cardiovascular diseases, inflammation, mental health and behavioral diseases and disorders, (see, e.g., Ross et al.,*Lipids in Health and Disease* (2007), 6:21; Lands, The FASEB Journal (1992), 6(8): 2530; U.S. Pat. No. 6,870,077; Covington, *American Family Physician* (2004), 70(1): 133-140).

Omega-9 fatty acids are non-essential PUFAs. Exemplary of omega-9 fatty acids are Oleic acid (which is monounsaturated) (18:1 ω9); Eicosenoic acid (20:1 ω9); Mead acid (20:3 ω9); Erucic acid (22:1 ω9); and Nervonic acid (24:1 ω9).

Conjugated fatty acids are PUFAs with two or more conjugated double bonds. Conjugated fatty acids can be used as nutritional supplements. Exemplary of conjugated fatty acids are Conjugated Linoleic acid (CLA), for example, 18:2 ω7, 18:2 ω6; Conjugated Linolenic acid, for example, 18:3ω6, 18:3ω; and other conjugated fatty acids, for example, 18:3 ω3, 18:4 ω3, and 20:5 ω6.

(1) Omega-3 Fatty Acid Compounds

Exemplary of the PUFA-containing active ingredients that can be used in the provided compositions are compounds that contain one or more omega-3 (ω3; n-3) fatty acids, for example, compounds containing DHA and/or EPA fatty acids, for example, marine oils, for example, fish oil, krill oil and algae oil; and compounds containing ALA fatty acids, for example, flax seed oil.

Typically, oils and aqueous compositions containing long-chained polyunsaturated fatty acids (PUFA) are susceptible to oxidation, making them unstable and giving them an unpleasant taste. The ingredients and relative concentrations thereof, as well as the methods for making the pre-emulsion compositions, contribute to desirable properties of DHA/EPA-containing pre-emulsion compositions. In one example, ingredients and methods minimize the "fishy" odor and/or taste of DHA/EPA compositions and increase their stability over time. In one aspect, the compounds in the pre-emulsion compositions have low oxidation, contributing to these desirable properties.

(a) DHA/EPA

Exemplary of non-polar active ingredients that contain one or more omega-3 fatty acids, which can be used in the provided compositions, are compounds containing DHA and/or EPA, for example, marine oil, for example, fish oil, krill oil and algae oil. Any oil containing DHA and/or EPA can be used. In one example, the non-polar active ingredient contains between 20% or about 20% and 40% or about 40% DHA. In another example, the non-polar active ingredient contains between 25% or about 25% and 35% or about 35% DHA. In another example, the non-polar active ingredient contains at least 70% or about 70%, by weight, DHA, for example, at least 75% or about 75%, at least 80% or about 80%, at least 85% or about 85%, or at least 90% or about 90%, by weight, DHA. In another example, the non-polar active ingredient contains between 5% or about 5% and 15% or about 15% EPA, for example, 5, 6, 7, 8, 9, 10, 11, 12, 13, 14 or 15%, by weight, EPA. In another example, the non-polar active ingredient contains not more than 10% or about 10% EPA or less than 10% or about 10%, EPA. In another example, the non-polar active ingredient contains DHA and EPA, for example, DHA representing at least 20% or about 20%, by weight of the non-polar active ingredient and EPA representing not more than 13% or about 13% of the non-polar active ingredient, for example, not more than 10% or about 10%, by weight of the non-polar active ingredient. In another example, the non-polar active ingredient contains DHA, representing at least 35% or about 35% of the non-polar active ingredient and EPA representing not more than 13% or about 13% of the non-polar active ingredient, for example, not more than 10% or about 10% of the non-polar active ingredient. In another example, the non-polar active ingredient contains DHA and EPA, for example, DHA representing at least 70% or about 70% of the non-polar active ingredient and EPA representing not more than 13% or about 13% of the non-polar active ingredient, for example, not more than 10% or about 10% of the non-polar active ingredient.

(i) Fish Oils

Exemplary of the PUFA-containing non-polar active ingredients that can be used in the provided compositions are oils derived from fish, which contain DHA, EPA or both DHA and EPA. Particularly, cold water marine fish are a known source of Omega-3 fatty acids (U.S. Pat. No. 4,670,285). Suitable fish oil containing DHA, EPA or both DHA and EPA can be obtained from any of a number of commercial sources, for example, fish oils available from Jedwards International, Inc., any of which can be used with the provided compositions.

Fish oils typically are extracted from fish tissue, for example, frozen fish tissue. In one example, the fish oil is a tasteless fish oil, for example, a cod liver oil, which has been isolated from fish, for example, from cod liver, and then refined and deodorized, or in some other way treated so its taste becomes neutral, for example, as described in International Publication Nos. WO 00/23545 and WO 2004/098311. In one example, these fish oils are isolated from frozen fish tissue by a process that minimizes oxidation. Exemplary of such a tasteless fish oil is Denomega™ 100, Borregaard Ingredients, Sarpsborg, Norway; distributed by Denomega Nutritional Oils AS, Boulder, Colo. Typically, the tasteless fish oil, for example, cod liver oil, contains between 25% or about 25% and 35% or about 35% Omega-3 fatty acids, for example, 34% Omega-3 fatty acids. In one example, the fish oil, for example, the Denomega™ 100 oil, contains 13% or about 13% DHA and 13% or about 13% EPA.

Also exemplary of the fish oils that can be included in the provided compositions are fish oils containing high amounts of Omega-3 fatty acids, for example, high amounts of DHA. One example of such a fish oil contains at least about 85% DHA, typically greater than 85% DHA and at least about 90% Omega-3 fatty acids, typically greater than, 90% Omega-3 fatty acids. In another example, the fish oil can contain 98% PUFA, 89% Omega-3 fatty acids, about 70% DHA, about 10% EPA, 8.9% Omega-6 fatty acids and 0.7% Omega-9 fatty acids.

Exemplary of a fish oil containing high amounts of Omega-3 fatty acids that can used as the non-polar compound in the provided compositions is an Omega-3 Fish Oil EE (O3C Nutraceuticals, supplied by Jedwards International Inc., Quincy, Mass.), which contains 89% Omega-3 fatty acids, 8.9% Omega-6 fatty acids, 0.7% Omega-9 fatty acids, 0.1% saturated fatty acids, 1.0% monounsaturated fatty acids, 74.5% Docosahexanoic (DHA) fatty acids, 9.3% Eicosapentaenoic (EPA) fatty acids and 98% polyunsaturated fatty acids (PUFA). This fish oil also contains 0.1% (16:0) palmitic acid, 0.1% (16:1 ω7) palmitoleic acid, 0.1% (18:0) stearic acid, 0.6% (18:1 ω9) oleic acid, 0.1% (18:1 ω7) oleic acid, 0.3% (18:2 ω6) linoleic acid, 0.2% (18:3 ω3) linolenic acid, 0.2% (18:4 ω3) octadecatetraenoic acid, 0.1% (20:1 ω9) eicosanoic acid, 0.1% (20:2 ω6) eicosadienoic acid, 0.2% (20:3 ω6) Eicosatrienoic Acid, 2.4% (20:4 ω6) arachidonic acid, 0.6% (20:4 ω3) arachidonic acid, 0.1% (22:1 ω11) erucic acid, 0.6% (21:5 ω3) uncosapentaenoic acid, 0.5% (22:4 ω6) docosatetraenoic acid, 5.4% (22:5 ω6) docosapentaenoic acid, 3.6% (22:5 ω3) docosapentaenoic acid and 0.9% other fatty acids.

Also exemplary of a fish oil containing high amounts of Omega-3 fatty acids that can be used in the provided compositions is Omega Pre-emulsion composition 85 DHA TG Ultra (O3C Nutraceuticals AS, Oslo, Norway), which contains greater than 85% DHA (C22:6n-3) and greater than 90% total omega-3 fatty acids and is isolated from fatty fish species Eugraulidae, Clupeidae and Scombridae families. This fish oil is produced by purifying and concentrating the oils from these fish with gentle technologies to increase the concentration of omega-3 fatty acid DHA. Any fish oil containing DHA and/or EPA can be used as the non-polar compound in the provided compositions. Also exemplary of the fish oils are other fish oils made by O3C Nutraceuticals, AS and other fish oils supplied by Jedwards, International, Inc.

Also exemplary of the fish oils are krill oils, made according to International Publication No. WO 2007/080515.

(ii) Algae Oil

Also exemplary of non-polar compounds containing Omega-3 PUFAs, particularly DHA (and optionally EPA), that can be used as the non-polar compound in the provided compositions are oils derived from microorganisms, for example, oils derived from marine dinoflagellates, for example, microalgae, for example, Crypthecodinium sp, particularly, Crypthecodinium cohnii. Microalgae oils, like fish oil, are an excellent source of omega-3 fatty acids, particularly DHA (U.S. Pat. Nos. 5,397,591, 5,407,957, 5,492,938 and 5,711,983). Exemplary of oils derived from microalgae are the oils disclosed in (and oils made according to the methods described in) U.S. Pat. Nos. 5,397,591, 5,407,957, 5,492,938 and 5,711,983 and U.S. Publication number 2007/0166411, including DHASCO® and DHASCO-S® (Martek Biosciences Corporation).

Also exemplary of non-polar compounds containing Omega-3 PUFAs, particularly DHA (and optionally EPA), that can be used as the non-polar compound in the provided compositions are oils derived from microorganisms, for example, oils derived from marine dinoflagellates, for example, microalgae, for example, *Crypthecodinium sp*, particularly, *Crypthecodinium cohnii*. Microalgae oils, like fish oil, are an excellent source of omega-3 fatty acids, particularly DHA (U.S. Pat. Nos. 5,397,591, 5,407,957, 5,492,938 and 5,711,983). Exemplary of oils derived from microalgae are the oils disclosed in (and oils made according to the methods described in) U.S. Pat. Nos. 5,397,591, 5,407,957, 5,492,938 and 5,711,983 and U.S. Publication number 2007/0166411, including DHASCO® and DHASCO-S® (Martek Biosciences Corporation).

For example, U.S. Pat. No. 5,397,591 describes, inter alia, single cell edible oils (algae oils) (and methods for making the oils), which contain at least 70% triglycerides, which contain about 20-35% DHA and lack EPA, isolated from *Crypthecodinium cohnii*, preferably containing more than 70% triglycerides, having 15-20% myristic acid; 20-25% palmitic acid; 10-15% oleic acid; 30-40% DHA and 0-10% other triglycerides. U.S. Pat. No. 5,407,957 describes, inter alia, algae oils (and methods for making the oils) derived from *Crypthecodinium cohnii*, preferably containing greater than about 90% triglycerides, at least 35% DHA by weight, in one example, having 15-20 myristic acid, 20-25% palmitic acid, 10-15% oleic acid, 40-45% DHA, and 0-5% other oils. U.S. Pat No. 5,492,938 describes, inter alia, single cell edible oils (and methods for making the oils) containing at least 70% triglycerides, which contain about 20-35% DHA and lack EPA, isolated from *Crypthecodinium cohnii*, in one example containing more than 70% triglycerides, having 15-20% myristic acid; 20-25% palmitic acid; 10-15% oleic acid; 30-40% DHA; 0-10% other triglycerides. U.S. Pat. No. 5,711,983 describes, inter alia, single cell edible oils (and methods for making the oils) containing at least 70% triglycerides, which contain about 20-35% DHA and lack EPA, isolated from *Crypthecodinium cohnii*, in one example, containing more than 70% triglycerides, having 15-20% myristic acid; 20-25% palmitic acid; 10-15% oleic acid; 30-40% DHA and 0-10% other triglycerides.

Also exemplary of suitable microalgae oils are those disclosed, for example, in U.S. Pat. No. 6,977,166 and U.S. Publication No. 2004/0072330. Any oil derived from dinoflagellates, for example, microalgae, which contains DHA, and optionally EPA, is suitable as an algae oil for use with the provided compositions, for example, V-Pure algae oil (Water4Life, Switzerland, which contains EPA and DHA).

(b) Flax Seed Oil-omega 3 (ALA)

Also exemplary of the Omega-3 containing non-polar compounds used in the provided compositions is flaxseed oil (flaxseed oil, linseed oil). Flaxseed oils, which are good sources of omega-3 fatty acids, particularly alpha-linolenic acid, have been used as nutritional supplements. Flaxseed oils are produced by pressing the flax seed and refining the oil from the flax seeds. Exemplary of flaxseed oil that can be used as the non-polar compound in the provided compositions is flaxseed oil derived from *Linum usitatissimum* L., for example, flaxseed oil supplied by Sanmark LLC, Greensboro, N.C. (Sanmark Limited, Dalian, Liaoning Province, China), which contains not less than (NLT) 50% C18:3 alpha-linolenic acid, and further contains other fatty acids, for example, 3-8% C16:0 Palmitic acid, 2-8% C18:0 Stearic acid, 11-24% C18:1 Oleic acid, 11-24% C18:2 linoleic acid and 0-3% other fatty acids. Also exemplary of suitable flaxseed oil is a flaxseed oil containing 6% Palmitic acid, 2.5% stearic acid, 0.5% arachidic acid, 19% oleic acid, 24.1% linoleic acid, 47.4 linolenic acid, and 0.5% other fatty acids. The fatty acid composition of flaxseed oil can vary. Any flaxseed oil can be used as the non-polar compound in the provided compositions. In one example, the flaxseed oil contains at least 50% alpha-linolenic acid or at least about 50% alpha-linolenic acid. In another example, the flaxseed oil contains at least 65% or 70% alpha-linolenic acid or at least about 65% or about 70% alpha-linolenic acid. Exemplary of a flaxseed containing greater than 65% linolenic acid content (of total fatty acid content), for example, 70-80% or 70-75%, is the flaxseed described in U.S. Pat. No. 6,870,077.

(2) Omega-6 Compounds

Also exemplary of the non-polar compounds used in the provided compositions are compounds containing omega-6 PUFAs, for example, gamma-linolenic acid (GLA), for example, borage oil and evening primrose (*Oenothera biennis*) oil, blackcurrant seed oil, hemp seed oil, fungal oil and spirulina extract. Any oil containing omega-6 fatty acids can be used in the provided compositions.

(a) Borage Oil (Gamma-Linolenic Acid (GLA))

Exemplary of the omega-6 containing non-polar compounds are compounds containing GLA, for example, borage oil. GLA is an omega-6 PUFA, which primarily is derived from vegetable oils, for example, evening primrose (*Oenothera biennis*) oil, blackcurrant seed oil, hemp seed oil, and spirulina extract. GLA has been used as a nutritional supplement. It has been proposed that GLA has a role in treating various chronic diseases and in particular that it has anti-inflammatory effects (Fan and Chapkin *The Journal of Nutrition* (1998), 1411-1414). In one example, the non-polar active ingredient contains at least about 22% or about 22%, by weight, GLA, for example, 22, 23, 24, 25, 26, 27, 28, 29, 30, 31, 32, 33, 34, 35, 36, 37, 38, 39, 40, 50, 60, or more, %, by weight, GLA.

Borage (*Borago officinalis*), also known as "starflower" is an herb with seeds containing high amounts of GLA. Exemplary of borage oil that is used as a non-polar active ingredient in the provided compositions is the borage oil supplied by Sanmark LLC, Greensboro, N.C. (Sanmark Limited, Dalian, Liaoning Province, China), derived by pressing and isolating oil from the seeds of *Borago officinalis* L. This oil contains not less than (NLT) 22% C18:3 gamma-linolenic acid (GLA), between 9 and 12% C16:0 Palmitic acid, between 3 and 5% C18:0 Stearic acid, between 15 and 20% C18:1 Oleic acid, between 35 and 42% C18:2 linoleic acid, between 3 and 5% C20:1 Ocosenoic acid, between 1 and 4% C22:1 Docosenoic acid and between 0 and 4% other fatty acids. Other borage oils can be used. Other GLA-containing oils also can be used as the non-polar compound.

(3) Saw Palmetto Extract

Also exemplary of the non-polar compounds used in the provided compositions is saw palmetto extract, a lipophilic extract of the ripe berries of the American dwarf palm (also called *Serenoa repens* or *Sabal serrulata*), which has been used to treat genitourinary and other diseases and to enhance sperm production, breast size and libido, as a mild diuretic, a nerve sedative, an expectorant and a digestive tract tonic, and particularly to treat benign prostate hyperplasia (BHP) (Ernst, *Academia and Clinic* (2002), 136; 42-53; Gordon and Shaughnessy, *Complementary and Alternative Medicine* (2003), 76(6); 1281-1283). Saw palmetto extract is commercially available from a number of sources. Any saw palmetto lipid extract can be used in the provided compositions. Exemplary of the saw palmetto extract that can be used in the provided compositions is Saw Palmetto, Lipophilic Extract, commercially available from Natural Medicinals, Inc., Felda, Fla. This Saw Palmetto Lipophilic Extract is Carbon Dioxide extracted and, in one example, contains, 85.9% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. Other sources of saw palmetto extract can be used.

(4) Conjugated Linoleic Acid (CLA)

Also exemplary of the PUFA non-polar compounds that can be used in the provided compositions are non-polar compounds containing conjugated fatty acids. Conjugated fatty acids are PUFAs with two or more conjugated double bonds. Conjugated fatty acids can be used as nutritional supplements. Exemplary of the active ingredients containing conjugated fatty acids are compounds containing Conjugated Linoleic acid (CLA), for example, 18:2 ω7, 18:2 ω6; Conjugated Linolenic acid, for example, 18:3ω6, 18:3ω5; and other conjugated fatty acids, for example, 18:3 ω3, 18:4 ω3, and 20:5 ω6. CLA refers to a family of linoleic acid isomers found primarily in meat and dairy products of ruminants. Typically, the CLA compounds contain a mixture of different CLA isomers, for example, C18:2 CLA c9, t11, CLA t10, c12 and other CLA isomers. Exemplary of the CLA that can be used as an active ingredient in the provided compositions is CLA (80%) commercially available from Sanmark, LTD (Dalian, Liaoning Province, China; product code 01057-A80). This CLA is clear white to pale yellow oil and has the following fatty acid composition: NMT (not more than) 9.0% C16:0 Palmitic acid, NMT 4.0% Stearic acid, NMT 15.0% C18:1 Oleic acid, NMT 3.0% C18:2 Linoleic acid, NLT (not less than) 80% C18:2 CLA (including the following isomers: NLT 37.5% C18:2 CLA c9, t11, 37.5% C18:2 CLA t10, c12, and NMT 5.0% other CLA isomers); and NMT 5.0% other fatty acids. Other CLA containing compounds can be used.

ii. Coenzyme Q Active Ingredients

Exemplary of the non-polar active ingredients are compounds containing Coenzyme Q, for example, Coenzyme Q10 (also called CoQ10, ubiquinone, ubidicarenone, ubiquinol and vitamin Q10). Coenzyme Q compounds are benzoquinone compounds containing isoprenyl units. The number of isoprenyl units in each of the different CoQ species is indicated with a number following CoQ. For example, CoQ10 contains 10 isoprenyl units. Coenzyme Q10 is a predominant Coenzyme Q species.

Coenzyme Q can exist in two different forms: an oxidized form and a reduced form. When the oxidized form of a Coenzyme Q species is reduced by one equivalent, it becomes a ubisemiquinone, denoted QH, which contains a free radical on one of the oxygens in the benzene ring of the benzoquinone. Both oxidized and reduced coenzyme Q containing compounds can be used as active ingredients in the provided compositions.

(1) Coenzyme Q10

Exemplary of the Coenzyme Q containing non-polar active ingredients that can be used in the provided compositions are active ingredients containing Coenzyme Q10. Coenzyme Q10 (also called CoQ10, ubiquinone, ubidicarenone, ubiquinol, and vitamin Q10) is a benzoquinone compound that contains 10 isoprenoid units. The "Q" in the name refers to Quinone and the 10 refers to the number of isoprenoid units. CoQ10 typically refers to the oxidized form of CoQ10, which also is referred to as ubidicarenone, as opposed to the reduced form of CoQ10. In both the reduced and oxidized CoQ10 are exemplary of the coenzyme Q species that can be used as active ingredients in the provided compositions.

CoQ10 has electron-transfer ability and is present in cellular membranes, such as those of the endoplasmic reticulum, peroxisomes, lysosomes, vesicles and the mitochondria. A decrease in natural CoQ10 synthesis has been observed in sick and elderly people. Because of this observation and its potent antioxidant properties, CoQ10 is used as a dietary supplement and a treatment for diseases such as cancer and heart disease. CoQ10, however, exhibits relatively poor bioavailability.

CoQ10 containing compounds are available commercially. Any CoQ10 compound or reduced CoQ10 compound can be used with the provided composition. Exemplary of the CoQ10 compounds that can be used as active ingredients are coenzyme Q10 compounds containing greater than 98% or greater than about 98% ubidicarenone, for example, the compound sold under the name Kaneka Q10™ (USP Ubidicarenone) by Kaneka Nutrients, L.P., Pasadena, Tex. The compound sold under the name Kaneka Q10™ is fermented entirely from yeast and is identical to the body's own CoQ10 and free from the cis isomer found in some synthetically produced CoQ10 compounds. Any CoQ10 compound can be used in the provided compositions.

iii. Phytosterol-Containing Active Ingredients

Exemplary of the non-polar compounds used as active ingredients in the provided compositions are phytosterol (plant sterol)-containing compounds. Plant sterols are structurally similar to cholesterol and have been found to reduce the absorption of dietary cholesterol, which can affect the levels of serum cholesterol. According to the U.S. Food and Drug Administration (FDA), two servings per day, each containing 0.4 grams of plant sterols, for a total daily intake of at least 0.8 grams, as part of a diet low in saturated fat and cholesterol, can reduce the risk of heart disease. Thus, plant sterols are used in nutritional supplements.

Any phytosterol-containing compound can be used as an active ingredient in the provided compositions. Exemplary of the phytosterol-containing compounds that can be used as active ingredients in the provided compositions are compounds containing plant sterols, for example, the compound sold under the name CardioAid™, distributed by B&D Nutrition and manufactured by ADM Natural Health and Nutrition, Decatur, Ill. This compound contains Kosher, Pareve, and Halal plant sterols that are produced under current food GMPs. The sterols are PCR negative and the material is derived from genetically modified organisms (GMOs). This phytosterol compound contains a minimum of 95% plant sterols, which can include up to 5 plant sterols. The compound can contain, for example, 40-58% Beta sitosterol, 20-30% Campesterol, 14-22% Stigmasterol, 0-6% Brassicasterol and 0-5% Sitostanol. The compound further can contain tocopherols, for example, 0-15 mg/g tocopherols. The compound is tested and is negative for *Salmonella*, *E. coli* and *Staphylococcus aureus*.

c. Other Components of the Pre-emulsion Compositions i. Surfactants

In addition to the one or more non-polar compound(s), each of the provided compositions contains at least one surfactant. In one example, the compositions contain one or more additional surfactants, which are referred to as co-surfactants or emulsifiers.

Surfactants (and co-surfactants) are molecules that contain both hydrophobic and hydrophilic portions. In one example, the hydrophobic portion is a hydrophobic tail and the hydrophilic portion is a hydrophilic head of the surfactant molecule.

Exemplary of surfactants that can be used in the provided methods and compositions are surfactants having an HLB value of between 14 or about 14 and 20 or about 20, typically between 16 or about 16 and 18 or about 18. Exemplary of suitable surfactants include, but are not limited to, Vitamin E-derived surfactants, such as tocopherol and/or tocotrienol-derived surfactants, in which the Vitamin E moiety represents the hydrophobic region of the surfactant, and is attached, via a linker, to another moiety, such as a polyethylene glycol (PEG) moiety, that provides the hydrophilic portion of the surfactant. Vitamin-E derived surfactants include, but are not limited to, tocopherol derived surfactants, including polyalkylene glycol derivatives of tocopherol, typically polyethylene glycol (PEG) derivatives of tocopherol, such as tocopherol polyethylene glycol succinate (TPGS), TPGS analogs, TPGS homologs and TPGS derivatives. Alternatively, the surfactants can be other PEG derivatives having similar properties, for example, PEG derivatives of sterols, e.g. a cholesterol or a sitosterol (including, for example, any of the PEG derivatives disclosed in U.S. Pat. No. 6,632,443) or PEG-derivatives of other fat-soluble vitamins, for example, some forms of Vitamin A (e.g. Retinol) or Vitamin D (e.g. Vitamin D1-D5).

In the provided compositions, the surfactants aggregate in aqueous liquid dilution compositions to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. The micelles can contain more than one surfactant.

In general, surfactants also are capable of forming "inverse micelles," which form in lipophilic medium, the hydrophobic tails being in contact with the lipophilic medium and the hydrophilic heads facing the center of the inverse micelle. Typically, however, the surfactants in the provided compositions form micelles in aqueous medium, for example, in aqueous liquids, containing the non-polar ingredient at their center.

Properties of the provided compositions, for example, the particle size of the compositions and desirable properties related to the particle size, are influenced by the choice of surfactant(s) and the relative amount (concentration) of surfactant. For example, the HLB of the surfactant(s) can affect particle size, clarity, taste, smell, crystal formation and other properties of the provided compositions. Similarly, the concentration of the surfactant compared with the concentration(s) of other ingredients, particularly compared with the concentration of water and the concentration of the non-polar compound(s), can affect various desirable properties, for example, the ability to disperse or dissolve in aqueous media, for example, to form a clear aqueous liquid dilution composition or pleasant taste and/or smell.

ii. PEG-Derivatives of Vitamin E

Typically, the surfactant used in the provided compositions and methods is a Vitamin E-derived surfactant (e.g. a tocopherol-derived or a tocotrienol-derived surfactant). Exemplary of suitable Vitamin E-derived surfactants are polyalkylene glycol derivatives, typically polyethylene glycol (PEG) derivatives, of Vitamin E, for example, PEG derivatives of tocopherol. Suitable PEG derivatives of Vitamin E typically contain one or more tocopherols or tocotrienols, joined (for example, by an ester, ether, amide or thioester bond) with one or more PEG moieties, via a linker, for example, a dicarboxylic acid linker. An exemplary surfactant is shown schematically below:

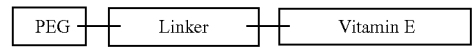

where the line between the PEG and Linker; and the line between the Linker and Vitamin E each independently represent a covalent bond selected from among an ester, ether, amide or thioester.

Typically, the Vitamin E PEG derivatives are made by joining the PEG moiety, via esterification, to a vitamin E-linker conjugate (e.g. a tocopherol-linker conjugate). In one example, the tocopherol-linker conjugate first is formed by covalently joining (by esterification) the hydroxyl moiety of tocopherol with a dicarboxylic acid to produce an ester bond. In this example, the tocopherol-linker conjugate is a tocopherol ester (such as tocopherol succinate). The esterification reaction can be carried out by any of a number of known methods (see, for example, U.S. Pat. Nos. 2,680,749, 4,665,204, 3,538,119 and 6,632,443). To make the tocopherol-PEG surfactant, the resulting tocopherol ester then is joined (via the linker) to the PEG molecule, in another esterification reaction. In this example, the resulting surfactant is a tocopherol polyethylene glycol diester (TPGD).

Alternatively, PEG derivatives of a tocopherol-linker or tocotrienol-linker conjugate can be made by other methods. Various methods known in the art for producing PEG derivatives can be used to join a PEG molecule to tocopherol-linker or tocotrienol-linker compounds. For example, a tocopherol-linker conjugate can be covalently bonded to the PEG molecule via an amide, ether or thioether bond. For example, a tocopherol-linker conjugate that contains an amine group can be reacted with a PEG-NHS derivative to form an amide bond between the tocopherol-linker and the PEG molecule. A tocopherol-linker conjugate that contains an amine group can be reacted with a PEG-aldehyde derivative to form an amide bond between the tocopherol-linker and the PEG molecule. In another example, a tocopherol-linker that contains an carboxylic acid can be activated to the corresponding acid halide and reacted with a PEG-SH derivative to form a thioester bond between the tocopherol-linker and the PEG molecule.

(1) Tocopherols and Tocotrienols

The tocopherol(s) used to make the surfactant can be any natural or synthetic Vitamin E tocopherol, including but not limited to alpha-tocopherols, beta-tocopherols, gamma-tocopherols and delta tocopherols, either in pure forms or in heterogenous mixtures of more than one form. Exemplary tocopherols are d- α tocopherols and d,1-tocopherols. To make the surfactant, the tocopherol typically is esterified with a linker, for example, a dicarboxylic acid, to form a tocopherol ester, which then is joined to a PEG moiety.

The tocotrienol(s) used to make the surfactants can be any natural or synthetic Vitamin E tocotrienol, including but not limited to alpha-tocotrienols, beta-tocotrienols, gamma-trienols and delta tocotrienols, either in pure forms or in heterogenous mixtures of more than one form. Mixtures of tocopherols and tocotrienols, are contemplated for use in the provided methods and compositions. A tocotrienol can be esterified with a linker, such as a dicarboxylic acid, before joining with a PEG moiety.

(2) PEG Moieties

The PEG used in the tocopherol-PEG derivative can be any of a plurality of known PEG moieties. Exemplary of suitable PEG moieties are PEG moieties having varying chain lengths, and varying molecular weights, for example, PEG 1000, PEG 200, PEG 500, and PEG 20,000. The numbers following individual PEG moieties indicate the molecular weight (in daltons (Da)) of the PEG moieties. The PEG moiety of the tocopherol-derived surfactant typically has a molecular weight of between 200 or about 200 to 20,000 or about 20,000 Da, typically between 200 and 6000 Da, for example, between 600 or about 600 Da and 6000 or about 6000 Da, typically between 200 or about 200 Da and 2000 or about 2000 Da, between 600 or about 600 Da and 1500 or about 1500 Da 200, 300, 400, 500, 600, 800, and 1000 Da. Exemplary of a PEG-derivative of tocopherol ester having a PEG moiety with 1000 Da is TPGS-1000. Also exemplary of suitable PEG moieties are PEG moieties that are modified, for example, methylated PEG (m-PEG), which is a PEG chain capped with a methyl group. Other known PEG analogs also can be used. The PEG moieties can be selected from among any reactive PEG, including, but not limited to, PEG-OH, PEG-NHS, PEG-aldehyde, PEG-SH, PEG-NH$_2$, PEG-CO$_2$H, and branched PEGs.

(3) Linkers

Typically, the PEG derivatives of Vitamin E are diesters or other esters, e.g. triesters. When the PEG derivative is a diester, the linker joining the Vitamin E to the PEG typically is a carboxylic acid, typically a dicarboxylic acid, as in, for example, tocopherol polyethylene glycol succinate (TPGS), where the linker is a succinic acid, and the surfactant is made by an esterification reaction joining a PEG moiety and a tocopherol ester of the dicarboxylic acid. In another example, the linker is another molecule, for example, an amino acid, such as glycine, alanine, 5-aminopentanoic acid or 8-aminooctanoic acid; or an amino alcohol, such as ethanolamine.

(4) Tocopherol Polyethylene Glycol and Tocotrienol Polyethylene Glycol Diesters (Dicarboxylic Acid Esters of Vitamin E Linked to PEG)

Typically, the Vitamin E PEG derivatives are vitamin E polyethylene glycol diesters, which are Vitamin E esters of PEG, made by joining a Vitamin E ester to one or more PEG moieties by esterification. Exemplary of the Vitamin E diesters are tocopherol polyethylene glycol diesters (TPGD) and tocotrienol polyethylene glycol diesters.

When the tocopherol or tocotrienol ester linked with the PEG moiety is a tocopherol ester of a dicarboxylic acid (e.g. tocopherol succinate), the linker is a dicarboxylic acid (a carboxylic acid having two carboxy groups, e.g. succinic acid). In this example, the tocopherol or tocotrienol PEG diester is formed by esterification reaction, in which PEG is attached to a tocopherol ester of a dicarboxylic acid.

Exemplary of dicarboxylic acids that can be used as linkers in these tocopherol and tocotrienol PEG diester surfactants are succinic acid, sebacic acid, dodecanodioic acid, suberic acid, or azelaic acid, citraconic acid, methylcitraconic acid, itaconic acid, maleic acid, glutaric acid, glutaconic acid, fumaric acids and phthalic acids. Accordingly, exemplary of the tocopherol esters that can be esterified to form the PEG-derivatives are tocopherol succinate, tocopherol sebacate, tocopherol dodecanodioate, tocopherol suberate, tocopherol azelaate, tocopherol citraconate, tocopherol methylcitraconate, tocopherol itaconate, tocopherol maleate, tocopherol glutarate, tocopherol glutaconate, and tocopherol phthalate, among others.

Exemplary of the vitamin E polyethylene glycol diesters made with dicarboxylic acids are compounds having the following formula shown in scheme I below (and homologs, analogs and derivatives thereof):

Scheme I

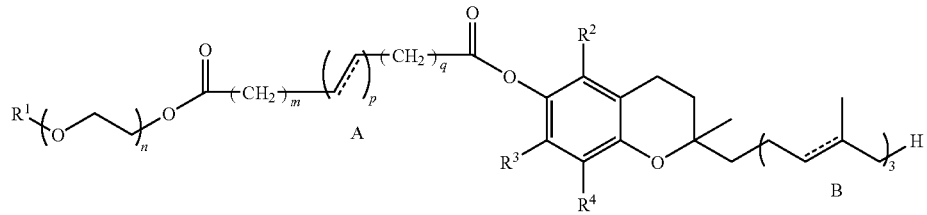

where $R^1$, $R^2$, $R^3$ and $R^4$ each independently is H or Me; each dashed line is independently a single or double bond; n is an integer from 1-5000; m and q each independently are 0 or 1; and p is an integer from 1-20. In one example, the surfactant is a compound where, when both m and q are 0, p is an integer between 2-20.

In one example, the surfactant has the following formula shown in Scheme II below (including homologs, analogs and derivatives thereof):

Scheme II

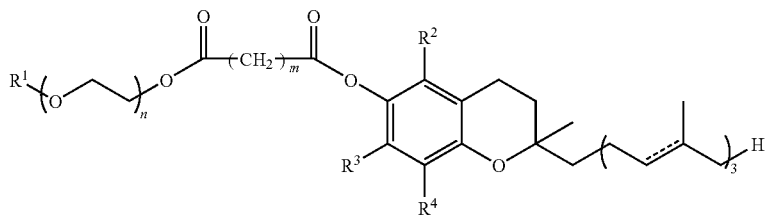

where when $R^1$, $R^2$, $R^3$ and $R^4$ represent a hydrogen or methyl, the bond represented by the dashed line is either a single or double bond, m is any integer between 1 and 20, and n=1-5000.

Exemplary of tocopherol and tocotrienol PEG diesters that can be used as surfactants in the provided compositions and methods include, but are not limited to: tocopherol polyethylene glycol succinates (TPGS; including d-αTPGS and d,1-TPGS; see for example, U.S. Pat. No. 3,102,078), tocophyrol polyethylene glycol sebacate (PTS; see for example, U.S. Pat. No. 6,632,443), tocopherol polyethylene glycol dodecanodioate (PTD; see for example, U.S. Pat. No. 6,632,443), tocopherol polyethylene glycol suberate (PTSr; see for example, U.S. Pat. No. 6,632,443) and tocopherol polyethylene glycol azelaate (PTAz; see for example, U.S. Pat. No. 6,632,443), polyoxyethanyl tocotrienyl sebacate (PTrienS, for example, PTrienS-600; see for example, U.S. Pat. No. 6,632,443), as well as analogs, homologs and derivatives or any of the tocopherol diesters.

(5) Other Vitamin E PEG Esters

In another example, the tocopherol ester joined to the PEG to form the tocopherol PEG diester is a tocopherol ester of a tricarboxylic acid, for example, Citric acid, Isocitric acid, Aconitic acid and Propane-1,2,3-tricarboxylic acid (tricarballylic acid, carballylic acid) or a carboxylic acid having three or more carboxy groups.

In another example, the PEG derivatives of tocopherol are tocopherol polyethylene glycol triesters (TPGT), for example, esters containing a tocopherol, a linker, a PEG moiety, and an additional moiety, for example, an additional tocopherol, a second PEG moiety, or a water-soluble group, such as a quaternary amine. In one example, when the triester contains two PEG moieties, each PEG moiety has a smaller chain length (and lower molecular weight) than the PEG moiety in a PEG derivative of tocopherol, having similar properties, that contains only one PEG chain.

(a) TPGS Surfactants

Exemplary of the tocopherol polyethylene glycol diester surfactants are TPGS, and analogs, homologs and derivatives thereof. TPGS is a natural surfactant that is GRAS and Kosher certified and thus, desirable for use in products designated for human consumptions, for example, beverages, food and nutritional supplements. TPGS typically has an HLB value of between 16 or about 16 and 18 or about 18. Exemplary of the TPGS surfactants is TPGS-1000, which has a PEG moiety of 1000 Da. Exemplary of the TPGS surfactants that can be used in the provided compositions is the food grade TPGS surfactant sold under the name Eastman Vitamin E TPGS®, food grade, by Eastman Chemical Company, Kingsport, TN. This surfactant is a water-soluble form of natural-source vitamin E, which is prepared by esterifyifig the carboxyl group of crystalline d-alpha-tocopheryl acid succinate with polyethylene glycol 1000 (PEG 1000), and contains between 260 and 300 mg/g total tocopherol. A similar compound can be made by esterifying the carboxyl group of the d,1 form of synthetic Vitamin E with PEG 1000. It forms a clear liquid when dissolved 20% in water. This tocopheryl polyethylene glycol is a water-soluble preparation of a fat-soluble vitamin (vitamin E), for example, as disclosed in U.S. Pat. Nos. 3,102,078 and 2,680,749 and U.S. Published Application Nos. 2007/0184117 and 2007/0141203. The PEG moiety of alternative TPGS surfactants can have a molecular weight range of about 200 or 200 to 20,000 or about 20,000 Da, for example, between 600 or about 600 Da and 6000 or about 6000 Da, typically between 600 or about 600 Da and 1500 or about 1500 Da. Also exemplary of the TPGS surfactant that can be used in the provided compositions is the Water Soluble Natural Vitamin E (TPGS), sold by ZMC-USA, The Woodlands, Texas. Any known source of TPGS, or any analog, homolog or derivative thereof, can be used.

Exemplary of TPGS analogs are compounds, other than TPGS, that are similar to a parent TPGS compound, but differ slightly in composition, for example, by the variation, addition or removal of an atom, one or more units (e.g. methylene unit(s)—$(CH_2)_n$) or one or more functional groups.

At room temperature, TPGS typically is a waxy low-melting solid. In one example, the TPGS is heated prior to use, for example, to at least the melting temperature, for example, between 37° C. or about 37° C. and 41° C. or about 41° C. and the desired amount is poured out. In another example, the TPGS can be added as a waxy solid to a vessel and heated with the heating apparatus.

Also exemplary of the surfactants are TPGS analogs, which include Vitamin E derived surfactants, including PEG derivatives of Vitamin E, including vitamin E PEG diesters, such as, but not limited to, tocophyrol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E.

iii. Concentration of the Surfactant

Typically, the concentration of the surfactant(s) in a particular pre-emulsion composition is selected, as described hereinabove, by formulating an initial pre-emulsion composition with a surfactant(s) concentration within a starting concentration range, followed by evaluation of the initial pre-emulsion composition and, optionally, adjusting the surfactant(s) concentration. Alternatively, the surfactant concentration can be chosen based on the concentration of surfactant in one or more existing liquid pre-emulsion composition formula.

In one example, the concentration of the surfactant is greater than 50% or about 50%, typically greater than 60% or about 60%, typically greater than 65% or about 65%, for example, greater than 70% or about 70%, for example, a starting concentration within the concentration range of between 50% or about 50% and 95% or about 95%, between 60% or about 60% and 95% or about 95%, typically between 65% or about 65% and 90% or about 90%, for example, between 69% or about 69% and 90% or about 90%, for example, between 69% or about 69% and 89% or about 89%, for example, 65, 66, 67, 68, 69, 69.5, 69.9, 70, 71, 72, 73, 74, 75, 76, 77, 78, 79, 79.5, 79.9, 80, 81, 82, 83, 84, 85, 86, 87, 88, 89, 89.5, 89.9, or 90%, by weight, of the composition.

In another example, the concentration of the surfactant is greater than 20% or about 20%, typically greater than 30% or about 30%, for example, between 30% or about 30% and 55% or about 55%, for example, between 30% or about 30% and 50% or about 50%, for example, between 30% or about 30% and 45% or about 45%, for example, 30, 31, 32, 33, 34, 35, 36, 37, 38, 39, 40, 41, 42, 43, 44, 45, 46, 47, 48, 49, 50, 51, 52, 53, 54, 55%, by weight, of the composition. This example is typically used for pre-emulsion compositions where the non-polar active ingredient includes a phytosterol.

iv. HLB

Exemplary of the properties of the surfactant(s) that contribute to the desirable properties of the compositions is the HLB hydrophilic-lipophilic balance) of the surfactant(s). Generally, HLB is a value, derived from a semi-empirical formula, which is used to index surfactants according to their relative hydrophobicity/hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W.C. *J. Soc. Cos. Chem.* 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. lipophilic surfactants have greater solubility in oil and lipophilic substances, while hydrophilic surfactants dissolve more easily in aqueous liquids. In general, surfactants with HLB values greater than 10 or greater than about 10 are called "hydrophilic surfactants," while surfactants having HLB values less than 10 or less than about 10 are referred to as "hydrophobic surfactants." HLB values are known for a number of surfactants Table 1 lists HLB values of exemplary surfactants and co-surfactants.

The surfactant(s) used in the provided pre-emulsion composition typically has an HLB value between 14 or about 14 and 20 or about 20, for example, 14, 15, 16, 17, 18, 19, 20, about 14, about 15, about 16, about 17, about 18, about 19 or about 20. Exemplary of suitable surfactants is tocopherol polyethylene glycol succinate (TPGS; also called tocopheryl polyethylene glycol succinate). Other known surfactants having HLB values between 14 or about 14 and 20 or about 20 also can be suitable. Typically, the surfactant is a natural surfactant, for example, a surfactant that is GRAS (generally recognized as safe) by the FDA and/or Kosher certified, for example, TPGS.

(1) TPGS

Exemplary of a surfactant having an HLB between 14 or about 14 and 20 or about 20 is tocopherol polyethylene glycol succinate (TPGS), a natural surfactant that is GRAS and Kosher certified and thus, desirable for use in products designated for human consumption, for example, beverages, food and nutritional supplements. TPGS typically has an HLB value of between 16 or about 16 and 18 or about 18.

Exemplary of the TPGS surfactants that can be used in the provided compositions is the food grade TPGS surfactant sold under the name Eastman Vitamin E TPGS®, food grade, by Eastman Chemical Company, Kingsport, TN. This surfactant is a water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. A similar compound can be made by esterifying the carboxyl group of the d,1 form of synthetic Vitamin E with PEG 1000. It forms a clear liquid when dissolved 20% in water. This tocopheryl polyethylene glycol is a water-soluble preparation of a fat-soluble vitamin (vitamin E), for example, as disclosed in U.S. Pat. Nos. 3,102,078 and 2,680,749 and U.S. Published Application Nos. 2007/0184117 and 2007/0141203. The PEG moiety of alternative TPGS surfactants can have a molecular weight range of about 200 or 200 to 20,000 or about 20,000 Da. Also exemplary of the TPGS surfactant that can be used in the provided compositions is the Water Soluble Natural Vitamin E (TPGS), sold by ZMC-USA, The Woodlands, Texas. Any known source of TPGS can be used.

At room temperature, TPGS typically is a waxy low-melting solid. In one example, the TPGS is heated prior to use, for example, to at least the melting temperature, for example, between 37° C. or about 37° C. and 41° C. or about 41° C. and the desired amount is poured out. In another example, the TPGS can be added as a waxy solid to a vessel and heated with the heating apparatus.

(2) Co-surfactants (Emulsifiers)

In one example, the liquid pre-emulsion composition further contains one or more co-surfactants (emulsifiers). For example, a co-surfactant can be included to improve emulsification of the active ingredient and/or the stability of the composition, for example, by preventing or slowing oxidation of the non-polar compound. Exemplary of a co-surfactant used in the provided pre-emulsion compositions is a phospholipid, for example, phosphatidylcholine.

(a) Phospholipids

Exemplary of the co-surfactants that can be used in the provided compositions are phospholipids. Phospholipids are amphipathic lipid-like molecules, typically containing a hydrophobic portion at one end of the molecule and a hydrophilic portion at the other end of the molecule. A number of phospholipids can be used as ingredients in the provided compositions, for example, lecithin, including phosphatidylcholine (PC), phosphatidylethanolamine (PE), distearoylphosphatidylcholine (DSPC), phosphatidylserine (PS), phosphatidtylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC, Newark, N.J., for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids. Synthetic Phospholipids, PEG-ylated Phospholipids and phospholipid blends sold by Lipoid, LLC. Exemplary of the phosphatidylcholine that can be used as a co-surfactant in the provided compositions is the phosphatidylcholine composition sold by Lipoid, LLC, under the name Lipoid S100, which is derived from soy extract and contains greater than 95% or greater than about 95% phosphatidylcholine.

In one example, the phospholipid, for example, PC, represents less than or equal to 1% or about 1%, by weight (w/w) of the pre-emulsion composition. In one example, the phosphatidylcholine represents between 0.1% or about 0.1% and 1% or about 1%, for example, 0.1, 0.15, 0.2, 0.25, 0.3, 0.35, 0.4, 0.45, 0.5, 0.6, 0.65, 0.66, 0.6690, 0.7, 0.75, 0.8, 0.85, 0.9, 0.95 or 1%, per weight (w/w), of the pre-emulsion composition. In one example, the phospholipid represents between 0.15% or about 0.15% and 0.7% or about 0.7%, by weight (w/w) of the pre-emulsion composition.

v. Preservatives and Sterilizers

In one example, the provided liquid pre-emulsion composition further contains one or more preservatives (or preservativers) and/or sterilizers. The preservative(s) can be included to improve the stability of the pre-emulsion composition, and the compositions made by diluting the pre-emulsion composition, over time. Preservatives, particularly food and beverage preservatives, are well known. Any known preservative can be used in the provided compositions. Exemplary of the preservatives that can be used in the provided compositions are oil soluble preservatives, for example, benzyl alcohol, Benzyl Benzoate, Methyl Paraben, Propyl Paraben, antioxidants, for example, Vitamin E, Vitamin A Palmitate and Beta Carotene. Typically, a preservative is selected that is safe for human consumption, for example, in foods and beverages, for example, a GRAS certified and/or Kosher-certified preservative, for example, benzyl alcohol.

The preservative typically represents less than 1%, less than about 1%, 1% or about 1%, by weight (w/w), of the pre-emulsion composition or between 0.1% or about 0.1% and 1% or about 1%, by weight, of the pre-emulsion composition, for example, 0.1%, 0.2%, 0.3%, 0.4%,0.5%, 0.6%, 0.7%, 0.725%, 0.75%, 0.8%, 0.9%, 1%, about 0.1%, about 0.2%, about 0.3%, about 0.4%, about 0.5%, about 0.6%, about 0.7%, about 0.8%, about 0.9%, about 1%, by weight (w/w), of the liquid pre-emulsion composition.

vi. Emulsion Stabilizers (Co-Emulsifier)

In one example, the provided liquid pre-emulsion compositions further contain one or more emulsion stabilizers (co-emulsifiers), which can be used to stabilize the pre-emulsion composition and/or the aqueous compositions containing the diluted pre-emulsion compositions. In one example, the emulsion stabilizer increases the viscosity of the liquid pre-emulsion composition. In one example, one or more emulsion stabilizers is added, during formulation, after evaluation of an initial pre-emulsion composition, particularly if the oil and water phases of the aqueous liquid dilution composition resulting from dilution of the initial pre-emulsion composition appear to be separating. Addition of the emulsion stabilizer can prevent separation of the oil and water phases, for example, in the liquid dilution compositions.

Exemplary of an emulsion stabilizer that can be used in the provided compositions is a composition containing a blend of gums, for example, gums used as emulsifying agents, for example, a blend containing one or more of xanthan gum, guar gum and sodium alginate, for example, the emulsion stabilizer sold under the brand name SALADIZER®, available from TIC Gums, Inc. (Belcamp, Md.). Other gums can be included in the emulsion stabilizer, for example, gum acacia and sugar beet pectin. Other blends of similar gums can also be used as emulsion stabilizers.

In one example, the emulsion stabilizer is added at a concentration that is less than 1%, for example, between 0.01% or about 0.01% and 1% or about 1% (w/w), emulsion stabilizer, for example, 0.01%, 0.02%, 0.03%, 0.04%, 0.05%, 0.06%, 0.061%, 0.062%,0.063%, 0.0635%, 0.07%, 0.08%, 0.09%, 0.1%, 0.12%, 0.13%, 0.14%, 0.15%,0.16%, 0.17%, 0.18%, 0.19%, 0.2%, 0.25%, 0.3%, 0.31%, 0.32%, 0.33%, 0.34%, 0.35%, 0.36%, 0.37%, 0.38%, 0.39%, 0.4%, 0.5%, 0.6%, 0.7%, 0.8%, 0.9% or 1%, by weight (w/w), of the liquid pre-emulsion composition.

vii. Solvents

In one example, the liquid pre-emulsion compositions further contain a solvent, for example, an oil. Typically, the solvent is included in the composition in addition to the non-polar active ingredient, and is used to dissolve the non-polar active ingredient. In one example, the solvent is an oil that is not contained in the non-polar active ingredient. Typically, the solvent is not the non-polar active ingredient. A number of ingredients can be used either as solvents or as non-polar compounds. When a solvent is included in the pre-emulsion composition, it typically is used to dissolve the non-polar compound before mixing with the other ingredients. In one example, use of a solvent reduces the crystal size and/or increase the clarity of the aqueous liquid dilution composition containing the diluted pre-emulsion composition. Exemplary of solvents that can be used in the provided pre-emulsion compositions are oils (in addition to the non-polar active ingredient), for example, Vitamin E oil, flaxseed oil, CLA, Borage Oil, D-limonene, Canola oil, corn oil, MCT oil and oat oil. Other oils also can be used. Exemplary of the Vitamin E oil, used as a solvent in the provided compositions, is the oil sold by ADM Natural Health and Nutrition, Decatur, Ill, under the name Novatol™ 5-67 Vitamin E (D-alpha-Tocopherol; ADM product code 410217). This Vitamin E oil contains at least 67.2% Tocopherol and approximately 32.8% soybean oil. Also exemplary of a suitable solvent is safflower oil, for example, the high linoleic safflower oil, distributed by Jedwards, International, Inc., Quincy, Mass., which contained between 5% and 10% (e.g. 6.65%) C:16 Palmitic acid, between 1% and 3% (e.g. 2.81%) C:18 Stearic acid, between 12% and 18% (e.g. 14.65%) 18:1 Oleic acid, between 70% and 80% (e.g. 74.08%) C18:2 Linoleic acid and less than 1% (e.g. 0.10%) C18:3 Linolenic acid.

In one example, the concentration of the solvent is within a concentration range of between 1% or about 1% and 55% or about 55%, for example, 1%, 2%, 3%,3.25%,3.5%,3.75%, 4%,5%,5.25%,5.5% or 5.75%,10, 11, 12, 13, 14, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or more, %, by weight, of the pre-emulsion composition.

viii. Flavors

In one example, the pre-emulsion composition further contains one or more flavors or flavoring agents, for example, any compound to add flavor to the pre-emulsion composition and/or to the aqueous liquid dilution composition containing the diluted pre-emulsion composition, for example, the food or beverage containing the pre-emulsion composition. Several flavors are well known. Any flavor can be added to the pre-emulsion compositions, for example, any flavor sold by Mission Flavors, Foothill Ranch, Calif. Exemplary of flavors that can be used are fruit flavors, such as guava, kiwi, peach, mango, papaya, pineapple, banana, strawberry, raspberry, blueberry, orange, grapefruit, tangerine, lemon, lime, lemon-lime, etc.; cola flavors, tea flavors, coffee flavors, chocolate flavors, dairy flavors, root beer and birch beer flavors, methyl slicylate (wintergreen oil, sweet birch oil), citrus oils and other flavors. Typically, the flavors are safe and/or desirable for human consumption, for example, GRAS or Kosher-certified flavors. Exemplary of flavoring agents that can be used in the compositions are lemon oil, for example lemon oil sold by Mission Flavors, Foothill Ranch, Calif.; and D-limonene, for example, 99% GRAS certified D-Limonene, sold by Florida Chemical, Winter Haven, Fla. Typically, the concentration of flavoring agent added to the provided pre-emulsion compositions is less than 5% or about 5%, typically less than 1% or about 1%, for example, 0.1%, 0.2%, 0.3%, 0.4%, 0.5%, 0.6%, 0.7%, 0.8%, 0.9%, 0.37% or 0.525%, by weight (w/w), of the pre-emulsion composition.

ix. pH Adjusters

In one example, one or more pH adjusters is added to the provided pre-emulsion compositions. Alternatively, the pH adjuster can be added, at an appropriate concentration to achieve a desired pH. Typically, the pH adjuster is added to adjust the pH of the pre-emulsion composition to within a range of 2.0 or about 2.0 to 4.0 or about 4.0. One or more of a plurality of pH adjusting agents can be used. Typically, the pH adjusting agent is safe for human consumption, for example, GRAS certified. Exemplary of the pH adjuster is citric acid, for example, the citric acid sold by Mitsubishi Chemical, Dublin, Ohio.

Typically, the concentration of pH adjuster added to the provided pre-emulsion compositions is less than 5% or about 5%, typically less than 1% or about 1%, for example, 0.1%, 0.2%, 0.3%, 0.4%, 0.5%, 0.6%, 0.7%, 0.8%, 0.9%, 0.28% or 0.19%, by weight (w/w), of the pre-emulsion composition.

2. Powder

The compositions also can be provided in powder form, i.e. powder that is made by converting the provided pre-emulsion composition into a powder, using one of several well-known methods (e.g. spray-drying and/or milling). The powder compositions include, but are not limited to, coated or uncoated swallowable or chewable tablets, dry powders in hard or soft gelatin capsules, and dry powders in individual or multiple use packages for reconstituted suspensions or sprinkles. Preferable solid dosage forms are coated or uncoated swallowable or chewable tablets. Suitable methods for manufacturing the powder compositions are well known in the art.

Additionally, the powder composition can further contain at least one excipient. For example, the powder can be formed by spray-drying a pre-emulsion composition that has been mixed with one or more excipients. Excipients include, but are not limited to, diluents (sometimes referred to as fillers) including, for example, microcrystalline cellulose, mannitol, lactose, calcium phosphate, dextrates, maltodextrin, starch, sucrose, and pregelatinized starch; disintegrants including, for example, crospovidone, sodium starch glycolate, croscarmellose sodium, starch, pregelatinized starch, and carboxymethylcellulose sodium; binders including, for example, starch, hydroxypropyl cellulose, hydroxypropylmethyl cellulose, pregelatinized starch, guar gum, alginic acid, gum acacia, carboxymethylcellulose sodium, and polyvinyl pyrrolidone; glidants including, for example, colloidal silicon dioxide and talc; and lubricants/antiadherents including, for example, magnesium stearate, calcium stearate, stearic acid, sodium stearyl fumarate, glyceryl monostearate, hydrogenated vegetable oil, and talc. In one particular example, the excipients are selected from any one or more of maltodextrin and gum acacia. In one example, the excipient contains a 35:65 ratio of maltodextrin:gum acacia. In another example, the excipient is maltodextrin.

Typically, the concentration of the excipients is within a concentration range of between 50% or about 50% and 85% or about 85%, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or more, %, by weight, of the free flowing powder.

The powder forms can be used for any convenient dosage amount the non-polar compound. Generally, the level of non-polar compound can be increased or decreased according to the judgment of the physician, pharmacist, pharmaceutical scientist, or other person of skill in the art. The amount of the remaining non-active ingredients can be adjusted as needed.

In one example, the powder form is a free-flowing powder. Free-flowing powders can be obtained using techniques well known in the art, such as, but not limited to, spray drying, freeze drying or absorption plating. In one example, in order to achieve a free flowing powder, the protein derivative is formulated with an excipient such as lactose or starch. For example, the formulation can be a spray-dried lactose formulation (see e.g., U.S. Pat. No. 4,916,163).

The methods for forming the powders include spray drying. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50. Chem. Eng. Prog. Monogr. Series 2 (1954), and Masters, Spray Drying Handbook (Fourth Edition 1985). Methods for spray drying are well known (see, e.g. U.S. Pat. Nos. 5,430, 021; 6,534,085 and U.S. application publication number US2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Provided are methods for spray drying the pre-emulsion compositions to form powder compositions. In the spray drying methods, the pre-emulsion compositions are heated, e.g. to a temperature between at or about 100 and at or about 150° F., typically between 110° F. and 140° F., e.g. at or about 110, 115, 120, 125, 130, 135 or 140° F. The compositions can be mixed while heating, such as with any of the mixers described herein, for example, homogenizers (e.g. reversible homogenizers and piston-driven homogenization homogenizers).

For spray-drying, one or more excipients are mixed with a polar solvent, typically water, and heated, e.g. to a temperature between at or about 100° F. and at or about 150° F., typically between 110° F. and 140° F., e.g. at or about 110, 115, 120, 125, 130, 135 or 140° F. In one example, the excipient is mixed with water in an amount of one part excipient (by weight) to two parts water (by weight). The excipient-solvent (e.g. water) mixture can be mixed while heating, e.g. using any of the mixers described herein, for example, homogenizers (e.g. reversible homogenizers and piston-driven homogenizers) with heating during the mixing. The heated pre-emulsion composition and the heated water-excipient mixture then are mixed together, such as by transferring one mixture to the other, e.g. by any of the transfer means provided herein. Typically, the two mixtures are homogenized, e.g. with a reversible homogenizer or piston-driven homogenizer or any other homogenizer. The homogenized mixture then is subject to spray drying using a spray dryer.

Exemplary of the spray dryers are cyclone spray dryers. During spray drying with cyclone spray dryers, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

As will be appreciated by one of skill in the art, the inlet temperature and the outlet temperature of the spray drier are not critical but will be of such a level to provide the desired particle size, of less than at or about 1 micron, and to result in a powder that has a desired property. Typically, the ability of the free flowing powder to yield a clear (or relatively clear) liquid dilution composition upon dilution in an aqueous medium is the desired property that is evaluated. In this regard, the inlet and outlet temperatures are adjust depending on the melting characteristics of the pre-emulsion concentrate components and the composition of the homogenized pre-emulsion concentrate/excipient mixture. The inlet temperature is between at or about 60° C. and at or about 170° C. with outlet temperatures between at or about 40° C. to at or about 120° C. Preferably inlet temperatures are from at or about 90° C. to at or about 120° C. and outlet temperatures are from at or about 60° C. to at or about 90° C. The flow rate which is used in the spray drying equipment will generally be at or about 3 mL per minute to at or about 15 mL per minute. The atomizer air flow rate will very between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, the dry powder is stored into a capsule form or is pressed into a tablet. For use as tablets, the compositions typically contain multiple other excipients. These excipients include tablet disintegrants, such as corn starch, glidants, such as silicon dioxide, and lubricants such as magnesium stearate. Ordinarily these compositions contain minor amounts by weight of glidants and lubricants, e.g., each two percent (2%) or less by weight. Tablet disintegrants are optionally present, and, if present, are included in sufficient amounts to assure that the tablet disintegrates upon ingestion. According materials, such as corn starch, are employed at concentrations of from about zero to about 30 percent by weight of the composition.

Free flowing powders also can be used to administer the active agent by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch. For example, such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519); Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

3. Liquid Dilution Compositions Containing the Diluted Pre-emulsion Compositions Also among the compositions provided herein are liquid dilution compositions, typically aqueous liquid dilution compositions, containing the non-polar compounds. The aqueous liquid dilution compositions are made by diluting the provided pre-emulsion compositions into aqueous media, for example, beverages, for example, water, flavored water, soda, milk, coffee, tea, juices, including fruit juices, sauces, syrups, soups, sports drinks, nutritional beverages, energy drinks, vitamin-fortified beverages, or any beverage.

In one example, the aqueous liquid dilution compositions contains between 0.05 grams (g) or about 0.05 g and 10 g or about 10 g, typically between 0.05 g and 5 g, of the liquid pre-emulsion composition per 8 fluid ounces or about 8 fluid ounces, at least 8 fluid ounces or at least about 8 fluid ounces, or less than 8 fluid ounces or less than about 8 fluid ounces, or per serving size, of the aqueous medium, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the pre-emulsion composition per 8 fluid ounces, about 8 fluid ounces, or at least 8 fluid ounces or at least about 8 fluid ounces of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains between 1 mL or about 1 mL and 10 mL or about 10 mL of the liquid pre-emulsion composition, for example, 1 mL, 2 mL, 3 mL, 4 mL, 5 mL, 6 mL, 7 mL, 8 mL, 9 mL or 10 mL of the pre-emulsion composition, per 8 fluid ounces, about 8 fluid ounces, at least 8 fluid ounces or at least about 8 fluid ounces, or less than 8 fluid ounces or less than about 8 fluid ounces, or per serving size, of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains at least 10 mg or about 10 mg, typically at least 25 mg or about 25 mg, typically at least 35 mg, of the nonpolar compound, for example, the non-polar active ingredient, per 8 fluid ounces or about 8 fluid ounces, at least 8 fluid ounces or at least about 8 fluid ounces of the aqueous medium, or less than 8 ounces or less than about 8 ounces, or per serving size, of the aqueous medium; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar compound per at least 8 fluid ounces or at least about 8 fluid ounces of aqueous medium.

In another example, the aqueous liquid dilution composition contains the pre-emulsion composition diluted at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In another example, the aqueous liquid dilution compositions contain the liquid pre-emulsion composition diluted to any amount. In another example the dilution is less than 1:10 or about 1:10.

Properties of the provided liquid pre-emulsion compositions that are diluted into the aqueous medium contribute to various properties of the provided resulting aqueous liquid dilution compositions, for example, clarity; desirability for human consumption, for example, pleasant taste, and/or smell, for example, lack of "fishy" taste/smell, lack of "ringing" and lack of crystal formation; stability, for example, lack of oxidation, "ringing" and/or precipitation over time; and safety for human consumption. As described above, the liquid pre-emulsion compositions are formulated according to the desired properties of the aqueous liquid dilution compositions containing the pre-emulsion compositions.

a. Clarity

In one example, the aqueous liquid dilution compositions are clear aqueous liquid dilution compositions or non-turbid aqueous liquid dilution compositions, for example, as determined, as described below, empirically or by measuring turbidity and/or particle size. In another example, the aqueous liquid dilution compositions are not clear, or not completely clear. The liquids can be more or less clear, or have the same clarity as another liquid, for example, an aqueous liquid dilution composition made according to the provided methods or a beverage, for example, a beverage that does not contain the diluted pre-emulsion composition. Properties of the liquid pre-emulsion compositions can affect the clarity of the liquid. A number of parameters can vary the clarity of the liquids, for example, the relative concentration of surfactant, non-polar compound and/or water; the type of non-polar ingredient; the concentration of excipient(s) in the particular non-polar compound; and the purity of the non-polar compound, for example, whether it has been standardized to a high purity, or whether it is an extract or a filtered extract. For example, an aqueous liquid dilution composition made by diluting a pre-emulsion composition containing a non-polar active ingredient that contains lecithin, for example a high amount of lecithin, can be less clear than one made with a pre-emulsion composition containing a non-polar compound that does not contain lecithin. In another example, a liquid pre-emulsion composition containing a non-polar compound that is a filtered extract can produce a clearer aqueous liquid dilution composition when diluted than a pre-emulsion composition containing a crude extract.

i. Clarity Determined by Empirical Evaluation

In one example, the clarity/turbidity of the aqueous liquid dilution composition containing the diluted pre-emulsion composition is evaluated qualitatively, by observation. In one example, a liquid can be considered clear if it does not have a cloudy appearance and/or if no or few particles are visible when viewing the liquid with the naked eye or if it is the same or substantially similar in clarity to another liquid, for example, a beverage, for example, water, fruit juice, soda or milk. In some cases, the aqueous liquid dilution composition is as clear or about as clear as water or another liquid, for example a beverage. For example, the liquid (containing the liquid pre-emulsion composition diluted in an aqueous medium, for example, a beverage) can be as clear or about as clear as the aqueous medium not containing the liquid pre-emulsion composition. In a related example, there is no substantial difference, for example, no observable difference, between the aqueous liquid dilution composition containing the pre-emulsion composition and the aqueous medium without the pre-emulsion composition. A clear liquid is not necessarily colorless, for example, a yellow liquid that contains no visible particles or cloudiness can be considered clear. In another example, the liquid is clear or partially clear or substantially clear if no crystals are visible and/or if no "ringing" is observed on the container containing the liquid.

ii. Clarity Determined by Particle Size or Number of Particles

In another example, clarity of the aqueous liquid dilution composition is evaluated by measuring the particle size and/or number of particles of the liquid.

In one example, the aqueous liquid dilution compositions have a particle size less than 200 nm or less than about 200 nm, for example, 5, 10, 15, 20, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. In another example, the aqueous liquid dilution composition has a particle size less than 100 nm or about 100 nm, less than 50 nm or about 50 nm or less than 25 or about 25 nm. Typically, the particle size of the aqueous liquid dilution composition is between 5 nm or about 5 nm and 200 nm or about 200 nm, or between 5 nm or about 5 nm and 50 nm or about 50 nm.

Typically, the particle size of the provided aqueous liquid dilution composition containing the liquid pre-emulsion composition, which contains the non-polar compound, is smaller than the particle size of a liquid containing the non-polar compound (not formulated in a liquid pre-emulsion composition).

iii. Turbidity

In another example, the clarity of the liquid is evaluated and/or expressed using a turbidity measurement, for example, Nephelometric Turbidity Units (NTU), as measured using the provided methods, described below. In this example, turbidity is measured optically, to get value indicating the cloudiness or haziness of the liquid, which correlates with particles in suspension in the liquid. The more clear a liquid is, the lower its turbidity value.

In one example, the clear aqueous liquid dilution composition has a turbidity value (NTU) of 30 or about 30; or an NTU value of less than 30 or about 30, for example, less than 29 or about 29, less than 28 or about 28, less than 27 or about 27, less than 26 or about 26, less than 25 or about 25, less than 24 or about 24, less than 23 or about 23, less than 22 or about 22, less than 21 or about 21, less than 20 or about 20, less than 19 or about 19, less than 18 or about 18, less than 17 or about 17, less than 16 or about 16, less than 15 or about 15, less than 14 or about 14, less than 13 or about 13, less than 12 or about 12, less than 11 or about 11, less than 10 or about 10, less than 9 or about 9, less than 8 or about 8, less than 7 or about 7, less than 6 or about 6, less than 5 or about 5, less than 4 or about 4, less than 3 or about 3, less than 2 or about 2, less than 1 or about 1; or 29 or about 29, 28 or about 28, 27 or about 27, 26 or about 26, 25 or about 25, 24 or about 24, 23 or about 23, 22 or about 22, 21 or about 21, 20 or about 20, 19 or about 19, 18 or about 18, 17 or about 17, 16 or about 16, 15 or about 15, 14 or about 14, 13 or about 13, 12 or about 12, 11 or about 11, 10 or about 10, 9 or about 9, 8 or about 8, 7 or about 7, 6 or about 6, 5 or about 5, 4 or about 4, 3 or about 3, 2 or about 2, 1 or about 1, or 0 or about 0.

In another example, the turbidity value of the aqueous liquid dilution composition is less than 200 or less than about 200, for example, 200, 175, 150, 100, 50, 25 or less.

In another example, it is desirable that the aqueous liquid dilution composition contains a turbidity value that is comparable, for example, about the same as, the same as, or less than or greater than, the turbidity value of another liquid, for example, a beverage not containing the liquid pre-emulsion composition or an aqueous liquid dilution composition made by the provided methods.

b. Stability

Typically, the provided aqueous liquid dilution compositions containing the pre-emulsion compositions are stable, for example, free from one or more changes over a period of time, for example, 1, 2, 3, 4, 5, 6, 7, 8, 9, 10, 11 or 12 months, 1, 2, 3, 4 or more years.

In one example, the compositions are stable because they are free from oxidation or substantial oxidation over time. In another example, they are stable because they remain clear over time. In another example, the stable compositions remain safe and/or desirable for human consumption over time. In one example, stability refers to the lack of precipitates forming in the compositions over the period of time. In a related example, the compositions are stable because they do not exhibit "ringing," formation of a whitish or opaque ring around the perimeter of the container holding the liquid, typically at the surface of the liquid. Ringing typically is undesirable, particularly in the case of a liquid for human consumption, for example, a beverage.

In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature. In one example, the compositions remain stable at room temperature, for example, 25° C. or about 25° C. In another example, the compositions remain stable at between 19° C. and 25° C. In another example, the compositions remain stable at refrigerated temperatures, for example, 4° C. or about 4° C., or at frozen temperature, for example, at −20° C. or about −20° C.

Stability refers to a desirable property of the provided compositions, for example, the ability of the provided compositions to remain free from one or more changes over a period of time, for example, at least or over 1, 2, 3, 4, 5, 6 or more days, at least or over 1, 2, 3, 4, or more weeks, at least or over 1, 2, 3, 4, 5, 6, 7, 8, 9, 10, 11, 12 or more months, or at least or over 1, 2, 3, 4 or more years. In one example, the composition is stable if it is formulated such that it remains free from oxidation or substantial oxidation over time. In another example, the stable compositions remain clear over time. In another example, the stable compositions remain safe and/or desirable for human consumption over time. In one example, stability refers to the lack of precipitates forming in the compositions over the period of time. In a related example, stability refers to the lack of "ringing" over the period of time. In another example, the composition is stable if it does not exhibit any visible phase separation over a period of time, for example, after 24 hours, after one week or after one month. In one example, the compositions are stable if they exhibit one or more of these described characteristics, over time, when kept at a particular temperature.

In one example, the compositions are stable when stored at room temperature, for example, 25° C. or about 25° C. In another example, the compositions remain stable when stored at between 19° C. and 25° C. In another example, the compositions remain stable when stored at refrigerated temperatures, for example, 4° C. or about 4° C., or at frozen temperature, for example, at −20° C. or about −20° C.

c. Desirable Characteristics for Human Consumption

In one example, the liquid dilution composition is desirable for human consumption, for example, for use in a food or beverage. Different properties of the liquid dilution composition can contribute to its desirability as a consumable product. For example, taste, smell, clarity, color, crystal formation, precipitation and "ringing," all can relate to desirability.

In one example, the liquid dilution composition has a pleasant taste and/or smell, for example, due to one or more flavors added to the pre-emulsion composition and/or to the aqueous medium. In another example, the liquid dilution composition containing the pre-emulsion composition is free from an unpleasant taste or smell, for example, a "fishy" taste or smell. In one example, the pre-emulsion composition smells or tastes less unpleasant, for example, less fishy, compared to another aqueous liquid dilution composition.

In another example, the aqueous liquid dilution composition is desirable because it does not have crystals or has fewer crystals compared with another aqueous liquid dilution composition. In another example, the aqueous liquid dilution composition is desirable because it does not exhibit ringing.

d. Safety

Typically, the aqueous liquid dilution compositions containing the pre-emulsion compositions are safe for human consumption, for example, containing only ingredients approved by the FDA for human consumption, for example GRAS-certified ingredients. In one example, one or more of the ingredients, for example, all the ingredients, are Kosher-certified. Safety of the compositions also relates to stability over time. Lack of or minimum oxidation of the compositions over time can contribute to the safety of the compositions.

e. Oral Bioavailability

In one example, the non-polar compounds, for example, the non-polar active ingredients, contained in the aqueous liquid dilution compositions exhibit a high or relatively high bioavailability, for example, a bioavailability that is higher than a liquid containing the non-polar active ingredient alone (i.e. not formulated in the liquid pre-emulsion composition). Bioavailability relates to the ability of the body to absorb the non-polar active ingredient into a particular space, tissue cell and/or cellular compartment. Typically, non-polar active ingredients in liquids having small particle sizes are better absorbed than those with larger particle sizes.

C. Methods for Making Pre-emulsion Compositions Containing Non-polar Compounds Also provided are methods for making the pre-emulsion compositions. General equipment and steps of the methods are detailed below. In one example, the general methods for making the pre-emulsion compositions are carried out using a bench-top manufacturing process, which is used for making relatively smaller-sized batches of the pre-emulsion compositions. In another example, the general methods for making the pre-emulsion compositions are carried out using a scaled-up manufacturing processes, which is used for making relatively larger batches of the pre-emulsion compositions. The bench-top process can be scaled up to the scaled-up process. Any pre-emulsion composition made using the bench-top method can be made using the scaled-up process, by scaling up the method.

1. Equipment for Making the Pre-emulsion Compositions

Various equipment, for example, vessels for mixing, heating, holding and/or packaging the ingredients, for example, tanks and beakers; scales; mixers, including standard mixers and homogenizers; heating and cooling apparatuses, including water-jacketed tanks, hot plates, water baths and chillers (coolers), including recirculating coolers, water baths and ice baths; transfer apparatuses, for example, transfer means, for example, pumps, hoses, sanitary fittings; ball valves; purifiers, for example, filters, for example, carbon filters, ion exchange equipment, reverse osmosis equipment, end-point filters and end product filters; evaluation means, for example, pH and temperature meters; and other equipment, is used in various steps of the provided methods for making the pre-emulsion compositions. The choice of equipment depends on a plurality of factors, including batch size and manufacturing process.

a. Scales

One or more scales typically is used to measure the ingredients before adding them to the appropriate vessel. Alternatively, the ingredients can be weighed in the vessel, for example in a tank mounted on top of a scale.

Any of a plurality of well-known, commercially sold scales can be used to weigh the ingredients. Choice of scale(s) can depend on a number of factors, including the mass of the final pre-emulsion composition being made and the ingredient being weighed. In one example, multiple scales are used to weigh the various ingredients of the pre-emulsion composition. In general, relatively larger capacity (weight) scale(s) are used in making larger batches of pre-emulsion composition while relatively smaller capacity scale(s) are used in making smaller batches.

Exemplary of the scales used with the provided methods to weigh the ingredients are a Toledo Scale (Model GD13x/USA), a Sartorius Basic Analytical Scale (Model BA110S) which is a basic series analytical scale with a 110 g capacity and a resolution of 0.1 mg; and an OHAUS Scale (Model CS2000), which is a compact portable digital scale having a 2000 g capacity and a resolution of 1 g.

b. Purifiers, Including Filters

Purifiers, typically more than one purifier, for example, filters, are used in the provided methods to remove impurities in the ingredients prior to their addition to the pre-emulsion composition and/or from the final pre-emulsion composition and/or an intermediate phase of the pre-emulsion composition. In one example, one or more purifiers, for example, carbon filters, ion exchange purifiers, reverse osmosis purifiers, and/or end point filters are used to filter water, for example, city water, prior to its addition to compositions provided herein, for example, to the dilution compositions, for example, to remove impurities, for example, sediment, from the water.

Exemplary of the purifiers that can be used with the provided methods are filters, for example, 100 micron filters and carbon filters, which are filters that use activated carbon to remove impurities by chemical adsorption. Carbon filtering typically is used for water purification and are particularly effective at filtering out chlorine, sediment, volatile organic compounds and other impurities. Typically, the particles removed by carbon filters are between about 0.5 microns and about 50 microns. Other filters are well known and can be used with the provided methods.

Also exemplary of the purifiers that can be used in the provided methods are reverse osmosis purifiers, which use mechanical pressure to purify liquids, for example, water. In one example, the pressure forces the water through a semi-permeable membrane to remove impurities.

Also exemplary of the purifiers that can be used in the provided methods are ion exchange purifiers, for example, an ion exchange purifier using a resin bed, for example, a zeolite resin bed, to replace salts, e.g. cations, for example, magnesium and calcium, with other cations, for example, sodium and potassium cations. Such purifiers can be purchased, for example, from Aquapure Filters, Clarkston, Mich.

In another example, an end product filter (e.g. a 100 micron FSI filter, Product Number BPEM 100-5GP). This filter is used to filter any impurities out of the final product (e.g. the final pre-emulsion composition). Other filters are known and can be used with the provided methods.

c. Vessels for Mixing the Ingredients

One or more, typically two or more, vessels, for example, tanks, for example, water-jacketed tanks; flasks; cylinders; pots; and/or beakers, for example, Pyrex® beakers, are used in the provided methods to contain the ingredient(s) of the liquid pre-emulsion compositions, for example, during mixing and/or heating or cooling. Typically, vessels are used for mixing and heating the ingredients of the composition. In another example, an additional vessel, for example, a holding and/or packaging tank, is used for holding and/or packaging the pre-emulsion composition.

A number of vessels are available for mixing ingredients. Typically, the vessels are cleaned, for example, rinsed, soaped and/or sanitized according to known procedures, prior to use and between uses.

In one example, typically used with the bench-top process, the vessel is a container, for example, a bench-top container, for example, flasks, beakers, for example, Pyrex® beakers, vials, measuring containers, bottles and/or other bench-top containers.

In another example, typically used with the scaled-up manufacturing process, the vessels are tanks, for example, mixing tanks and holding/packaging tanks. Typically, the tanks are equipped with one or more mixers, for example, a standard mixer and/or homogenizer, which are used to mix the ingredients added to the tank. In one example, the tank further is equipped with a heating and/or cooling device. For example, the tank can be a water-jacketed tank. The temperature of the water-jacketed tank is controlled through the water-jacket, for example, to heat the contents, for example, while mixing.

Exemplary of the tanks that can be used with the provided methods are water-jacketed tanks, for example, the Overly 550 Gallon water jacketed tank (Model 10576501G), which has a 550 gallon capacity, the Schweitzers 450 gallon tank (Model # 5214-C; e.g. sold by Machinery and Equipment, Pomona Calif.), which has a 450 gallon capacity and the Royal 190 gallon water jacketed tank (Model 9977-5), which has a 190 gallon capacity and when mixing smaller volumes. Other tanks are well known and can be used with the provided methods for mixing the pre-emulsion compositions, for example, the phases of the pre-emulsion compositions.

d. Mixers

Mixers are used in the provided methods to blend, mix and/or homogenize the liquid pre-emulsion compositions and/or various ingredients of the liquid pre-emulsion compositions. In one example, the mixers are used to keep the ingredients and/or mixture circulating to maintain temperature, viscosity and/or other parameters of the mixture. Exemplary of the mixers that can be used in the provided methods are standard mixers, for example, standard mixers, which can be used, for example, to mix the ingredients, to maintain a homogeneous mixture while heating. Exemplary of the standard mixers is a LIGHTNIN® mixer (LIGHTNIN, Rochester, N.Y.), for example, Model Numbers XJC117 and ND-2. In one example, the LIGHTNIN® mixers are fixed-mount, gear drive high-flow mixers, for use with closed tanks. Another example of a standard mixer is a mixer sold by IKA®, for example, overhead IKA® mixers, for example, model Nos. RW-14 Basic and RE-16S, which are laboratory stirrers and can be used to mix ingredients. In one example, the mixer(s) are attached to the vessels, for example, the tanks, for example, mounted or clamped onto the tanks, for example, the top of the tanks. In another example, the mixers are placed in the vessels for mixing.

Also exemplary of the mixers used with the provided methods are homogenizers (also called shears), which typically are used to homogenize the ingredients after they are combined. The homogenizers typically provide high shear dispersion of solids and emulsification of immiscible liquids at high shear rates. Exemplary of the homogenizers that can be used in the provided methods are high-shear homogenizers, for example, reverse homogenizers sold by Arde Barinco, Inc., Norwood, NJ, for example, Model CJ-50, which is a 3600 rpm mixer having a 6 inch rotor diameter, a tip speed of 5575 ft/minute and an emersion depth of 33 inches; and Model CJ-4E, which is a 10,000 rpm mixer with fan-cooled motor, optimized for 1 to 5 gallon batch sizes, having a 1.875 inch rotor diameter, a tip speed of 4920 rpm and an immersion depth of 16 inches. The homogenizer typically has six separate openings at the bottom and top, which concentrates the liquid into six chambers, reducing the surface volume and creating a shear effect. Other homogenizers, for example, other reversible homogenizers sold by Arde Barinco Inc., can be used with the provided methods.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from top and bottom of the mixture, while upward "umbrella flow" controls mixing at the highest shear and recirculation rates without splashing or incorporation of air. The reversible homogenizers typically are equipped with an adjustable baffle plate, which can be adjusted to control the type of mixing, for example at different times during homogenization.

A number of additional mixers are well known and can be used with the provided methods. Exemplary of the mixers that can be used with the provided methods are shears, inline mixers/mixing, Ribbon, Plow/Paddle Blenders Forberg Mixers, Conveyors, Bag Dumps & Compactors, V-Blenders, Blade Mixers, Double Cone Mixers, Continuous Mixers, Speedflow Mixers, Batch Mixers, Double Ribbon Blenders, Paddle and Ribbon Mixers with Choppers, Plow Blenders/Turbulent Mixers, Fluidizing Forberg-Type Mixers, Air Mixers, Active Mixers, Passive Mixers, Top Entry Mixers, Side Entry Mixers, Static Mixers, Fixed Entry Mixers, Portable Mixers—both direct and gear drive, Sanitary Mixers, Drum Mixers, Bulk Container (IBC) Mixers, Lab Stirrers, Variable Speed Mixers, dough mixer, vertical mixer, spiral mixer, twin arm mixer, fork mixer, double spiral mixer, all agitators, agitator mixers, Banbury Mixers, Rubber Mixers, Blondheim Mixers, Chum Mixers, Conical Mixers, Continuous Mixers, Disperser Mixers, Pan Mixers, Emulsifier Mixers, Hobart Mixers, Liquifier Mixers, Littleford Mixers, Meat Mixers, Plow Mixers, Mixmuller Mixers, Nauta Mixers, Oakes Mixers, Planetary Mixers, Pony Mixers, PUG Mixers, Ribbon Mixers, Ross Mixers, Rotary Mixers, Sigma Mixers, Single Arm Mixers, Tote Bin Mixers, Tumble Mixers, Vacuum Mixers, Turbolizer Mixers, Twin Shell Mixers, V-Type Mixers, Zig-Zag Mixers side arm mixers, hand-held mixers, stir rods, stir bars, magnetic mixers and overhead mixers, for example, mechanical and/or electric overhead mixers.

e. Heating Apparatuses

One or more, typically more than one, heating apparatuses are used in the provided methods to control the temperature of the ingredients, phases and/or pre-emulsion composition, typically while mixing.

In one example, the heating apparatuses are water-jackets. In this example, the vessels used to mix the ingredients are water jacketed tanks. The water jacket can be controlled, for example, using a control panel, to adjust the temperature of the contents of the vessel.

Alternatively, other heating apparatuses can be used to heat the ingredients, and/or pre-emulsion compositions. Exemplary of heating apparatuses that can be used with the provided methods are immersible and/or submersible heaters, for example, 12 KW or 13 KW sanitary heaters, which are food-grade heaters that are immersed into the tanks while mixing, typically for applications requiring high heat, for example, temperatures greater than about 60° C. or 60° C., or greater than 80° C. or about 80° C. Also exemplary of heating apparatuses are stoves, for example, propane stoves. Also exemplary of the heating apparatuses are hot plates, for example, the Thermolyne hot plate, model number 846925 or model number SP46615. Typically, the heater is capable of heating the mixture to between 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C. Typically, the heater is capable of heating the mixture to 60° C. or 60° C., for example, providing low heat.

f. Cooling Apparatuses

One or more cooling apparatuses can be used with the provided methods, for example, to cool the ingredients during mixing, for example, to chill the mixture while homogenizing. Exemplary of the cooling apparatuses are chillers, for example, recirculating coolers, which can be attached to the vessel, for example, remotely or by a tank mounted in the cooler, to recirculate fluid from the tank, through the chiller and back to the tank, in order to rapidly cool and maintain the temperature of the mixture during mixing. Exemplary of an open-loop chiller that can be attached to the tank and used with the provided methods are chillers sold by Turmoil, West Swanzey, N.H., for example, open or closed-loop coolers, for example, model No. OC-1000 RO. Other cooling apparatuses are well known and can be used with the provided methods.

Also exemplary of the cooling apparatuses are water baths and ice baths, for example, water baths and/or ice baths in which the vessel(s) are placed, for example, during homogenizing.

Typically, the cooling apparatus can be used to cool the liquid to between 25° C. or about 25° C. and 45° C. or about 45° C., for example, 25, 26, 27, 28, 29, 30, 31, 32, 33, 34, 35, 36, 37, 38, 39, 40, 41, 42, 43, 44 or 45° C., typically between 25° C. and 43° C., typically between 35° C. and 43° C., for example, 26.5° C. Typically, the cooling is rapid cooling, for example, cooling to between 25° C. or about 25° C. and 45° C. or about 45° C., for example, between 35° C. and 43° C., for example, 26.5° C., in between 15 minutes or about 15 minutes and 2 hours or about 2 hours, typically, between 30 minutes or about 30 minutes and 60 minutes or about 60 minutes, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

g. Transfer Means

Transfer means are used with the provided methods to transfer liquid from one vessel to another vessel, for example, to transfer the contents of one or more vessels to one or more other vessels, for example, to transfer the pre-emulsion composition to a holding vessel (e.g. a holding tank). Exemplary of the equipment used for the transfer means are transfer pumps and associated accessories, for example, ball valves, sanitary fittings (for example, sanitary fittings sold by Granger, Inc., Lake Forrest Il) and transfer hoses (for example, hoses sold by Sani-Tech West, Oxnard, Calif.), for example, food grade hoses attached to the transfer pumps. Exemplary of the transfer pumps that can be used with the provided methods is the Teel Pump (Model 2P377B), Granger, Inc. Lake Forrest Ii, a self-priming pump having a power rating of 2 HP, 60 Hz voltage 208-230/460 AC, speed of 3450 rpm. Other pumps, for example, other self-priming pumps from Grainger, Inc., can be used as part of the transfer means in the provided methods. Alternatively, transfer means can include means for manually transferring the liquid to another vessel, for example, by pouring, pipetting and/or other well-known methods of manually transferring liquids.

h. Evaluation Equipment

Evaluation equipment is used to evaluate one or more properties of the compositions, for example, the phases of the compositions and/or the final pre-emulsion compositions. For example, evaluation equipment can be used to measure one or more parameters of the pre-emulsion compositions and/or the phases, for example, the temperature and the pH of the liquids. Exemplary of the evaluation equipment are pH meters and temperature meters. Exemplary of the pH/temperature meters is the pH and temperature meter sold by Hanna Instruments, (model number HI 8314), which can be used to measure both the temperature and the pH of the mixture(s). Also exemplary of temperature meters are temperature probes, for example, digital and/or water-proof temperature probes, for example, temperature probes sold by Cooper-Atkins, Middlefield, Conn., for example, the digital waterproof temperature probe (Model # DPP400W) from Cooper-Atkins. Other evaluation equipment for evaluating liquids and/or emulsions is well known and can be used with the provided methods.

2. General Methods for Making the Pre-emulsion Compositions

In general, the provided methods for making the pre-emulsion compositions include steps for combining (e.g. mixing, heating and homogenizing) the ingredients of the compositions, typically in one or more vessels, to form the pre-emulsion compositions, and for packaging the compositions, e.g. by transfer to a holding/packaging vessel or a packaging or storage container. In some examples, the methods include additional steps, such as evaluation, addition of further ingredients, packaging and filtering. The provided methods can be carried out using a bench-top manufacturing process (typically for small batch sizes). Alternatively, the methods can be carried out using a scaled-up manufacturing process (typically for larger batch sizes). Each of the provided pre-emulsion compositions can be made using either a scaled-up process or a bench-top process. In one example, after the pre-emulsion composition first is made using the bench-top process, the method is scaled up to make larger quantities of the pre-emulsion composition using the scaled-up process. When formulating the pre-emulsion compositions according to the provided methods, the initial pre-emulsion composition typically is made by a bench-top method. In one example of the formulation methods, a selected formulation then is made using a scaled-up process. Any of the pre-emulsion compositions provided herein can be made with the provided methods, using either manufacturing process. Any method described herein, where the bench-top method is used, can be scaled-up for production of the pre-emulsion compositions using the scaled-up process.

Generally, the provided methods for making the pre-emulsion compositions include a first dissolving step, which typically includes mixing and heating the ingredients of the composition, for example, in a vessel. The provided methods further include a homogenizing step, e.g. mixing with a homogenizer. Typically, one or more of the dissolving and/or homogenizing steps (e.g. standard mixer and/or homogenizer) is performed simultaneously with heating. Alternatively, the steps can be performed sequentially in any order, simultaneously, or partially simultaneously.

Typically, for heating, the ingredients are heated to a low heat temperature, for example, to 60° C. or about 60° C.

Typically, the methods generally include a packaging step, whereby the mixed and heated composition is packaged, for example, transferred, e.g. hot filled into a container, e.g. a packaging container. Typically, the composition is cooled in the packaging container.

The provided methods can include additional steps, for example, evaluation steps, steps for adding additional ingredients, purification (e.g. filtration) steps, and/or packaging/holding steps, as detailed below.

a. Combining the Ingredients i. Weighing the Ingredients

Typically, the ingredients are weighed and/or measured, for example, using one or more scales (e.g. one or more of the scales described herein), before they are added to the mixing vessel (e.g. any vessel described herein). In one example, the amount of each ingredient to be added is determined according to the provided methods for formulating the pre-emulsion compositions. Typically, the desired concentration, by weight (w/w), of the final pre-emulsion composition is used to calculate the amount of each ingredient that is added to the vessel. Alternatively, the desired volume per weight, volume per volume or weight per volume can be used to calculate the correct amount of an ingredient to be measured and added to the vessel.

ii. Dissolving First Ingredient(s)—Standard Mixer

Typically, a subset of the ingredients, initial ingredients are added first to the mixing vessel. In one example, the initial ingredients are all or most of the ingredients, but not including the non-polar compound(s). In another example, the ingredients are all or most of the ingredients, but not including the surfactant, for example, the TPGS surfactant. Typically, in order to dissolve the initial ingredients, these first ingredient(s) are mixed in the mixing vessel using a standard mixer (e.g. any of the standard mixers described herein) and heated, typically simultaneously or, in part, simultaneously, using a heating apparatus (e.g. any of the heating apparatuses described herein). Typically, the ingredients are heated such that the ingredients reach a low heat temperature, for example, between about 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically, 60° C. or 60° C. In another example, the initial ingredients are heated to a higher temperature, for example, to 80° C. or about 80° C., for example, 82.2° C. In this example, the ingredients are heated to this higher temperature, typically for an hour, for example, until dissolved. In this example, the mixture typically is filtered, for example, using a 100 micron filter, before proceeding to the next step, e.g. addition of additional ingredients, for example, the surfactant, and homogenization. Typically, mixing and/or heating of ingredients in the vessel is continued until the ingredients dissolve—e.g. until they become homogeneous, for example at the heated temperature. One or more temperature meters can be used to measure the temperature during mixing.

iii. Homogenizing the Mixture

Typically, after the initial ingredients are dissolved, additional ingredients are added to the vessel before homogenizing the mixture. In one example, the additional ingredients added prior to homogenization are one or more non-polar compound(s), e.g. non-polar active ingredient(s) (and optionally, any other ingredients, for example, emulsion stabilizer).

In another example, the one or more additional ingredients added prior to homogenization is one or more surfactants, for example, TPGS. The additional ingredient(s) is added to the vessel, with continued heating and mixing. In this step, the ingredients typically are homogenized, using a homogenizer (e.g. any of the described homogenizers). Typically, the homogenizing is carried out in the vessel containing the dissolved initial ingredients (e.g. the same vessel). Alternatively, a different vessel can be used for addition of the non-polar active ingredient and homogenization. Typically, homogenization is carried out using a mixer that is capable of emulsifying liquids (e.g. a high-shear mixer), for example, a homogenizer, for example, a reversible homogenizer. Typically, the ingredients are homogenized while maintaining the heated temperature, for example between about 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically, 60° C. or about 60° C. Typically, the homogenizing is carried out using the mixer (e.g. homogenizer) at low speed, for example, low rpm, for example, between 850 or about 850 rpm and 1200 or about 1200 rpm, for example, 850, 900, 950, 1000, 1050, 1100, 1150 or 1200 rpm.

The ingredients typically are homogenized, continuously or intermittently, until the ingredients become homogeneous at the temperature, for example, at between about 45° C. or about 45° C. and 85° C. or about 85° C., for example, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85° C., typically, 60° C. or about 60° C. In one example, the baffle plate of the mixer is adjusted, for example, by moving the baffle plate further down into the mixture or further up out of the mixture, to control the type of mixing, for example, to switch from downward flow to upward flow and vice versa, during mixing of the composition. In another example, the homogenizer can be adjusted to increase or decrease shear or to maintain the shear at a particular speed. Methods for homogenizing ingredients are well known and other methods can be used to homogenize in the provided methods.

iv. Ingredients and Order of Addition

Typically, the ingredients added to the vessel to make the provided pre-emulsion compositions are hydrophobic or amphipathic ingredients. In one example, there is no aqueous ingredient added to the composition. In another example, less than 1% or about 1% or less than 5% or about 5%, by weight, of the composition is represented by aqueous ingredients. The ingredients can be added simultaneously and/or sequentially, in a specific order. In one example, one or more ingredients (e.g. initial ingredients) is added first and heated, prior to addition of further ingredient(s). For example, the non-polar compound can be mixed and heated with one or more solvent, for example, an oil, for example, flaxseed oil and/or Vitamin E oil, until the non-polar compound is dissolved in the oil, prior to addition of the other ingredients. In one example, when the composition includes one or more of a surfactant (e.g. a TPGS surfactant), a preservative, and non-polar active ingredient, these ingredients are added sequentially, in the following order: 1) surfactant(s), 2) preservative(s), 3) 4) non-polar active ingredient(s). In this example, the non-polar active ingredient(s) typically is added after the other ingredients have dissolved, prior to homogenization.

In another example, when the composition includes one or more of a surfactant (e.g. a TPGS surfactant), a preservative, and non-polar active ingredient, these ingredients are added sequentially, in the following order: 1) preservative(s), 2) non-polar active ingredient(s), 3) surfactant(s). In this example, the surfactant typically is added after the other ingredients have dissolved (and been filtered) prior to homogenization. In another example, when the composition includes one or more of a surfactant, a preservative, solvent and non-polar active ingredient, these ingredients are added sequentially, in the following order: 1) solvent(s), 2) preservative(s), 3) non-polar active ingredient(s), 4) surfactant(s). In this example, the surfactant(s) typically is added after the other ingredients have dissolved, prior to homogenization.

In one example, when the composition includes a surfactant, particularly when the surfactant is a surfactant that is solid at room temperature, for example, tocopherol polyethylene glycol succinate surfactant, the surfactant is the first ingredient added to the vessel. In another example, the surfactant, for example, TPGS, is the last ingredient added to the vessel. Typically, when the ingredients include an emulsion stabilizer, the emulsion stabilizer is the last ingredient added to the vessel. Typically, the non-polar compound either is the last ingredient added to the vessel, or is added immediately prior to addition of the emulsion stabilizer, which is the last ingredient added to the vessel. In this example, the non-polar active ingredient(s) typically is added after the other ingredients have dissolved, prior to homogenization.

b. Additional Steps

Typically, one or more additional steps is carried out, following mixing and heating the ingredients. For example, the composition can be evaluated (e.g. by measuring pH and/or temperature of the pre-emulsion composition). In another example, one or more additional ingredients can be added to the composition. In another example, the pre-emulsion composition is transferred to a holding vessel or a packaging vessel, for example, a holding/packaging vessel, for example, a holding/packaging tank. In another example, the nanoemulsion is purified, for example, filtered, prior to use. In one example, addition of additional ingredients, evaluation and/or purification, can be carried out in the holding/packaging vessel. Other additional steps can be carried out prior to use.

i. Additional Ingredients

In one example, additional ingredients, for example pH adjusters and/or flavors, can be added to the composition after it is formed. In one example, citric acid and/or phosphoric acid is added to adjust the pH, for example, until the pH reaches a pH between 2.5 and 3.5, typically, between 2.6 or about 2.6 and 3.2 or about 3.2, for example, 2.6, 2.7, 2.8, 2.9, 3.0, 3.1, or 3.2. In another example, one or more flavors is added to the pre-emulsion composition, for example, to improve the taste and/or smell of the pre-emulsion composition and/or beverages containing the pre-emulsion composition. Other additional ingredients also can be added to the composition. Typically, the additional ingredients are added to the vessel containing the composition, for example, the mixing vessel, or another vessel, for example, a holding/packaging vessel. Typically, the composition is mixed (e.g. using any of the described mixers, typically standard mixers), while the additional ingredients are added.

ii. Evaluation of the Pre-emulsion Composition

Typically, the pre-emulsion composition is evaluated prior to use. Typically, the pH and/or temperature are measured, for example, using a pH and temperature meter. In one example, the pH and/or temperature are evaluated after additional ingredients have been added. In one example, further ingredients can be added to adjust the parameters after evaluation.

iii. Filtering

Typically, after all the ingredients have been added and made homogeneous in the composition, the composition is filtered using an end-product filter (e.g. a 100 micron end-product filter), to remove any impurities.

iv. Transfer and/or Packaging

In one example, the ingredients, typically the mixture of ingredients (e.g. the pre-emulsion composition) is transferred, using one or more transfer means, to another vessel, for example, a holding or packaging vessel and or a storage container. Any transfer means can be used. For example, any means for transferring the contents of one vessel to another vessel as described above, for example, transfer pumps and associated equipment, for example, sanitary fittings, hoses and/or ball valves; and manual transfer means, for example, pouring and/or pipetting means or other known transfer means. In some examples, the mixture is kept clean, for example, sterile during transfer, for example, by using transfer means with sanitary fittings and/or combining the phases in a sterile environment.

In one example, the mixture is transferred to a holding tank. In another example, the pre-emulsion composition, after being made and filtered, is transferred, e.g. by hot filling while the composition is still a liquid, to a storage container, e.g. a vial, plastic bottle, or scholle bag-in-a-box type packaging. Typically, the composition is allowed to cool naturally in the storage container. Alternatively, a cooling apparatus, e.g. a refrigerator, freezer or water bath, can be used to cool the composition in the storage container. Typically, the composition solidifies as it cools in the storage container, e.g. becoming a waxy solid.

3. Bench-top Process

In one example of the provided methods for making the pre-emulsion compositions, the steps of the methods are carried out using a bench-top manufacturing process, which is carried out on a bench, counter, table or other surface. Typically, the bench-top process is used to make compositions having relatively smaller volumes than those made with the scaled-up process, for example, volumes less than 1 L or about 1 L or less than 1 gallon or about 1 gallon, for example, less than about 500 mL, for example, 1000, 900, 800, 700, 600, 500, 450, 400, 350, 300, 250, 200, 150, 100, 50 or less.

For the bench-top process, the equipment typically is sufficiently compact to be used on a bench top or other similar surface, typically sufficiently compact to be moved, for example, lifted, by the artisan using the methods. For example, the vessels typically are bench-top vessels, for example, flasks, beakers, vials, measuring containers, bottles and/or other bench-top containers. In one example, the vessels in the bench-top process is a Pyrex® beaker. Typically, the mixers are mixers that can be used in the bench-top vessels, for example, standard mixers, including hand-held mixers, stir rods, stir bars, magnetic mixers and overhead mixers, for example, mechanical and/or electric overhead mixers and/or other mixers that can be used in the vessels. Exemplary of appropriate bench-top mixers are standard mixers, for example, standard mixers sold by IKA®, for example, overhead IKA® mixers, for example, model Nos. RW-14 Basic and RE-16S, which are laboratory stirrers and can be used to mix ingredients, e.g. to mix and dissolve the initial ingredients. Also exemplary of appropriate bench-top mixers are homogenizers, for example, reversible homogenizers, including The Arde Barinco reversible homogenizer, Model no. CJ-4E, which can be used to emulsify the phases. Typically, the heating apparatuses are those that can be used with the bench-top vessels, for example, hot plates. The cooling apparatuses typically are apparatuses suited for use with the smaller bench-top vessels, for example, ice baths and/or water baths into which the vessels can be placed, for example, for rapid cooling. The evaluation means used in the bench-top process, for example, the temperature and/or pH meters, typically are capable of being placed in the bench-top vessels.

Generally, for the bench-top process, the dissolving step is carried out by mixing and heating in a bench-top vessel, for example, a flask, beaker, vial, measuring container, bottle and/or other bench-top container. The mixing typically is carried out using an appropriate bench-top mixer, for example, a standard mixer, such as a hand-held mixer, stir rod, stir bar, magnetic mixer and/or overhead mixer, for example, the mixer sold by IKA®, for example, overhead IKA® mixers, for example, model Nos. RW-14 Basic and RE-16S, which are laboratory stirrers. For homogenizing, a reverse homogenizer typically is used. Typically, heating the ingredients during mixing is carried out using a heating apparatus appropriate to the bench-top method, for example, a heating apparatus that one or more of the vessels can be placed upon, for example, a hot plate. Typically, transfer, e.g. transferring the composition into a storage container, packaging vessel or holding vessel, is carried out manually, for example, by pouring, pipetting and/or another manual transfer means.

4. Scaled-up Manufacturing Process

In another example of the provided methods for making the pre-emulsion compositions, the steps of the methods are carried out using a scaled-up manufacturing process, which typically is used when making emulsions having relatively larger volumes than those made with the bench-top process, for example, volumes greater than 1 L or about 1 L or greater than 1 gallon or about 1 gallon, for example, greater than about 500 mL, for example, at least 0.5 L, 1 L, 2 L, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 550, 600, 650, 700, 800, 900, 1000 or more gallons. In general, equipment used for the scaled-up process is compatible with these larger volume batches (batch sizes) of the pre-emulsion compositions. For example, the vessels typically are tanks, for example, water jacketed tanks, which are equipped with water jackets that can be used as heating apparatuses to heat the ingredients, for example, while mixing/homogenizing the ingredients. The water jackets typically are controlled via control panels. Similarly, the transfer means typically include transfer pumps and associated fittings, for example, ball valves and hoses. Exemplary of mixers that are used in the scaled-up process are standard mixers (for example, mounted mixers, for example LIGHTNING mixers, for example, Model XJC117 (a fixed-mount, gear drive high-flow mixer, and Model ND2. An exemplary scaled-up process is set forth in FIG. 1 and described in this section, below. The provided methods for making the pre-emulsion compositions can be performed using this exemplary scaled-up process, or any variation of the scaled-up process, for example, eliminating one or more steps of the exemplary process, adding one or more steps according to the provided method, and/or substituting steps and/or equipment according to the methods provided herein.

FIG. 1 sets forth a an exemplary scaled-up process 100 for making the liquid pre-emulsion composition. This exemplary scaled-up process includes the following steps:

a. Combining the Ingredients i. Dissolving the Initial Ingredients—Standard Mixing

After the initial ingredients (e.g. one or more ingredients typically not including the non-polar active ingredient) are weighed/measured, they are added to the mixing vessel. In this example of the scaled up process, set forth in FIG. 1, the vessel is a mixing tank 101. Typically, in the scaled-up method, the mixing tank is a water-jacketed tank. The initial ingredient(s) are mixed using a standard mixer 104, for example, a LIGHTNIN® mixer (for example, model no. XJC117, a fixed-mount gear drive high-flow mixer), attached to the tank, for example, mounted on the top of the tank. In this example, the heating apparatus, for heating the ingredients during mixing, is the water jacket of the water-jacketed tank; temperature on the water-jacket is controlled via a control pane. The ingredients are mixed and heated, typically to low heat (e.g. 60° C.), until dissolved, according to the provided methods.

ii. Addition of the Non-polar Compound and Homogenizing

In this example, set forth in FIG. 1, once the initial ingredients are dissolved (by heating and mixing with the standard mixer) additional ingredient(s), for example, the non-polar compound (e.g. non-polar active ingredient) is added, and the mixture is homogenized. In the example set forth in FIG. 1, to begin the homogenization step, a homogenizer 105 (e.g. an Arde Barinco, Inc. reversible homogenizer), mounted on the mixing tank, is turned on, for example, at 850-1200 rpm. The additional ingredient(s) (e.g. the non-polar active ingredient) is added and the mixture homogenized, typically while continuing to heat the mixture, e.g. while maintaining low heat. The mixture is homogenized by continued mixing with the homogenizer 105. The homogenizer can be adjusted, for example, by adjusting the baffle plate on the homogenizer to achieve and maintain an emulsion, for example, by moving the baffle plate further into the forming emulsion and/or further out of the forming mixture. The homogenization is continued, with heating, until the ingredients dissolve.

b. Additional Steps

After the homogenization step, one or more additional steps typically are carried out. In one example, the ingredients are transferred, via transfer means 102, which include a transfer pump (e.g. a Teel pump, model 2P377B, sold by Granger, Inc.), sanitary fittings, transfer hose(s) (e.g. food grade hoses sold by Sani-Tech West) and ball valve(s), to a packaging or holding tank 103. The packaging/holding tank can be used to add additional ingredients, to evaluate the composition, or to hold the composition. Typically, the pre-emulsion composition is filtered using an end-product filter 106, which is, for example, a 100 micron end-product filter. In the example shown in FIG. 1, the composition can be filtered directly from the mixing tank, or it can be filtered after transfer to the packaging/holding tank. The composition finally is transferred, for example, using transfer means 102, to a storage container 107. Typically, the composition is transferred into the storage container while it is still at a heated temperature, for example, between 48° C. or about 48° C. and 60° C. or about 60° C. In this example, the composition then solidifies (developing a waxy consistency) while in the storage container.

Variations of this exemplary scaled-up process (FIG. 1) also can be carried out using the provided methods, to make the pre-emulsion compositions. For example, by elimination and/or modification of one or more steps and/or equipment, according to the general methods provided herein.

D. Methods for Making the Liquid Dilution Compositions Containing the Diluted Pre-Emulsion Compositions Also provided herein are methods for diluting the pre-emulsion compositions to make liquid dilution compositions, typically, aqueous liquid dilution compositions, containing the non-polar compounds. Generally, the pre-emulsion composition is diluted into an aqueous medium, for example, a beverage, for example, soda, water milk, coffee, tea, juice, fitness drinks, nutritional beverage, nutritional supplement, or other aqueous food or beverage. The pre-emulsion composition and the aqueous medium can be mixed, for example, by stirring and/or blending or by any known mixing means. The pre-emulsion composition disperses into the aqueous medium to form an aqueous liquid dilution composition, for example, a clear or partially clear aqueous liquid dilution composition. The aqueous liquid dilution composition can be evaluated, for example, to assess the clarity, taste, smell, and/or stability of the liquid.

In one example, the pre-emulsion composition is diluted in the aqueous medium, for example, water by heating the aqueous medium, for example, by heating the aqueous medium, for example, to at least 40° C. or at least about 40° C., for example, 41, 42, 43, 44, 45, 46, 47, 48, 49, 50 or more ° C., for example, 48.9° C. (120° F. or about 120° F.). In this example, the pre-emulsion composition is added, at an appropriate dilution, as described herein, to the heated aqueous medium, and stirred until dispersed or dissolved in the solution. In one example, the pre-emulsion composition is heated before addition to the aqueous medium, for example, to at least 40° C. or at least about 40° C., for example, 41, 42, 43, 44, 45, 46, 47, 48, 49, 50 or more ° C., for example, 48.9° C. (120° F. or about 120° F.). In another example, the pre-emulsion composition is added to the medium without heating.

The resulting liquid dilution composition can then be cooled, for example, to room temperature, for example, 25° C. or about 25° C. Following dilution, the aqueous liquid dilution composition can be packaged, for example, by transferring to containers, for example, vials or beverage containers. In one example, a portion of the liquid dilution composition is transferred to vials for analysis, for example, evaluation of properties, such as clarity, turbidity, taste, smell, ringing, crystal formation and/or other properties.

Exemplary of equipment used for diluting the pre-emulsion compositions to form the liquid dilution compositions containing the diluted pre-emulsion compositions are beakers, for example, Pyrex® glass beakers, hot plates, for example, the Thermolyne hot plate, model number 846925 or model number SP46615, stir rods, temperature meters, for example, temperature probes, for example, Cooper Temperature Probes (model no. DPP400W) and scales, for example, the OHUAS 2.0 Kg scale (Model # CS2000) and/or the Sartorius Analytical Scale (model BA110S).

1. Dilutions

Typically, the provided pre-emulsion compositions can be diluted into aqueous media to form aqueous liquid dilution compositions over a wide range of dilutions. In one example, the pre-emulsion composition can be diluted so that the aqueous liquid dilution composition contains between 0.05 g or about 0.05 g and 10 g or about 10 g, typically between 0.05 g and 5 g, of the liquid pre-emulsion composition per 8 fluid ounces of the liquid, at least 8 fluid ounces of the liquid or less than 8 fluid ounces of the liquid, or per single serving of the liquid. For example, the pre-emulsion composition can be diluted so that the aqueous liquid dilution composition contains 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the pre-emulsion composition per 8 fluid ounces, about 8 fluid ounces, or at least 8 fluid ounces or at least about 8 fluid ounces of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the pre-emulsion composition is diluted so that the aqueous liquid dilution composition contains between 1 mL or about 1 mL and 10 mL or about 10 mL of the liquid pre-emulsion composition, for example, 1 mL, 2 mL, 3 mL, 4 mL, 5 mL, 6 mL, 7 mL, 8 mL, 9 mL or 10 mL of the pre-emulsion composition, per 8 fluid ounces, about 8 fluid ounces, at least 8 fluid ounces or at least about 8 fluid ounces, or less than 8 fluid ounces or less than about 8 fluid ounces, or per serving size, of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the liquid pre-emulsion composition is diluted so that the aqueous liquid dilution composition contains at least 10 mg or about 10 mg, typically at least 25 mg or about 25 mg, typically at least 35 mg, of the non-polar compound, for example, the non-polar active ingredient, per 8 fluid ounces (0.236588 liters) or about 8 fluid ounces, at least 8 fluid ounces (0.236588 liters) or at least about 8 fluid ounces of the aqueous medium, or less than 8 ounces or less than about 8 ounces (0.236588 liters), or per serving size, of the aqueous medium; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar compound per at least 8 fluid ounces or at least about 8 fluid ounces (0.236588 liters) of aqueous medium.

2. Analyzing the Aqueous Liquid Dilution Compositions Containing the Liquid Pre-emulsion Compositions Properties of the aqueous liquid dilution compositions containing the liquid pre-emulsion compositions can be evaluated using a number of different evaluation means. For example, the clarity; desirability for human consumption, for example, pleasant taste, and/or smell, for example, lack of "fishy" taste/smell, lack of "ringing" and lack of crystal formation; stability, for example, lack of oxidation, "ringing," precipitation and/or visible phase separation, over time; and safety for human consumption, can be evaluated. Several of these properties can be evaluated empirically, for example, by observing the liquids immediately or over time, or by smelling and/or tasting the liquids. In one example, after evaluation of the aqueous liquid dilution compositions, the pre-emulsion compositions are re-formulated to adjust one or more parameters. In another example, the dilution factor can be adjusted.

a. Clarity/Turbidity

Clarity of the aqueous liquid dilution compositions can be evaluated using one or more of several approaches, or example, empirical observation, measurement of particle size and/or measurement of a turbidity value. The measurement can be qualitative or quantitative. In one example, a particular quantitative or qualitative clarity value is specified. In another example, the clarity of a liquid can be expressed in relation to the clarity of another liquid, for example, an aqueous liquid dilution composition made according to the provided methods, or a beverage, for example, a beverage that does not contain the liquid pre-emulsion composition. In this example, the liquid can be as clear as, less clear, or more clear than the other liquid. For example, an aqueous liquid dilution composition containing the liquid pre-emulsion composition diluted in a beverage can be as clear or about as clear as the same beverage that does not contain the pre-emulsion composition. Either type of evaluation can be done qualitatively, for example, by empirical evaluation, or quantitatively, for example, by taking a measurement of particle size or turbidity.

i. Empirical Evaluation

In one example, the clarity/turbidity of the aqueous liquid dilution composition is evaluated qualitatively, for example, by observation. In one example, a liquid is considered clear if it does not have a cloudy appearance and/or if it contains no particles or few particles that are observable with the naked eye. In another example, the liquid can be considered relatively clear or relatively turbid based on comparison to other liquids, for example, water, fruit juice, soda, and/or milk and/or other aqueous liquid dilution composition(s) made according to the provided methods. For example, the aqueous liquid dilution composition can be as clear or about as clear as water or another liquid, for example, a beverage. For example, the liquid containing the liquid pre-emulsion composition diluted in a beverage can be as clear or about as clear as the beverage that does not contain the liquid pre-emulsion composition. In a related example, the liquid can be clear or partially clear when there is no substantial difference, for example, no observable difference, between the aqueous liquid dilution composition containing the pre-emulsion composition and the aqueous medium that does not contain the pre-emulsion composition. A clear liquid is not necessarily colorless. For example, a yellow liquid that contains no (or few) visible particles or cloudiness can be clear. In another example, the lack of crystal formation or of "ringing" can be indicative of a clear liquid.

ii. Particle size

In another example, clarity/turbidity are assessed by quantitatively measuring particle size and/or number of particles, in the aqueous liquid dilution composition. In this example, the clarity can be expressed as a numerical representation of the particle size, or as a comparison to the particle size of another liquid.

Methods for measuring particle size of liquids are well known. Any method for measuring particle size can be used, provided that it is sensitive to the particle size in the expected and/or appropriate ranges of the provided aqueous liquid dilution compositions. For example, particle size analysis is available commercially, for example, from Delta Analytical Instruments, Inc., North Huntingdon, Pa. In one example, the particle size of the aqueous liquid dilution composition is measured, for example, by Delta Analytical Instruments, Inc., using a light-scattering analyzer, for example, a dynamic light scattering analyzer, for example, the Horiba® LB-550, which can measure particle sizes within a range of 0.001 micron to 6 micron and uses a Fourier-Transform/Iterative Deconvolution technique for reporting data and can measure sample concentrations from ppm to 40% solids; the Horiba® LA-920, which is a laser light-scattering instrument having an He—Ne laser and a tungsten lamp that can determine particle sizes from 0.02 micron to 2000 micron using Mie Theory; and other analyzers available from Delta Analytical Instruments, Inc.

Alternatively, particle size can be measured by viewing the liquid under a microscope under magnification, for example, a 640× magnification. Particle size then can be measured by comparison to a measuring standard, for example, a ruler, which also is viewed under the magnification. In one example, particles about 25 nm or greater than about 25 nm are visible, while particles less than 25 nm are not visible, for example under a 640× magnification.

iii. Turbidity Measurement

In another example, the clarity/turbidity of the liquid is evaluated and/or expressed using a turbidity measurement, for example, Nephelometric Turbidity Units (NTU). In this example, turbidity is measured optically, to obtain a value indicating the cloudiness or haziness of the liquid, which correlates with the number and size of particles suspended in the liquid. The more clear a liquid is, the lower its turbidity value. Turbidity can be measured optically, for example, using a nephelometer, an instrument with a light and a detector. The nephelometer measures turbidity by detecting scattered light resulting from exposure of the aqueous liquid dilution composition to an incident light. The amount of scattered light correlates with the amount and size of particulate matter in liquid, and thus, the clarity. For example, a beam of light will pass through a sample having low turbidity with little disturbance, creating very little scattered light, resulting in a low turbidity (NTU) value reading. Other methods for measuring turbidity can be used, including commercial services for measuring turbidity, for example, the services available through ACZ Laboratories, Inc., Steamboat Springs, Colo.

The following examples are included for illustrative purposes only and are not intended to limit the scope of the invention.

E. EXAMPLES

Example 1

General Procedure Used to Make the Pre-emulsion Compositions of Examples 2-7

Tables 2A(i)-7F below, set forth ingredients that were included in a plurality of different pre-emulsion compositions, described in Examples 2A through 7F. The pre-emulsion compositions were made according to the provided methods. Each of the pre-emulsion compositions contained one or more non-polar active ingredients.

The non-polar active ingredient(s) used in each pre-emulsion composition is/are described in each individual Example. The surfactant used in each pre-emulsion composition was a tocopherol polyethylene glycol succinate surfactant (the TPGS surfactant sold under the name Vitamin E TPGS® by Eastman Chemical Company). The preservative used in each pre-emulsion composition was a natural (GRAS-certified) preservative, benzyl alcohol.

In some of the Examples (where indicated), a solvent was used as an ingredient in the pre-emulsion composition. In these Examples, the solvent was Vitamin E oil, sold by ADM Natural Health and Nutrition, Decatur, Ill., under the name Novatol™ 5-67 Vitamin E (D-alpha-Tocopherol; ADM product code 410217). This oil contained at least 67.2% Tocopherol and approximately 32.8% soybean oil. Pre-emulsion compositions similar to the pre-emulsion compositions set forth in these examples alternatively could be made using an alternative or additional solvent(s), for example, a Flaxseed oil solvent, for example, the flaxseed oil from Sanmark LLC, Greensboro, N.C. (Sanmark Limited, Dalian, Liaoning Province, China), which contains not less than (NLT) 50% C18:3 alpha-linolenic acid.

Each of Tables 2A(i)-7F sets forth, for each pre-emulsion composition, the total milligrams (mg) per serving and the mg of each ingredient per serving (serving size is indicated), the percentage, by weight (of the total pre-emulsion composition), for each ingredient, the amount (g) of each ingredient that was added to make a batch of the indicated batch size (g).

Each of the pre-emulsion compositions set forth in Examples 2A-7F was made using a bench-top process according to the provided methods. Each of the pre-emulsion compositions could be made alternatively by scaling up the bench-top process, to make the pre-emulsion compositions using a scaled-up manufacturing process of the provided methods, for example, to make larger batch sizes of the pre-emulsion compositions in the following Examples. Accordingly, each of the pre-emulsion compositions in Examples 2A-7F also can be made with the provided methods, using the scaled-up process.

The bench-top process for making the pre-emulsion compositions in Examples 2A-7F was carried out using the following general steps. Further details for each pre-emulsion composition are provided in each individual example.

For each of the pre-emulsion compositions set forth in Examples 2A-7F below, the indicated amount of each ingredient was weighed using a Toledo Scale (Model GD13x/USA), Sartorius Basic Analytical Scale (Model BA110S) or an OHAUS Scale (Model CS2000). Selection of scale was dependent on the weight of each ingredient being weighed.

The initial ingredients (all ingredients except the non-polar active ingredient(s)) then were added, in the indicated amounts (g/batch), to a vessel (a Pyrex® beaker), and mixed using a standard mixer (IKA® model No. RE-16 1 S, which is an overhead mixer (laboratory stirrer) compatible with the bench-top process). While mixing, the ingredients were heated using a heating apparatus, which was a hot plate (a Thermolyne hot Plate Model #SP46615), to reach a temperature of 60° C.

Once these initial ingredients had dissolved, e.g. formed a homogeneous mixture, and reached the desired temperature, e.g. 60° C., the non-polar active ingredient(s) was/were added. The ingredients then were homogenized by placing a reversible homogenizer (Arde Barinco, Inc.; Model CJ-4E) in the vessel (beaker) and turning it on at 850-1200 RPM. Mixing with the homogenizer was continued while maintaining the temperature using the hot plate. The baffle plate on the homogenizer was adjusted to achieve and maintain an emulsion, for example, by moving the baffle plate further into and/or out of the ingredient mixture. The mixture was homogenized until it became homogeneous at 60° C.

Unless otherwise indicated, when the ingredients included a surfactant, a preservative and one or more non-polar active ingredients, these ingredients were added sequentially, in the following order: 1) surfactant; 2) preservative; 3) non-polar active ingredient(s). When the ingredients included a surfactant, a preservative, a solvent and one or more non-polar active ingredient(s), these ingredients were added sequentially, in the following order: 1) surfactant; 2) preservative; 3) solvent(s); 4) non-polar active ingredient(s). The ingredients were heated with the hot plate until the temperature reached 60° C. A temperature meter (temperature probe (Model #DPP400W, Cooper-Atkins)) was used to evaluate (measure) the temperature of the mixing ingredients.

The composition then was filtered, using a 100 micron end-product filter and then packaged (transferred) by filling into one or more storage containers, for example, plastic bottles or 5 gallon pails, where it was cooled to room temperature (about 25° C.). Alternatively, the mixture could be packaged into a bag-in-a-box type storage container. The mixture became a solid at room-temperature, having a waxy consistency. Thus, each of the pre-emulsion compositions in Examples 2-7 was a semi-solid or solid at room temperature, having a waxy consistency, and became liquid upon heating, for example, to 60° C.

Example 2

Pre-emulsion Compositions Having DHA-Containing Non-Polar Compounds

Examples 2A-B set forth the details of pre-emulsion compositions containing non-polar compounds containing the omega-3 polyunsaturated fatty acid, DHA. These pre-emulsion compositions were made using the general procedure outlined in Example 1, above.

Example 2A

Pre-emulsion Compositions Having Fish Oil Non-Polar Compounds

Tables 2A(i)-(vi) set forth the ingredients that were included in a plurality of pre-emulsion compositions having non-polar active ingredients containing fish oil, which contain different amounts of the omega-3 polyunsaturated fatty acids, DHA and EPA. These pre-emulsion compositions were made using the general procedure outlined in Example 1, above. Each of the pre-emulsion compositions set forth in Tables 2A(i)-(vi) used one of two different fish oil non-polar active ingredients. The first fish oil-containing non-polar active ingredient (used in the pre-emulsion compositions set forth in Tables 2A(i)-(ii)) was Denomega™ 100, fish oil, which contained about 13% DHA and about 13% EPA. The second fish oil-containing non-polar active ingredient (used in the pre-emulsion compositions set forth in Tables 2A(iii)-(vi)) was Omega-3 Fish Oil EE, made by O3C Nutraceuticals, supplied by Jedwards International Inc., Quincy, Mass., which contained about 70% (74%) DHA and about 10% (9.3%) EPA.

TABLE 2A(i)

Pre-emulsion composition having 10% of a Fish Oil-Containing Non-Polar Active Ingredient and 89.5% TPGS

| Ingredient | mg/ 0.5 mL serving | Percent (by weight) of pre-emulsion composition | g/batch |
|---|---|---|---|
| Denomega ™ 100 Fish Oil (13% EPA, 13% DHA) (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 2A(ii)

Pre-emulsion composition having 30% of a Fish Oil-Containing Non-Polar Active Ingredient and 69.5% TPGS

| Ingredient | mg/ 0.5 mL serving | Percent (by weight) of pre-emulsion composition | g/batch |
|---|---|---|---|
| Denomega ™ 100 Fish Oil (13% EPA, 13% DHA) (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 2A(iii)

Pre-emulsion composition having 10% of a Fish Oil-Containing Non-Polar Active Ingredient and 89.5% TPGS

| Ingredient | mg/ 0.5 mL serving | Percent (by weight) of pre-emulsion composition | g/batch |
|---|---|---|---|
| : Omega-3 Fish Oil EE, (10% EPA, 70% DHA) (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 2A(iv)

Pre-emulsion composition having 20% of a Fish Oil-Containing Non-Polar Active Ingredient and 79.5% TPGS

| Ingredient | mg/ 0.5 mL serving | Percent (by weight) of pre-emulsion composition | g/batch |
|---|---|---|---|
| : Omega-3 Fish Oil EE, (10% EPA, 70% DHA) (Non-Polar Active Ingredient) | 100 | 20 | 20 |
| Tocopherol Polyethylene Glycol Succinate (surfactant) | 397.5 | 79.5 | 79.5 |
| Benzyl alcohol (preservative) | 2.5 | 0.5 | .5 |
| Totals | 500.000 | 100.0000 | 100 |

TABLE 2A(v)

Pre-emulsion composition having 30% of a Fish Oil-Containing Non-Polar Active Ingredient and 69.5% TPGS

| Ingredient | mg/ 0.5 mL serving | Percent (by weight) of pre-emulsion composition | g/batch |
|---|---|---|---|
| Omega-3 Fish Oil EE, (10% EPA, 70% DHA) (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 2A(vi)

Pre-emulsion composition having 10% of a Fish Oil-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| Omega-3 Fish Oil EE, (10% EPA, 70% DHA) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

Example 2B

Pre-emulsion Compositions Having Algae Oil Non-Polar Compounds

Tables 2B(i)-(iv) set forth the ingredients that were included in pre-emulsion compositions containing an algae oil non-polar active ingredient. This algae oil non-polar active ingredient contained 35% of the omega-3 polyunsaturated fatty acid, DHA. These pre-emulsion compositions were made using the general procedure outlined in Example 1, above.

TABLE 2B(i)

Pre-emulsion composition having 10% of an Algae Oil-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| Algae Oil (35% DHA) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

TABLE 2B(ii)

Pre-emulsion composition having 20% of an Algae Oil-Containing Non-Polar Active Ingredient and 79.5% TPGS

| Ingredient | mg/ 0.5 mL serving | Percent (by weight) of pre-emulsion composition | g/batch |
|---|---|---|---|
| Algae Oil (35% DHA) | 100 | 20 | 20 |
| Tocopherol Polyethylene Glycol Succinate (surfactant) | 397.5 | 79.5 | 79.5 |
| Benzyl alcohol (preservative) | 2.5 | 0.5 | .5 |
| Totals | 500.000 | 100.0000 | 100 |

TABLE 2B(iii)

Pre-emulsion composition having 20% of an Algae Oil-Containing Non-Polar Active Ingredient and 79.5% TPGS

| Ingredient | mg/ 0.5 mL serving | Percent (by weight) of pre-emulsion composition | g/batch |
|---|---|---|---|
| Algae Oil (35% DHA) | 100 | 20 | 56 |
| Tocopherol Polyethylene Glycol Succinate (surfactant) | 397.5 | 79.5 | 222.6 |
| Benzyl alcohol (preservative) | 2.5 | 0.5 | 1.4 |
| Totals | 500.000 | 100.0000 | 280 |

TABLE 2B(iv)

Pre-emulsion composition having 30% of an Algae Oil-Containing Non-Polar Active Ingredient and 69.5% TPGS

| Ingredient | mg/ 0.5 mL serving | Percent (by weight) of pre-emulsion composition | g/batch |
|---|---|---|---|
| Algae Oil (35% DHA) | 150 | 30 | 84 |
| Tocopherol Polyethylene Glycol Succinate (surfactant) | 347.5 | 69.5 | 194.6 |
| Benzyl alcohol (preservative) | 2.5 | 0.5 | 1.4 |
| Totals | 500.000 | 100.0000 | 280 |

Example 3

Pre-emulsion Compositions Having ALA Containing Non-Polar Compounds (Flaxseed Oil)

Tables 3A-3D set forth the ingredients that were included in pre-emulsion compositions containing a flaxseed oil non-polar active ingredient. The flaxseed oil non-polar active ingredient, obtained from Sanmark LLC, Greensboro, N.C. (Sanmark Limited, Dalian, Liaoning Province, China), contained not less than (NLT) 50% C18:3 alpha-linolenic acid. These pre-emulsion compositions were made using the general procedure outlined in Example 1, above.

TABLE 3A

Pre-emulsion composition having 10% of a Flaxseed Oil-Containing Non-Polar Active Ingredient and 89.5% TPGS

| Ingredient | mg/ 0.5 mL serving | Percent (by weight) of pre-emulsion composition | g/batch |
|---|---|---|---|
| Flaxseed Oil (NLT 50% C18:3 alpha linolenic acid) (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 3B

Pre-emulsion composition having 20% of a Flaxseed Oil-Containing Non-Polar Active Ingredient and 79.5% TPGS

| Ingredient | mg/ 0.5 mL serving | Percent (by weight) of pre-emulsion composition | g/batch |
|---|---|---|---|
| Flaxseed Oil (NLT 50% C18:3 alpha linolenic acid) (Non-Polar Active Ingredient) | 100 | 20 | 30 |
| Tocopherol Polyethylene Glycol Succinate (surfactant) | 397.5 | 79.5 | 119.25 |
| Benzyl alcohol (preservative) | 2.5 | 0.5 | .75 |
| Totals | 500.000 | 100.0000 | 150 |

TABLE 3C

Pre-emulsion composition having 30% of a Flaxseed Oil-Containing Non-Polar Active Ingredient and 69.5% TPGS

| Ingredient | mg/ 0.5 mL serving | Percent (by weight) of pre-emulsion composition | g/batch |
|---|---|---|---|
| Flaxseed Oil (NLT 50% C18:3 alpha linolenic acid) (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 3D

Pre-emulsion composition having 10% of a Flaxseed Oil-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| Flaxseed Oil (NLT 50% C18:3 alpha linolenic acid) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

Example 4

Pre-emulsion Compositions Having Omega-6 Polyunsaturated Fatty Acid Containing Non-Polar Compounds (GLA Borage-Oil)

Tables 4A-4D set forth the ingredients that were included in pre-emulsion compositions containing a non-polar active ingredient containing an omega-6 fatty acid. The non-polar active ingredient was a borage oil compound, obtained from Sanmark LLC, Greensboro, N.C. (Sanmark Limited, Dalian, Liaoning Province, China), which was derived by pressing and isolating oil from the seeds of Borago officinalis L. This oil contained not less than (NLT) 22% C18:3 gamma-linolenic acid (GLA). These pre-emulsion compositions were made using the general procedure outlined in Example 1, above.

TABLE 4A

Pre-emulsion composition having 10% of a Borage Oil-Containing Non-Polar Active Ingredient and 89.5% TPGS

| Ingredient | mg/ 0.5 mL serving | Percent (by weight) of pre-emulsion composition | g/batch |
| --- | --- | --- | --- |
| Borage Oil (NLT 22% C18:3 gamma-linolenic acid (GLA)) (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 4B

Pre-emulsion composition having 20% of a Borage Oil-Containing Non-Polar Active Ingredient and 79.5% TPGS

| Ingredient | mg/ 0.5 mL serving | Percent (by weight) of pre-emulsion composition | g/batch |
| --- | --- | --- | --- |
| Borage Oil (NLT 22% C18:3 gamma-linolenic acid (GLA)) (Non-Polar Active Ingredient) | 100 | 20 | 30 |
| Tocopherol Polyethylene Glycol Succinate (surfactant) | 397.5 | 79.5 | 119.25 |
| Benzyl alcohol (preservative) | 2.5 | 0.5 | .75 |
| Totals | 500.000 | 100.0000 | 150 |

TABLE 4C

Pre-emulsion composition having 30% of a Borage Oil-Containing Non-Polar Active Ingredient and 69.5% TPGS

| Ingredient | mg/ 0.5 mL serving | Percent (by weight) of pre-emulsion composition | g/batch |
| --- | --- | --- | --- |
| Borage Oil (NLT 22% C18:3 gamma-linolenic acid (GLA)) (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 4D

Pre-emulsion composition having 10% of a Borage Oil-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
| --- | --- | --- | --- |
| Borage Oil (NLT 22% C18:3 gamma-linolenic acid (GLA)) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

Example 5

Pre-emulsion Compositions Having Saw Palmetto Extract Non-Polar Compounds

Tables 5A-5D set forth the ingredients that were included in pre-emulsion compositions containing a non-polar active ingredient containing saw palmetto extract. The non-polar active ingredient was the Saw Palmetto, Lipophilic Extract, commercially available from Natural Medicinals, Inc., Felda, Fla., which contained between about 85% and 90% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture. These pre-emulsion compositions were made using the general procedure outlined in Example 1, above.

TABLE 5A

Pre-emulsion composition having 10% of a Saw Palmetto Extract-Containing Non-Polar Active Ingredient and 89.5% TPGS

| Ingredient | mg/ 0.5 mL serving | Percent (by weight) of pre-emulsion composition | g/batch |
| --- | --- | --- | --- |
| Saw Palmetto Extract (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 5B

Pre-emulsion composition having 20% of a Saw Palmetto Extract-Containing Non-Polar Active Ingredient and 79.5% TPGS

| Ingredient | mg/ 0.5 mL serving | Percent (by weight) of pre-emulsion composition | g/batch |
| --- | --- | --- | --- |
| Saw Palmetto Extract (Non-Polar Active Ingredient) | 100 | 20 | 30 |

TABLE 5B-continued

Pre-emulsion composition having 20% of a Saw Palmetto Extract-Containing Non-Polar Active Ingredient and 79.5% TPGS

| Ingredient | mg/ 0.5 mL serving | Percent (by weight) of pre-emulsion composition | g/batch |
|---|---|---|---|
| Tocopherol Polyethylene Glycol Succinate (surfactant) | 397.5 | 79.5 | 119.25 |
| Benzyl alcohol (preservative) | 2.5 | 0.5 | .75 |
| Totals | 500.000 | 100.0000 | 150 |

TABLE 5C

Pre-emulsion composition having 30% of a Saw Palmetto Extract-Containing Non-Polar Active Ingredient and 69.5% TPGS

| Ingredient | mg/ 0.5 mL serving | Percent (by weight) of pre-emulsion composition | g/batch |
|---|---|---|---|
| Saw Palmetto Extract (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 5D

Pre-emulsion composition having 10% of a Saw Palmetto Extract-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| Saw Palmetto Extract (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

Example 6

Pre-emulsion Compositions Having CLA Containing Non-Polar Compounds

Tables 6A-6D set forth the ingredients that were included in pre-emulsion compositions containing a non-polar active ingredient containing conjugated linolenic acid (CLA). The non-polar active ingredient was a conjugated linolenic acid (CLA) compound, obtained from Sanmark, LTD (Dalian, Liaoning Province, China; product code 01057-A80), containing 70% CLA. These pre-emulsion compositions were made as described in Example 1, above.

TABLE 6A

Pre-emulsion composition having 10% of a CLA-Containing Non-Polar Active Ingredient and 89.5% TPGS

| Ingredient | mg/ 0.5 mL serving | Percent (by weight) of pre-emulsion composition | g/batch |
|---|---|---|---|
| CLA (70%) (Non-Polar Active Ingredient) | 50 | 10 | 15 |
| Tocopherol Polyethylene Glycol Succinate (surfactant) | 447.5 | 89.5 | 134.25 |
| Benzyl alcohol (preservative) | 2.5 | 0.5 | .75 |
| Totals | 500.000 | 100.0000 | 150 |

TABLE 6B

Pre-emulsion composition having 20% of a CLA-Containing Non-Polar Active Ingredient and 79.5% TPGS

| Ingredient | mg/ 0.5 mL serving | Percent (by weight) of pre-emulsion composition | g/batch |
|---|---|---|---|
| CLA (70%) (Non-Polar Active Ingredient) | 100 | 20 | 30 |
| Tocopherol Polyethylene Glycol Succinate (surfactant) | 397.5 | 79.5 | 119.25 |
| Benzyl alcohol (preservative) | 2.5 | 0.5 | .75 |
| Totals | 500.000 | 100.0000 | 150 |

TABLE 6C

Pre-emulsion composition having 30% of a CLA-Containing Non-Polar Active Ingredient and 69.5% TPGS

| Ingredient | mg/ 0.5 mL serving | Percent (by weight) of pre-emulsion composition | g/batch |
|---|---|---|---|
| CLA (70%) (Non-Polar Active Ingredient) | 150 | 30 | 45 |
| Tocopherol Polyethylene Glycol Succinate (surfactant) | 347.5 | 69.5 | 104.25 |
| Benzyl alcohol (preservative) | 2.5 | 0.5 | .75 |
| Totals | 500.000 | 100.0000 | 150 |

TABLE 6D

Pre-emulsion composition having 10% of a CLA-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| CLA (70%) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

Example 7

Pre-emulsion Compositions Having Coenzyme Q Containing Non-Polar Compounds (CoQ10)

Tables 7A-7F set forth the ingredients that were included in pre-emulsion compositions containing a non-polar active ingredient containing Coenzyme Q10. The non-polar active ingredient was a Coenzyme Q 10 (CoQ10) compound, sold under the name Kaneka Q10™ (USP Ubidicarenone) by Kaneka Nutrients, L.P., Pasadena, Tex., which contains greater than 98% ubidicarenone (ubiquinone). These pre-emulsion compositions were made as described in Example 1, above.

TABLE 7A

Pre-emulsion composition having 30% of a CoQ10-Containing Non-Polar Active Ingredient and 69.5% TPGS

| Ingredient | mg/ 0.5 mL serving | Percent (by weight) of pre-emulsion composition | g/batch |
|---|---|---|---|
| CoQ10 (ubidicarenone) (Non-Polar Active Ingredient) | 150 | 30 | 900 |
| Tocopherol Polyethylene Glycol Succinate (surfactant) | 347.5 | 69.5 | 2085 |
| Benzyl alcohol (preservative) | 2.5 | 0.5 | 15 |
| Totals | 500.000 | 100.0000 | 3000 |

TABLE 7B

Pre-emulsion composition having 10% of a CoQ10-Containing Non-Polar Active Ingredient, 79.5% TPGS and 10% Vitamin E Oil Solvent

| Ingredient | mg/ 0.5 mL serving | Percent (by weight) of pre-emulsion composition | g/batch |
|---|---|---|---|
| CoQ10 (ubidicarenone) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

TABLE 7C

Pre-emulsion composition having 12.5% of a CoQ10-Containing Non-Polar Active Ingredient and 87% TPGS

| Ingredient | mg/ 0.8 mL serving | Percent (by weight) of pre-emulsion composition | g/batch |
|---|---|---|---|
| CoQ10 (ubidicarenone) (Non-Polar Active Ingredient) | 100 | 12.5 | 264 |
| Tocopherol Polyethylene Glycol Succinate (surfactant) | 696 | 87.0 | 1837.44 |
| Benzyl alcohol (preservative) | 4 | 0.5 | 10.56 |
| Totals | 800.000 | 100.0000 | 2112 |

TABLE 7D

Pre-emulsion composition having 16.7% of a CoQ10-Containing Non-Polar Active Ingredient and 82.8% TPGS

| Ingredient | mg/ 0.6 mL serving | Percent (by weight) of pre-emulsion composition | g/batch |
|---|---|---|---|
| CoQ10 (ubidicarenone) (Non-Polar Active Ingredient) | 100 | 16.7 | 264.53 |
| Tocopherol Polyethylene Glycol Succinate (surfactant) | 497 | 82.8 | 1311.55 |
| Benzyl alcohol (preservative) | 3 | 0.5 | 7.92 |
| Totals | 600.000 | 100.0000 | 1584 |

TABLE 7E

Pre-emulsion composition having 22% of a CoQ10-Containing Non-Polar Active Ingredient and 77.5% TPGS

| Ingredient | mg/ 0.5 mL serving | Percent (by weight) of pre-emulsion composition | g/batch |
|---|---|---|---|
| CoQ10 (ubidicarenone) (Non-Polar Active Ingredient) | 110 | 22.0 | 55 |
| Tocopherol Polyethylene Glycol Succinate (surfactant) | 387.5 | 77.5 | 193.75 |
| Benzyl alcohol (preservative) | 2.5 | 0.5 | 1.25 |
| Totals | 500.000 | 100.0000 | 250 |

TABLE 7F

Pre-emulsion composition having 31.5% of a CoQ10-Containing Non-Polar Active Ingredient and 68% TPGS

| Ingredient | mg/ 0.5 mL serving | Percent (by weight) of pre-emulsion composition | g/batch |
|---|---|---|---|
| CoQ10 (ubidicarenone) (Non-Polar Active Ingredient) | 157.5 | 31.5 | 157.5 |
| Tocopherol Polyethylene Glycol Succinate (surfactant) | 340 | 68.0 | 340 |
| Benzyl alcohol (preservative) | 2.5 | 0.5 | 2.5 |
| Totals | 500.000 | 100.0000 | 500 |

Example 8

Pre-emulsion Compositions Having Phytosterol Containing Non-Polar Compounds

Tables 8A through 8G, below, set forth ingredients that were used to make pre-emulsion compositions with phytosterol-containing non-polar active ingredients.

Each of the pre-emulsion compositions set forth in Tables 8A-G contained a Phytosterols non-polar active ingredient. This non-polar active ingredient was a Phytosterols compound sold under the name CardioAid™, distributed by B&D Nutrition and manufactured by ADM Natural Health and Nutrition, Decatur, Ill., which contained Kosher, Pareve, and Halal plant sterols containing a minimum of 95% plant sterols.

As indicated in individual Tables, certain pre-emulsion compositions contained one or more additional non-polar active ingredient (e.g. CLA, Safflower Oil and/or saw palmetto extract).

The safflower oil additional non-polar active ingredient, and/or solvent, was a high linoleic safflower oil distributed by Jedwards, International, Inc., Quincy, Mass., which contained between 5% and 10% (specifically 6.65%) C:16 Palmitic acid, between 1% and 3% (specifically 2.81%) C:18 Stearic acid, between 12% and 18% (specifically 14.65%) 18:1 Oleic acid, between 70% and 80% (specifically 74.08%) C18:2 Linoleic acid and less than 1% (specifically 0.10%) C18:3 Linolenic acid.

The CLA additional non-polar active ingredient was a conjugated linolenic acid (CLA) compound, obtained from Sanmark, LTD (Dalian, Liaoning Province, China; product code 01057-A80), containing 80% CLA.

The saw palmetto extract additional non-polar active ingredient was saw Palmetto, Lipophilic Extract, commercially available from Natural Medicinals, Inc., Felda, Fla., which contained between about 85% and 90% total fatty acids, including 0.8% Caproic acid, 2% Caprylic acid, 2.4% Capric acid, 27.1 Lauric acid, 10.3 Myristic acid, 8.1% Palmitic acid, 0.2% Palmitoleic acid, 2% Stearic acid, 26.7 Oleic acid, 4.9% Linoleic acid, 0.7% linolenic acid, 0.42%; 0.42% phytosterols, including 0.42% beta Sitosterol, 0.09% Campesterol, 0.03% Stigmasterol; and 0.2% moisture.

Other pre-emulsion compositions, similar to the pre-emulsion compositions set forth in Tables 8A-8G below, could be made by including one or more other additional non-polar active ingredients, for example, CoQ10, fish oil, algae oil, borage oil, and/or another non-polar compound, for example, any of the non-polar compounds described herein.

As indicated in individual tables, certain pre-emulsion compositions set forth in Tables 8A-G contained one or more solvents. Exemplary of the solvents used is Vitamin E oil, sold by ADM Natural Health and Nutrition, Decatur, Ill., under the name Novatol™ 5-67 Vitamin E (D-alpha-Tocopherol; ADM product code 410217). This oil contained at least 67.2% Tocopherol and approximately 32.8% soybean oil. Also exemplary of the solvents used was a Flaxseed oil, obtained from Sanmark LLC, Greensboro, N.C. (Sanmark Limited, Dalian, Liaoning Province, China), which contains not less than (NLT) 50% C18:3 alpha-linolenic acid.

The surfactant used in each pre-emulsion composition in Tables 8A-G was a tocopherol polyethylene glycol succinate (TPGS) surfactant (the TPGS surfactant sold under the name Vitamin E TPGS® by Eastman Chemical Company). The preservative used in each pre-emulsion composition was a natural (GRAS-certified) preservative, benzyl alcohol.

Each of Tables 8A-G sets forth the total milligrams (mg) per serving and the mg of each ingredient per serving, the percentage by weight (of the total pre-emulsion composition), for each ingredient and the amount (g) of each ingredient that was added to make a batch of the indicated batch size (g).

Each of the pre-emulsion compositions set forth in Tables 8A-G was made using a bench-top process according to the provided methods. Each of the pre-emulsion compositions could be made alternatively by scaling up the bench-top process, to make the pre-emulsion compositions using a scaled-up manufacturing process of the provided methods, for example, to make larger batch sizes of the pre-emulsion compositions in the following Examples. Accordingly, each of the pre-emulsion compositions in Examples 8A-G also can be made with the provided methods, using the scaled-up process. The bench-top process for making the pre-emulsion compositions in Tables 8A-G was carried out using the following general steps.

For each of the pre-emulsion compositions, the indicated amount of each ingredient was weighed using a Toledo Scale (Model GD13x/USA), Sartorius Basic Analytical Scale (Model BA110S) or an OHAUS Scale (Model CS2000). Which scale was used depended on the weight of the particular ingredient.

The following initial ingredients, where indicated, were added, sequentially in the following order, to a vessel (a Pyrex® beaker): 1) any solvent(s) and additional non-polar active ingredient(s), in any order; 2) preservative, 3) phytosterols-containing non-polar active ingredient. These ingredients then were mixed, using a standard mixer (IKA® model No. RE-16 1S, which is an overhead mixer (laboratory stirrer) compatible with the bench-top process). While mixing, the ingredients were heated using a heating apparatus, a hot plate (a Thermolyne hot Plate Model #SP46615), until the temperature reached about 82.2° C. and the ingredients had dissolved (about 1 hour).

After the initial ingredients had dissolved, the mixture was filtered, without cooling, through a 100 micron filter. The surfactant (TPGS) then was added to the mixture and the mixture was homogenized by placing a reversible homogenizer (Arde Barinco, Inc.; Model CJ-4E) in the vessel and turning it on at 850-1200 RPM. Mixing with the homogenizer was continued while maintaining a temperature of between about 60° C. and about 82.2° C., using the hot plate. The baffle plate on the homogenizer was adjusted to achieve and maintain an emulsion, for example, by moving the baffle plate further into and/or out of the ingredient mixture. Homogenization was continued until the surfactant dissolved. A temperature probe (Model #DPP400W, Cooper-Atkins) was used for evaluation, as a temperature meter to measure the temperature of the ingredients. After all ingredients had dissolved, the mixture was filtered (before cooling) through a 100 micron filter. The filtered mixture was added to a vessel (a Pyrex® beaker). The surfactant then was added to the mixture.

The composition then was filtered, using a 100 micron end-product filter and then packaged (transferred) by filling into one or more storage containers, for example, plastic bottles or 5 gallon pails, where it was cooled to room temperature (about 25° C.). Alternatively, the mixture could be packaged into a bag-in-a-box type storage container. The mixture became a solid at room-temperature, having a waxy consistency. Thus, each of the pre-emulsion compositions in Examples 2-7 was a semi-solid or solid at room temperature, having a waxy consistency, and became liquid upon heating, for example, to 60° C.

TABLE 8A

Pre-emulsion composition with 10% of a Phytosterols Non-Polar Active Ingredient, 79.5% TPGS and 10% Vitamin E Oil Solvent

| Ingredient | mg/ 0.5 mL serving | Percent (by weight) of pre-emulsion composition | g/batch |
| --- | --- | --- | --- |
| Phytosterols (NLT 95%) (Non-Polar Active Ingredient) | 50 | 10 | 15 |
| Tocopherol Polyethylene Glycol Succinate (surfactant) | 397.5 | 79.5 | 119.25 |
| Benzyl alcohol (preservative) | 2.5 | 0.5 | .75 |
| Vitamin E Oil 5-67 (Solvent) | 50 | 10 | 15 |
| Totals | 500.000 | 100.0000 | 150 |

TABLE 8B

Pre-emulsion composition with 10.5% of a Phytosterols Non-Polar Active Ingredient, 54% TPGS, 30% Flaxseed Oil Solvent, and 5% Saw Palmetto Extract

| Ingredient | mg/ 1 mL serving | Percent (by weight) of pre-emulsion composition | g/batch |
|---|---|---|---|
| Phytosterols (NLT 95%) (Non-Polar Active Ingredient) | 105 | 10.5 | 10.5 |
| Tocopherol Polyethylene Glycol Succinate (surfactant) | 540 | 54 | 54 |
| Benzyl alcohol (preservative) | 5 | 0.5 | 0.5 |
| Flaxseed Oil (Solvent) | 300 | 30 | 30 |
| Saw Palmetto Extract (Additional Non-Polar Active Ingredient) | 50 | 5 | 5 |
| Totals | 500.000 | 100.0000 | 100 |

TABLE 8C

Pre-emulsion composition with 10.5% of a Phytosterols Non-Polar Active Ingredient, 49.5% TPGS, and 45% Flaxseed Oil Solvent

| Ingredient | mg/ 1 mL serving | Percent (by weight) of pre-emulsion composition | g/batch |
|---|---|---|---|
| Phytosterols (NLT 95%) (Non-Polar Active Ingredient) | 50 | 5 | 5 |
| Tocopherol Polyethylene Glycol Succinate (surfactant) | 495 | 49.5 | 49.5 |
| Benzyl alcohol (preservative) | 5 | 0.5 | 0.5 |
| Flaxseed Oil (Solvent) | 450 | 45 | 45 |
| Totals | 500.000 | 100.0000 | 100 |

TABLE 8D

Pre-emulsion composition with 5% of a Phytosterols Non-Polar Active Ingredient, 45% CLA-containing Non-Polar Active Ingredient, and 49.5% TPGS

| Ingredient | mg/ 1 mL serving | Percent (by weight) of pre-emulsion composition | g/batch |
|---|---|---|---|
| Phytosterols (NLT 95%) (Non-Polar Active Ingredient) | 50 | 5 | 5 |
| Tocopherol Polyethylene Glycol Succinate (surfactant) | 495 | 49.5 | 49.5 |
| Benzyl alcohol (preservative) | 5 | 0.5 | 0.5 |
| CLA (NLT 80%) (Additional Non-Polar Active Ingredient) | 450 | 45 | 45 |
| Totals | 500.000 | 100.0000 | 100 |

TABLE 8E

Pre-emulsion composition with 10% of a phytosterols non-polar active ingredient, 40% CLA-containing Non-Polar Active Ingredient, and 49.5% TPGS

| Ingredient | mg/ 1 mL serving | Percent (by weight) of pre-emulsion composition | g/batch |
|---|---|---|---|
| Phytosterols (NLT 95%) (Non-Polar Active Ingredient) | 100 | 10 | 10 |
| Tocopherol Polyethylene Glycol Succinate (surfactant) | 495 | 49.5 | 49.5 |
| Benzyl alcohol (preservative) | 5 | 0.5 | 0.5 |
| CLA (NLT 80%) (Additional Non-Polar Active Ingredient) | 400 | 40 | 40 |
| Totals | 500.000 | 100.0000 | 100 |

TABLE 8F

Pre-emulsion composition with 10.5% of a phytosterols non-polar active ingredient, 40% CLA-containing Non-Polar Active Ingredient, 1% saw palmetto extract and 54% TPGS

| Ingredient | mg/ 1 mL serving | Percent (by weight) of pre-emulsion composition | g/batch |
|---|---|---|---|
| Phytosterols (NLT 95%) (Non-Polar Active Ingredient) | 105 | 10.5 | 10.5 |
| Tocopherol Polyethylene Glycol Succinate (surfactant) | 540 | 54 | 54 |
| Benzyl alcohol (preservative) | 5 | 0.5 | 0.5 |
| CLA (NLT 80%) (Additional Non-Polar Active Ingredient) | 340 | 34 | 34 |
| Saw Palmetto Extract (Additional Non-Polar Active Ingredient) | 10 | 1 | 1 |
| Totals | 500.000 | 100.0000 | 100 |

TABLE 8G

Pre-emulsion composition with 10.5% of a phytosterols non-polar active ingredient, , 1% saw palmetto extract, 34% safflower oil and 54% TPGS

| Ingredient | mg/ 1 mL serving | Percent (by weight) of pre-emulsion composition | g/batch |
|---|---|---|---|
| Phytosterols (NLT 95%) (Non-Polar Active Ingredient) | 105 | 10.5 | 10.5 |
| Tocopherol Polyethylene Glycol Succinate (surfactant) | 540 | 54 | 54 |
| Benzyl alcohol (preservative) | 5 | 0.5 | 0.5 |
| Safflower Oil (Additional Non-Polar Active Ingredient) | 340 | 34 | 34 |
| Saw Palmetto Extract (Additional Non-Polar Active Ingredient) | 10 | 1 | 1 |
| Totals | 500.000 | 100.0000 | 100 |

Example 9

Dilution of the Pre-emulsion Compositions and Evaluation of the Liquid Dilution Compositions For evaluation of various properties, selected pre-emulsion compositions described in the Examples above, were diluted, according to the provided methods, in aqueous medium to form aqueous liquid dilution compositions. The results are described in detail in the Examples below.

Example 9A

Dilution and Evaluation of Clarity of the Dilution Compositions: Turbidity Analysis The DHA-containing pre-emulsion composition made in Example 2B(iii) and the CoQ10-containing pre-emulsion composition made in Example 7 each were diluted in aqueous medium, according to the provided methods for diluting the pre-emulsion compositions. The resulting aqueous liquid dilution compositions then were evaluated for clarity by measuring turbidity using a nephelometer. Dilution parameters and results of the evaluation are set forth in Table 9A below. For each sample listed in Table 9A, the Example in which the pre-emulsion composition was made is indicated.

Each of the pre-emulsion compositions listed in Table 9A was diluted by adding the amount of pre-emulsion composition indicated in Table 9A to the amount of water (purified according to the provided methods) indicated in Table 9A. Approximate dilution factors also are listed. The pre-emulsion compositions were diluted in aqueous medium according to the provided methods for diluting the pre-emulsion compositions, using the following steps:

The indicated amount of water was heated in a Pyrex® beaker, which was placed on a Thermolyne hot plate (Model #846925), until the water reached 49.8° C. The indicated amount of the pre-emulsion composition (about 1 g) then was added to the heated water, and stirred with a stir rod until dispersed. Alternatively, the dilution can be carried out by heating the pre-emulsion composition prior to addition to the water. The resulting aqueous liquid dilution composition containing the non-polar active ingredient was cooled to room temperature (about 25° C.). The cooled liquid dilution composition was added to an Alcon amber-glass screw-top vial, for evaluation. The DHA-containing liquid dilution composition made from the pre-emulsion composition of Example 2B(iii) included 17.5 mg of DHA in 1000 g (1 L) water.

The vials containing the liquid dilution compositions were sent to ACZ Laboratories, Inc., Steamboat Springs, Colo., for turbidity analysis using a nephelometer. Results are listed in the form of Nephelometric Turbidity Units (NTU) and are indicated in Table 9A below. As shown in Table 9A, each of the liquid aqueous compositions containing the diluted pre-emulsion compositions had an NTU value of less than 300, for example, less than about 200.

TABLE 9A

Turbidity (NTU) of liquid aqueous compositions containing the pre-emulsion compositions

| Pre-emulsion composition of: | Non-Polar Active Ingredient | Pre-emulsion composition (grams) | Water (grams) | Approx. Dilution | NTU |
|---|---|---|---|---|---|
| Example 2B (iii) | DHA-containing (Algae Oil) | 1.0524 | 1000 | 1:1000 | 165 |
| Example 7A | CoQ10-Containing | 0.1661 | 250 | 1:1500 | 208 |

Example 9B

Dilution and Evaluation of Clarity of the Dilution Compositions: Particle Size The CoQ10-containing pre-emulsion composition of Example 7A, above was sent to Delta Analytical Instruments, Inc for measurement of average particle size, which was carried out using the Horiba® LB-550 light-scattering analyzer. For this process, the pre-emulsion composition from Example 7 was diluted, according to the provided methods, in aqueous medium to form an aqueous liquid dilution composition. To dilute the compositions for this analysis, the sample was mixed well and heated in a water bath at 50° C. Then, a few drops of the sample was added to 25 mL of water, which also had been heated to 50° C. This sample then was cooled to room temperature (25° C.). and put into a cell, which was used to measure average particle size on the Horibag LB-550 light-scattering analyzer. The clarity of the liquid dilution composition then was evaluated by measuring average particle size. Results included measurement of the average particle size in the dilution composition, which was measured three times, in separate runs. The measurement for each run and the average of the three runs, are indicated in Table 9B, below. As indicated in Table 9B, the particle size of the liquid dilution composition was less than 150 nm.

TABLE 9B

Particle size of Liquid dilution composition containing coenzyme Q10 pre-emulsion composition

|  | Average Particle Size (nm) |
|---|---|
| Run 1 | 129.7 |
| Run 2 | 120.2 |
| Run 3 | 123.5 |
| Average | 124.5 |

Example 10

Free Flowing Powders Having Coenzyme Q Containing Non-Polar Compounds (CoQ10)

The pre-emulsion concentrates of Tables 7C-7F were spray dried to form free flowing powders containing a non-polar active ingredient containing Coenzyme Q10 according to the general steps described below.

Each of the free flowing powders contained one or more excipients, selected from maltodextrin and gum acacia. The excipients were dissolved in water while heating to a temperature of 60° C. in a stainless steel tank with a 25 horsepower mixer. The ratio of water to excipients was 2 to 1. The maltodextrin was GRAS certified Maltrin® maltodextrins, made by Grain Processing Corporation, Muscatine, Iowa, which contained mixtures of glucose polymers and had a dextrose equivalence (DE) of less than 20. After the excipients were dissolved, the pre-emulsion concentrates were heated to a temperature of 60° C. and homogenized with the dissolved excipients using a piston driven homogenizer.

The final mixture containing the pre-emulsion composition encapsulated in the excipients was spray dried using a cyclone type spray dryer. During this process, the encapsulated pre-emulsion composition was transferred to the spray drier using a diastolic pump and water was slowly evaporated while heating and with pressure Each of the resultant products was a free flowing powder containing coenzyme Q10 with a particle size of less than 1 micron. The resultant free flowing powders have the same NTU as the pre-emulsion concentrates of Tables 7C-7F. The amount and % by weight of the components of the powders are set forth in Tables 10A-10D.

TABLE 10A

Free Flowing Powder having 5% of a CoQ10-Containing Non-Polar Active Ingredient and 34.8% TPGS

| Ingredient | mg/ 2 mL serving | Percent (by weight) of free flowing powder | g/batch |
|---|---|---|---|
| CoQ10 (ubidicarenone) (Non-Polar Active Ingredient) | 100 | 5 | 264 |
| Tocopherol Polyethylene Glycol Succinate (surfactant) | 697.5 | 34.875 | 1841.4 |
| Benzyl alcohol (preservative) | 2.5 | 0.125 | 6.6 |
| 35% Maltodextrin and 65% Gum Acacia (excipients) | 1200 | 60 | 3168.0 |
| Totals | 2000.000 | 100.0000 | 5280.0 |

TABLE 10B

Free Flowing Powder having 5% of a CoQ10-Containing Non-Polar Active Ingredient and 24.8% TPGS

| Ingredient | mg/ 2 mL serving | Percent (by weight) of free flowing powder | g/batch |
|---|---|---|---|
| CoQ10 (ubidicarenone) (Non-Polar Active Ingredient) | 100 | 5 | 264 |
| Tocopherol Polyethylene Glycol Succinate (surfactant) | 497.5 | 24.875 | 1313.4 |
| Benzyl alcohol (preservative) | 2.5 | 0.125 | 6.6 |
| 35% Maltodextrin and 65% Gum Acacia (excipients) | 1400 | 70 | 3696 |
| Totals | 2000.000 | 100.0000 | 5280 |

TABLE 10C

Free Flowing Powder having 5.5% of a CoQ10-Containing Non-Polar Active Ingredient and 19.3% TPGS

| Ingredient | mg/ 2 mL serving | Percent (by weight) of free flowing powder | g/batch |
|---|---|---|---|
| CoQ10 (ubidicarenone) (Non-Polar Active Ingredient) | 110 | 5.5 | 55 |
| Tocopherol Polyethylene Glycol Succinate (surfactant) | 387.5 | 19.375 | 193.75 |
| Benzyl alcohol (preservative) | 2.5 | 0.125 | 1.25 |
| 35% Maltodextrin and 65% Gum Acacia (excipients) | 1500 | 75 | 750 |
| Totals | 2000.000 | 100.0000 | 1000 |

TABLE 10D

Free Flowing Powder having 7.875% of a CoQ10-Containing Non-Polar Active Ingredient and 17% TPGS

| Ingredient | mg/ 2 mL serving | Percent (by weight) of free flowing powder | g/batch |
|---|---|---|---|
| CoQ10 (ubidicarenone) (Non-Polar Active Ingredient) | 157.5 | 7.875 | 157.5 |
| Tocopherol Polyethylene Glycol Succinate (surfactant) | 340 | 17 | 340 |
| Benzyl alcohol (preservative) | 2.5 | 0.125 | 2.5 |
| 35% Maltodextrin and 65% Gum Acacia (excipients) | 1500 | 75 | 1500 |
| Totals | 2000.000 | 100.0000 | 2000 |

Since modifications will be apparent to those of skill in this art, it is intended that this invention be limited only by the scope of the appended claims.

The invention claimed is:

1. A non-aqueous pre-emulsion composition, consisting essentially of:
a polyethylene glycol (PEG)-derivative of Vitamin E in an amount between 65% and 95%, by weight, of the pre-emulsion composition;
a non-polar ingredient selected from among any one or more polyunsaturated fatty acids in an amount between 5% and 35%, by weight, of the pre-emulsion composition; and
one or more additional ingredients selected from among co-surfactants in an amount up to 1%, by weight, of the composition, emulsion stabilizers in an amount up to 1%, by weight, of the composition, preservatives in an amount up to 1%, by weight, of the composition, flavors in an amount up to 1%, by weight, of the composition, pH adjusters in an amount up to 1%, by weight, of the composition, and non-polar solvents that dissolve the non-polar active ingredient and differ therefrom in an amount up to 10%, by weight, of the composition,
wherein:
the pre-emulsion composition has a waxy consistency, whereby it is a solid or semi-solid at room temperature;
not more than 1%, by weight, of the composition, comprises hydrophilic ingredients(s), and the composition is a non-aqueous composition;
the non-polar ingredient(s) is/are the active ingredient in the composition; and
all the ingredients, including the non-polar ingredient, the PEG-derivative of Vitamin E, and the additional ingredients are 100%, by weight, of the composition.

2. A method for making a non-aqueous pre-emulsion composition, wherein the composition comprises:
a polyethylene glycol (PEG)-derivative of Vitamin E in an amount between 65% and 95%, by weight, of the pre-emulsion composition; and
one or more non-polar ingredients selected from among any one or more of polyunsaturated fatty acids, coenzyme Q10 compounds and phytosterols in an amount between 5% and 35%, by weight, of the pre-emulsion composition, wherein not more than 1%, by weight, of the resulting composition, comprises hydrophilic ingredients(s);
the method, comprising:
(a) mixing and heating the PEG-derivative of Vitamin E; and any ingredients other than the non-polar ingredient; and then (b) adding the one or more non-polar ingredients to the heated mixture of (a);
(c) homogenizing the ingredients;
(d) cooling the homogenized ingredients, whereby the homogenized ingredients become waxy in consistency and contain no more than 1% hydrophilic ingredients, thereby generating the non-aqueous pre-emulsion composition.

3. A method for making a non-aqueous pre-emulsion composition, wherein the composition comprises:
a polyethylene glycol (PEG)-derivative of Vitamin E in an amount between 65% and 95%, by weight, of the pre-emulsion composition;
one or more non-polar ingredients selected from among any one or more of polyunsaturated fatty acids, coenzyme Q10 compounds and phytosterols in an amount between 5% and 35%, by weight, of the pre-emulsion composition, wherein not more than 1%, by weight, of the resulting composition, comprises hydrophilic ingredients(s); and
a preservative that contains benzyl alcohol;
the method, comprising:
(a) mixing and heating the PEG-derivative of Vitamin E with ingredients other than the non-polar ingredient; and then
(b) adding the one or more non-polar ingredients to the heated mixture of (a);
(c) homogenizing the ingredients; and
(d) cooling the homogenized ingredients, whereby the homogenized ingredients become waxy in consistency and contain no more than 1% hydrophilic ingredients, thereby generating the non-aqueous pre-emulsion composition.

4. A method for making a non-aqueous pre-emulsion composition, wherein the composition comprises:
a polyethylene glycol (PEG)-derivative of Vitamin E in an amount between 65% and 95%, by weight, of the pre-emulsion composition; and
one or more non-polar ingredients in an amount between 5% and 35%, by weight, of the pre-emulsion composition, wherein not more than 1%, by weight, of the resulting composition, comprises hydrophilic ingredients(s), wherein the non-polar active ingredients contain at least one polyunsaturated fatty acid selected from among omega-3 fatty acids, omega-6 fatty acids and conjugated fatty acids;
the method, comprising:
(a) mixing and heating the PEG-derivative of Vitamin E and ingredients other than the non-polar ingredient; and then
(b) adding the one or more non-polar ingredients to the heated mixture of (a);
(c) homogenizing the ingredients;
(d) cooling the homogenized ingredients, whereby the homogenized ingredients become waxy in consistency and contain no more than 1% hydrophilic ingredients, thereby generating the non-aqueous pre-emulsion composition.

5. A non-aqueous pre-emulsion composition, consisting essentially of:
a polyethylene glycol (PEG)-derivative of Vitamin E in an amount between 79% and 90%, by weight, of the pre-emulsion composition; and
a non-polar ingredient other than the PEG-derivative of Vitamin E selected from among any one or more of polyunsaturated fatty acids, coenzyme Q10 compounds and phytosterols in an amount between 10% and 20%, by weight, of the pre-emulsion composition; and
one or more additional ingredients selected from co-surfactants in an amount up to 1%, by weight, of the composition, emulsion stabilizers in an amount up to 1%, by weight, of the composition, preservatives in an amount up to 1%, by weight, of the composition, flavors in an amount up to 1%, by weight, of the composition, pH adjusters in an amount up to 1%, by weight, of the composition, and non-polar solvents that dissolve the non-polar active ingredient and differ therefrom in an amount up to 10%, by weight, of the composition, wherein:
the pre-emulsion composition is a solid or semi-solid at room temperature;
not more than 1%, by weight, of the composition, comprises hydrophilic ingredients(s);
the non-polar ingredients) is/are the active ingredient in the composition; and
all the ingredients, including the non-polar ingredient, the PEG-derivative of Vitamin E, and the optional additional ingredients comprise 100%, by weight, of the composition.

6. A non-aqueous pre-emulsion composition, consisting essentially of:
a polyethylene glycol (PEG)-derivative of Vitamin E in an amount between 65% and 95%, by weight, of the pre-emulsion composition; and,
as the active ingredient in the composition, one or more non-polar compounds selected from among any one or more polyunsaturated fatty acids in an amount between 5% and 35%, by weight, of the pre-emulsion composition.

7. A non-aqueous pre-emulsion composition, consisting essentially of:
a polyethylene glycol (PEG)-derivative of Vitamin E in an amount between 79% and 90%, by weight, of the pre-emulsion composition; and,
as the active ingredient in the composition, one or more non-polar compounds selected from among one or more polyunsaturated fatty acids, coenzyme Q10 compounds and phytosterols in an amount between 10% and 20%, by weight, of the pre-emulsion composition.

8. The pre-emulsion composition of claim 1, wherein the polyethylene glycol (PEG)-derivative of Vitamin E is a tocopherol polyethylene glycol diester (TPGD).

9. The pre-emulsion composition of claim 8, wherein the TPGD is selected from among tocopherol polyethylene glycol succinate (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, or a TPGS analog.

10. The pre-emulsion composition of claim 9, wherein the TPGS is TPGS-1000 or D-α TPGS.

11. The pre-emulsion composition of claim 1, wherein the PEG-derivative of Vitamin E contains a PEG moiety selected from among any one or more of methylated PEG (m-PEG), PEG-OH, PEG-NHS, PEG-aldehyde, PEG-SH, PEG-NH$_2$, PEG-CO$_2$H, and branched PEGs.

12. The pre-emulsion composition of claim 1, the PEG-derivative of Vitamin E contains a PEG moiety having a molecular weight of between about 200 Daltons to about 20,000 Daltons.

13. The pre-emulsion composition of claim 1 that contains a preservative in an amount sufficient to preserve the composition.

14. The pre-emulsion composition of claim 13, wherein the preservative contains benzyl alcohol.

15. The pre-emulsion composition of claim 1 that contains a solvent that dissolves the non-polar active ingredient and differs therefrom, wherein the amount of solvent is sufficient to dissolve the non-polar active ingredient.

16. The pre-emulsion composition of claim 15, wherein the solvent contains a Vitamin E oil, a flaxseed oil or a combination thereof.

17. The pre-emulsion composition of claim 1 that contains an emulsion stabilizer, at an amount sufficient to stabilize the composition.

18. The pre-emulsion composition of claim 1 that contains a co-surfactant, at an amount sufficient to stabilize the composition.

19. The pre-emulsion composition of claim 18, wherein the co-surfactant contains a phospholipid.

20. The pre-emulsion composition of claim 19, wherein the co-surfactant contains phosphatidylcholine.

21. The pre-emulsion composition of claim 1, wherein the non-polar active ingredient contains at least one polyunsaturated fatty acid selected from among omega-3 fatty acids, omega-6 fatty acids and conjugated fatty acids.

22. The pre-emulsion composition of claim 21, wherein the non-polar active ingredient contains a polyunsaturated fatty acid selected from among a docosahexaenoic acid (DHA), an eicosapentaenoic acid (EPA), a fish oil, a flaxseed oil, a borage oil, an alpha-linolenic acid (ALA), a gamma-linolenic acid (GLA), a conjugated linolenic acid (CLA), and a saw palmetto extract.

23. The method of claim 3, wherein the ingredients include the non-polar solvent that dissolves the non-polar active ingredient and differs therefrom, wherein the amount of solvent is sufficient to dissolve the non-polar active ingredient.

24. The method of claim 23, wherein the non-polar solvent comprises a Vitamin E oil, a flaxseed oil or a combination thereof.

25. The method of claim 23, wherein the amount of the non-polar solvent is between 1% and 6% of the composition.

26. The method of claim 3, wherein heating comprises heating the ingredients to 40° C. to 60° C.

27. The method of claim 3, wherein the homogenizing is performed with a reversible homogenizer.

28. The method of claim 3, wherein the ingredients include a co-surfactant in an amount sufficient to stabilize the composition.

29. The method of claim 28, wherein the co-surfactant contains a phospholipid.

30. The method of claim 29, wherein the phospholipid comprises phosphatidylcholine.

31. The method of claim 2, wherein the ingredients include at least one preservative in an amount sufficient to preserve the composition.

32. The method of claim 3, wherein the ingredients include an emulsion stabilizer in an amount sufficient to stabilize the composition.

33. The method of claim 4, wherein the non-polar active ingredients contain a polyunsaturated fatty acid selected from among a docosahexaenoic acid (DHA), an eicosapentaenoic acid (EPA), a fish oil, a flaxseed oil, a borage oil, an alpha-linolenic acid (ALA), a gamma-linolenic acid (GLA), a conjugated linolenic acid (CLA), and a saw palmetto extract.

34. The method of claim 31, wherein the PEG-derivative of Vitamin E is a tocopherol polyethylene glycol diester (TPGD).

35. The method of claim 34, wherein the TPGD is selected from among tocopherol polyethylene glycol succinate (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, or a TPGS analog.

36. The method of claim 35, wherein the TPGD is a TPGS-1000 or D-αTPGS.

37. The method of claim 3, wherein the PEG-derivative of Vitamin E contains a PEG moiety selected from among any one or more of PEG-OH, PEG-NHS, PEG-aldehyde, PEG-SH, PEG-NH$_2$, PEG-CO$_2$H, methylated PEGs (m-PEGs) and branched PEGs.

38. The method of claim 3, wherein the PEG-derivative of Vitamin E contains a PEG moiety having a molecular weight of between 200 Daltons or about 200 Daltons to 20,000 Daltons or about 20,000 Daltons, between 200 Daltons or about 200 Daltons and 6000 Daltons or about 6000 Daltons, between 600 Daltons or about 600Daltons and 6000 Daltons or about 6000 Daltons, between 200 Daltons or about 200 Daltons and 2000 Daltons or about 2000 Daltons, between 600 Daltons or about 600 Daltons and 1500 Daltons or about 1500 Daltons, or between 600 Daltons or about 600 Daltons and 1000 or about 1000 Daltons.

39. A method of providing an oil-based additive in a beverage, comprising:
adding a pre-emulsion composition of claim 1, to a beverage, in an amount whereby: the beverage contains an effective amount of the non-polar ingredient.

40. The method of claim 39, wherein the non-polar active ingredient is selected from among an omega-3 fatty acid, an omega-6 fatty acid, a conjugated fatty acid and a saw palmetto extract.

41. The method of claim 39, wherein the non-polar active ingredient is selected from among coenzyme Q10, a docosahexaenoic acid (DHA), an eicosapentaenoic acid (EPA), a fish oil, a flaxseed oil, a borage oil, an alpha-linolenic acid (ALA), a gamma-linolenic acid (GLA), a conjugated linolenic acid (CLA) and a saw palmetto extract.

42. The method of claim 39, further comprising heating the pre-emulsion composition, the beverage, or both the pre-emulsion composition and the beverage, prior to addition of the pre-emulsion composition to the beverage.

43. The method of claim 39, further comprising heating the mixture of the beverage and the pre-emulsion composition.

44. The method of claim 42, wherein the heating comprises heating to at least 40° C. or at least about 40° C.; or at least 120° F. or about 120° F.

45. The method of claim 39, further comprising cooling the beverage to at least 25° C. or about 25° C.

46. The method of claim 39, wherein the beverage is water, soda, milk, juice or a sports nutrition beverage.

47. The method of claim 39, wherein the beverage containing the additive is about as clear as the beverage in the absence of the additive.

48. The pre-emulsion composition of claim 1, wherein the PEG-derivative of Vitamin E contains a PEG moiety having a molecular weight of between about 200 Daltons and about 6000 Daltons, between about 600 Daltons and about 6000 Daltons, between about 200 Daltons and about 2000 Daltons, between about 600 Daltons and about 1500 Daltons, or between about 600 Daltons and about 1000 Daltons.

49. The pre-emulsion composition of claim 5, wherein the polyethylene glycol (PEG)-derivative of Vitamin E is a tocopherol polyethylene glycol diester (TPGD).

50. The pre-emulsion composition of claim 49, wherein the TPGD is selected from among tocopherol polyethylene glycol succinate (TPGS), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, or a TPGS analog.

51. The pre-emulsion composition of claim 50, wherein the TPGD is TPGS.

52. The pre-emulsion composition of claim 51, wherein the TPGS is TPGS-1000 or D-α TPGS.

53. The pre-emulsion composition of claim 5, wherein the non-polar ingredient is a coenzyme Q10 compound.

54. The pre-emulsion composition of claim 1, wherein the amount of the non-polar ingredient is between 10% and 30%, by weight of the composition.

55. The pre-emulsion composition of claim 6, wherein the PEG-derivative of vitamin E is a tocopherol polyethylene glycol succinate (TPGS).

56. The pre-emulsion composition of claim 7, wherein the PEG-derivative of vitamin E is a tocopherol polyethylene glycol succinate (TPGS).

57. The pre-emulsion composition of claim 55, wherein the TPGS is TPGS-1000.

58. The pre-emulsion composition of claim 56, wherein the TPGS is TPGS-1000.

59. The pre-emulsion composition of claim 9, wherein the TPGS is TPGS-1000.

60. The method of claim 2, wherein the PEG-derivative of vitamin E is a tocopherol polyethylene glycol succinate (TPGS).

61. The method of claim 60, wherein the TPGS is TPGS-1000.

62. The method of claim 4, wherein the PEG-derivative of vitamin E is a tocopherol polyethylene glycol succinate (TPGS).

63. The method of claim 62, wherein the TPGS is TPGS-1000.

* * * * *

UNITED STATES PATENT AND TRADEMARK OFFICE
CERTIFICATE OF CORRECTION

PATENT NO. : 8,765,661 B2
APPLICATION NO. : 12/383241
DATED : July 1, 2014
INVENTOR(S) : Philip J. Bromley It is certified that error appears in the above-identified patent and that said Letters Patent is hereby corrected as shown below:

IN THE TITLE PAGES:

In Item (56) References Cited, at page 1, column II, line 39, please replace "8/2002" with —9/2009—;

at page 1, column II, line 46, please replace "Vitamen-E TPGS" with —Vitamin-E TPGS—; and at page 2, column I, line 68, please replace "WO 200/029046" with —WO 2009/029046—.

IN THE SPECIFICATION:

At column 35, line 30, please replace "(a-Linolenic acid; ALA)" with —(α-Linolenic acid; ALA)—;

at column 53, line 65, please replace "omega-3 (6)$_3$; n-3)" with —omega-3 (ω-3; n-3)—;

at column 66, line 14, please replace "esterifyifig" with —esterifying—;

at column 82, line 33, please replace "Chum Mixers" with —Churn Mixers—;

at column 86, lines 62-63, please replace "3) 4) non-polar active ingredient(s)." with —3) non-polar active ingredient(s). In this example, the non-polar active ingredient(s) typically is added after the other ingredients have dissolved, prior to homogenization. In another example, when the composition includes one or more of a surfactant, a preservative, solvent and non-polar active ingredient, these ingredients are added sequentially, in the following order: 1) surfactant(s), 2) preservative(s), 3) solvent(s), 4) non-polar active ingredient(s)—;

at column 89, line 60, please replace "LIGHTNING" with —LIGHTNIN®—; and at column 112, line 19, please replace "Horibag LB-550" with —Horiba® LB-550—.

Signed and Sealed this
Eighteenth Day of August, 2015

Michelle K. Lee
*Director of the United States Patent and Trademark Office*

CERTIFICATE OF CORRECTION (continued)
U.S. Pat. No. 8,765,661 B2

IN THE CLAIMS:

Column 115, line 35 to line 59 should read

4. A method for making a non-aqueous pre-emulsion composition, wherein the composition comprises:

a polyethylene glycol (PEG)-derivative of Vitamin E in an amount between 65% and 95%, by weight, of the pre-emulsion composition; and one or more non-polar ingredients in an amount between 5% and 35%, by weight, of the pre-emulsion composition, wherein not more than 1%, by weight, of the resulting composition, comprises hydrophilic ingredients(s), wherein the non-polar ingredients contain at least one polyunsaturated fatty acid selected from among omega-3 fatty acids, omega-6 fatty acids and conjugated fatty acids;

the method, comprising:

(a) mixing and heating the PEG-derivative of Vitamin E and ingredients other than the non-polar ingredient; and then (b) adding the one or more non-polar ingredients to the heated mixture of (a);

(c) homogenizing the ingredients;

(d) cooling the homogenized ingredients, whereby the homogenized ingredients become waxy in consistency and contain no more than 1% hydrophilic ingredients, thereby generating the non-aqueous pre-emulsion composition.

Column 115, line 60 to column 116, line 24 should read

5. A non-aqueous pre-emulsion composition, consisting essentially of:

a polyethylene glycol (PEG)-derivative of Vitamin E in an amount between 79% and 90%, by weight, of the pre-emulsion composition;

a non-polar ingredient other than the PEG-derivative of Vitamin E selected from among any one or more of polyunsaturated fatty acids, coenzyme Q10 compounds and phytosterols in an amount between 10% and 20%, by weight, of the pre-emulsion composition; and one or more additional ingredients selected from co-surfactants in an amount up to 1%, by weight, of the composition, emulsion stabilizers in an amount up to 1%, by weight, of the composition, preservatives in an amount up to 1%, by weight, of the composition, flavors in an amount up to 1%, by weight, of the composition, pH adjusters in an amount up to 1%, by weight, of the composition, and non-polar solvents that dissolve the non-polar active ingredient and differ therefrom in an amount up to 10%, by weight, of the composition, wherein:

the pre-emulsion composition is a solid or semi-solid at room temperature;

not more than 1%, by weight, of the composition, comprises hydrophilic ingredients(s);

the non-polar ingredient(s) is/are the active ingredient in the composition; and all the ingredients, including the non-polar ingredient, the PEG-derivative of Vitamin E, and the optional additional ingredients comprise 100%, by weight, of the composition.

CERTIFICATE OF CORRECTION (continued)
U.S. Pat. No. 8,765,661 B2

Column 117, line 17 to line 19 should read

17. The pre-emulsion composition of claim 1 that contains an emulsion stabilizer, at an amount sufficient to stabilize the composition.

Column 117, line 38 to line 41 should read

23. The method of claim 3, wherein the ingredients include the non-polar solvent that dissolves the non-polar ingredient and differs therefrom, wherein the amount of solvent is sufficient to dissolve the non-polar ingredient.

Column 118, line 3 to line 5 should read

34. The method of claim 3, wherein the PEG-derivative of Vitamin E is a tocopherol polyethylene glycol diester (TPGD).

Column 118, line 24 to line 34 should read

38. The method of claim 3, wherein the PEG-derivative of Vitamin E contains a PEG moiety having a molecular weight of between 200 Daltons or about 200 Daltons to 20,000 Daltons or about 20,000 Daltons, between 200 Daltons or about 200 Daltons and 6000 Daltons or about 6000 Daltons, between 600 Daltons or about 600 Daltons and 6000 Daltons or about 6000 Daltons, between 200 Daltons or about 200 Daltons and 2000 Daltons or about 2000 Daltons, between 600 Daltons or about 600 Daltons and 1500 Daltons or about 1500 Daltons, or between 600 Daltons or about 600 Daltons and 1000 or about 1000 Daltons.

Column 118, line 66 to column 119, line 5 should read

48. The pre-emulsion composition of claim 1, wherein the PEG-derivative of Vitamin E contains a PEG moiety having a molecular weight of between about 200 Daltons and about 6000 Daltons, between about 600 Daltons and about 6000 Daltons, between about 200 Daltons and about 2000 Daltons, between about 600 Daltons and about 1500 Daltons, or between about 600 Daltons and about 1000 Daltons.

UNITED STATES PATENT AND TRADEMARK OFFICE
CERTIFICATE OF CORRECTION

| | | |
|---|---|---|
| PATENT NO. | : 8,765,661 B2 | Page 1 of 1 |
| APPLICATION NO. | : 12/383241 | |
| DATED | : July 1, 2014 | |
| INVENTOR(S) | : Bromley | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 834 days.

Signed and Sealed this
First Day of September, 2015

Michelle K. Lee
*Director of the United States Patent and Trademark Office*